United States Patent
Bailey et al.

(10) Patent No.: US 10,597,698 B2
(45) Date of Patent: Mar. 24, 2020

(54) CHROMATIN IMMUNOCAPTURE DEVICES AND METHODS OF USE

(71) Applicants: THE BOARD OF TRUSTEES OF THE UNIVERSITY OF ILLINOIS, Urbana, IL (US); MAYO FOUNDATION FOR MEDICAL EDUCATION AND RESEARCH, Rochester, MN (US)

(72) Inventors: Ryan Bailey, Urbana, IL (US); Joshua Tice, Evanston, IL (US); Tamas Ordog, Rochester, MN (US); Jeong Heon Lee, Rochester, MN (US); Richard Martin Graybill, Urbana, IL (US); Yi Xu, Urbana, IL (US); Steven Doonan, Savoy, IL (US)

(73) Assignees: The Board of Trustees of the University of Illinois, Urbana, IL (US); Mayo Foundation for Medical Education and Research, Rochester, MN (US)

( * ) Notice: Subject to any disclaimer, the term of this patent is extended or adjusted under 35 U.S.C. 154(b) by 340 days.

(21) Appl. No.: 15/121,667

(22) PCT Filed: Mar. 3, 2015

(86) PCT No.: PCT/US2015/018522
§ 371 (c)(1),
(2) Date: Aug. 25, 2016

(87) PCT Pub. No.: WO2015/134523
PCT Pub. Date: Sep. 11, 2015

(65) Prior Publication Data
US 2016/0362724 A1 Dec. 15, 2016

Related U.S. Application Data

(60) Provisional application No. 61/947,415, filed on Mar. 3, 2014.

(51) Int. Cl.
*C12Q 1/68* (2018.01)
*C12Q 1/6806* (2018.01)
*B01L 3/00* (2006.01)
*C12Q 1/686* (2018.01)
*C12Q 1/6844* (2018.01)
*C12Q 1/6869* (2018.01)

(52) U.S. Cl.
CPC ...... *C12Q 1/6806* (2013.01); *B01L 3/502784* (2013.01); *C12Q 1/686* (2013.01); *B01L 2200/0673* (2013.01); *B01L 2300/0867* (2013.01); *C12Q 1/6844* (2013.01); *C12Q 1/6869* (2013.01)

(58) Field of Classification Search
None
See application file for complete search history.

(56) References Cited

U.S. PATENT DOCUMENTS

| 8,093,064 B2 | 1/2012 | Shah et al. | |
|---|---|---|---|
| 2005/0069931 A1 | 3/2005 | Allis et al. | |
| 2012/0244532 A1* | 9/2012 | Craighead | B01L 3/502761 435/6.11 |
| 2013/0028812 A1 | 1/2013 | Prieto et al. | |

FOREIGN PATENT DOCUMENTS

WO   WO-2013134261 A1 *   9/2013   ........... C12Q 1/6869

OTHER PUBLICATIONS

Abate et al., High-throughput injection with microfluidics using picoinjectors. Proceedings of the National Academy of Sciences. 2010; 107(45):19163-6.
Acevedo et al., Genome-scale ChIP-chip analysis using 10,000 human cells. BioTechniques. 2007;43:791-7.
Anna et al., Formation of dispersions using "flow focusing" in microchannels. Appl Phys Lett. 2003; 82(3):364-6.
Bannister AJ, Kouzarides T. Regulation of chromatin by histone modifications. Cell research. 2011; 21(3):381-95.
Baylin SB, Jones PA. A decade of exploring the cancer epigenome—biological and translational implications. Nat Rev Cancer. 2011; 11(10):726-34.
Bonasio et al., Molecular signals of epigenetic states. Science. 2010; 330(6004):612-6.
Carey et al., Chromatin Immunoprecipitation (ChIP). Cold Spring Harbor Protocols. 2009;2009(9):pdb.prot5279.
Chan IS, Ginsburg GS. Personalized medicine: progress and promise. Annu Rev Genomics Hum Genet. 2011; 12:217-44.
Dahl JA, Collas P. Q2ChIP, a Quick and Quantitative Chromatin Immunoprecipitation Assay, Unravels Epigenetic Dynamics of Developmentally Regulated Genes in Human Carcinoma Cells. Stem Cells. 2007,;25(4):1037-46.
Dahl JA, Collas P. A rapid micro chromatin immunoprecipitation assay (mChIP). Nat Protoc. 2008; 3(6):1032-45.
Dahl JA, Collas P. μChIP—a rapid micro chromatin immunoprecipitation assay for small cell samples and biopsies. Nucleic Acids Res. 2008,;36(3):e15.

(Continued)

*Primary Examiner* — Suryaprabha Chunduru
(74) *Attorney, Agent, or Firm* — Klarquist Sparkman LLP

(57) ABSTRACT

This application provides fluidic devices, such as microfluidic devices, which can be used for the creation and/or manipulation of droplets in droplet-based microfluidic systems, as well as systems and methods for using the same. The microfluidic devices can be used to generate droplets, extract or inject volume to droplets, and/or split droplets. Also provided are methods for generating nucleosomes, and isolated DNA from nucleosomes (or from non-nucleosomes), for example using the disclosed devices.

13 Claims, 26 Drawing Sheets

(56) References Cited

OTHER PUBLICATIONS

Dulac C. Brain function and chromatin plasticity. Nature. 2010; 465(7299):728-35.
Edd et al., Controlled encapsulation of single-cells into monodisperse picolitre drops. Lab Chip. 2008;8(8):1262-4.
Feinberg et al., Personalized epigenomic signatures that are stable over time and covary with body mass index. Sci Transl Med. 2010; 2(49):49ra67.
Feng et al., Using MACS to identify peaks from ChIP-Seq data. Curr Protoc Bioinformatics. 2011;Chapter 2:Unit 2 14.
Flanagin et al., Microplate-based chromatin immunoprecipitation method, Matrix ChIP: a platform to study signaling of complex genomic events. Nucleic Acids Res. 2008;36(3):e17.
Frenz et al., Reliable microfluidic on-chip incubation of droplets in delay-lines. Lab Chip. 2009; 9(10):1344-8.
Garmire et al., A global clustering algorithm to identify long intergenic non-coding RNA—with applications in mouse macrophages. PLoS One. 2011; 6(9):e24051.
Geng et al., Histone modification analysis by chromatin immunoprecipitation from a low number of cells on a microfluidic platform. Lab Chip. 2011; 11(17):2842-8.
Griewank et al., Genetic alterations and personalized medicine in melanoma: progress and future prospects. Journal of the National Cancer Institute. 2014; 106(2):djt435.
Grzenda et al., Polycomb and the emerging epigenetics of pancreatic cancer. J Gastrointest Cancer. 2011; 42(2):100-11. PMID: 21336826.
He et al., Selective Encapsulation of Single Cells and Subcellular Organelles into Picoliter- and Femtoliter-Volume Droplets. Anal Chem. 2005; 77(6):1539-44.
Hnisz et al., Super-enhancers in the control of cell identity and disease. Cell. 2013;155(4):934-47.
Issa JP. Aging and epigenetic drift: a vicious cycle. J Clin Invest. 2014; 124(1):24-9.
Joensson et al., Droplet Microfluidics—A Tool for Single-Cell Analysis. Angew Chem, Int Ed. 2012; 51(49):12176-92.
Kemna et al., High-yield cell ordering and deterministic cell-in-droplet encapsulation using Dean flow in a curved microchannel. Lab Chip. 2012; 12(16):2881-7.
Lee et al., Continuous-flow in-droplet magnetic particle separation in a droplet-based microfluidic platform. Microfluid Nanofluid. 2012; 13(4):613-23.
Lomberk et al.,The Heterochromatin Protein 1 family. Genome biology. 2006; 7(7):228.
Luger et al., Crystal structure of the nucleosome core particle at 2.8 A resolution. Nature. 1997; 389(6648):251-60.
Marjanovic et al.,. Cell plasticity and heterogeneity in cancer. Clin Chem. 2013; 59(1):168-79. Epub Dec. 12, 2012. doi: 10.1373/clinchem.2012.184655. PubMed PMID: 23220226.
Matsuoka et al., Micro- and nanofluidic technologies for epigenetic profiling. Biomicrofluidics. 2013;7(4):-.
Nelson et al.,Fast chromatin immunoprecipitation assay. Nucleic Acids Res. 2006;34(1):e2.
O'Donovan et al., Electrode-free picoinjection of microfluidic drops. Lab Chip. 2012;12(20):4029-32.
Oh et al., DNA-Enrichment Microfluidic Chip for Chromatin Immunoprecipitation. Anal Chem. 2009; 81(8):2832-9.
O'Neill et al., Epigenetic characterization of the early embryo with a chromatin immunoprecipitation protocol applicable to small cell populations. Nat Genet. 2006; 38(7):835-41.
Ordog et al., Epigenetics and chromatin dynamics: a review and a paradigm for functional disorders. Neurogastroenterol Motil. 2012; 24(12):1054-68. PMID: 23095056.
Platt et al., Analysis of chromatin organization by deep sequencing technologies. Methods Mol Biol. 2013;983:173-83.
Reik et al., Epigenetic reprogramming in mammalian development. Science. 2001; 293(5532):1089-93.
Roach et al., Controlling Nonspecific Protein Adsorption in a Plug-Based Microfluidic System by Controlling Interfacial Chemistry Using Fluorous-Phase Surfactants. Anal Chem. 2004; 77(3):785-96.
Roychowdhury et al., Personalized oncology through integrative high-throughput sequencing: a pilot study. Sci Transl Med. 2011; 3(111):111ra21.
Shilatifard A. The COMPASS family of histone H3K4 methylases: mechanisms of regulation in development and disease pathogenesis. Annu Rev Biochem. 2012; 81:65-95.
Simon JA, Kingston RE. Occupying chromatin: Polycomb mechanisms for getting to genomic targets, stopping transcriptional traffic, and staying put. Molecular cell. 2013;49(5):808-24.
Song et al., Reactions in Droplets in Microfluidic Channels. Angew Chem, Int Ed. 2006; 45(44):7336-56.
Tice et al., Formation of Droplets and Mixing in Multiphase Microfluidics at Low Values of the Reynolds and the Capillary Numbers. Langmuir. 2003; 19(22):9127-33.
Tran et al., From tubes to drops: droplet-based microfluidics for ultrahigh-throughput biology. J Phys D: Appl Phys. 2013;46(11):114004.
Urrutia R. KRAB-containing zinc-finger repressor proteins. Genome biology. 2003; 4(10):231.
Whyte et al., Master transcription factors and mediator establish super-enhancers at key cell identity genes. Cell. 2013; 153(2):307-19.
Wu et al., Automated microfluidic chromatin immunoprecipitation from 2,000 cells. Lab Chip. 2009; 9(10):1365-70.
Wu et al., High throughput automated chromatin immunoprecipitation as a platform for drug screening and antibody validation. Lab Chip. 2012; 12(12):2190-8.
PCTUS2015018522 International Preliminary Report on Patentability dated Sep. 6, 2016 (9 pages).
Ding et al., "'V-junction': a novel structure for high-speed generation of bespoke droplet flows," Analyst, The Royal Society of Chemistry, 2014.
Fallah-Araghi et al., "A completely in vitro ultrahigh-throughput droplet-based microfluidic screening system for protein engineering and directed evolution," Lab Chip 12:882-891, 2012.
Lin et al., "Novel on-demand droplet generation for selective fluid sample extraction," Biomicrofluidics 6:024103, 2012.
Oreskovic et al., "Microfluidic Chromatin Immunoprecipitation in Nanoliter-Scale Droplets," Biomedical Engineering Society Annual Meeting Oct. 22-25, 2014.
Pei et al., "Parallel Electrophoretic Analysis of Segmented Samples on Chip for High-Throughput Determination of Enzyme Activities," Anal Chem. 82:9261-9267, 2010.
Roman et al., "Sampling and Electrophoretic Analysis of Segmented Flow Streams Using Virtual Walls in a Microfluidic Device," Anal Chem. 80: 8231-8238, 2008.
Teste et al., "Chromatin Immunoprecipitation in Droplets: Toward Fast and Cheap Analyses," Abstract from 18th International Conference on Miniaturized Systems for Chemistry and Life Sciences, Oct. 26-30, 2014, San Antonio, Texas.
PCTUS2015018522 Written Opinion dated Jun. 3, 2015 (8 pages).
PCTUS2015018522 International Search Report dated Jun. 3, 2015 (3 pages).

* cited by examiner

FIG. 4A
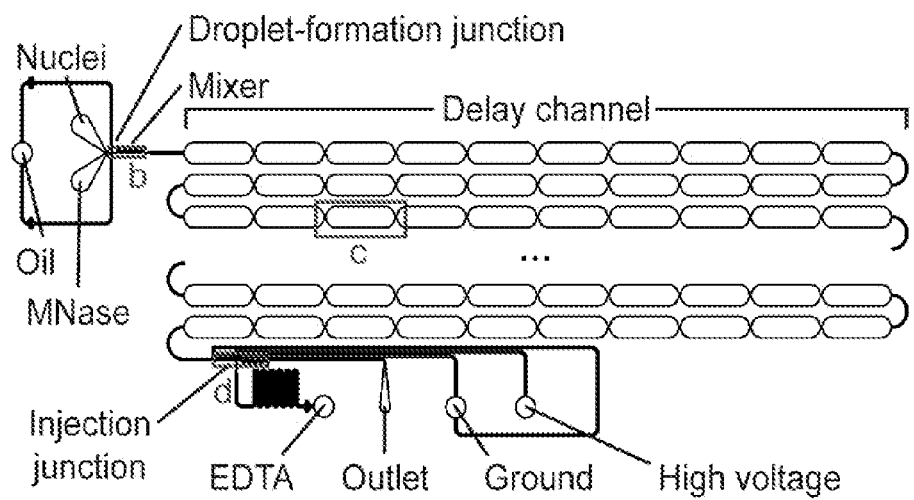
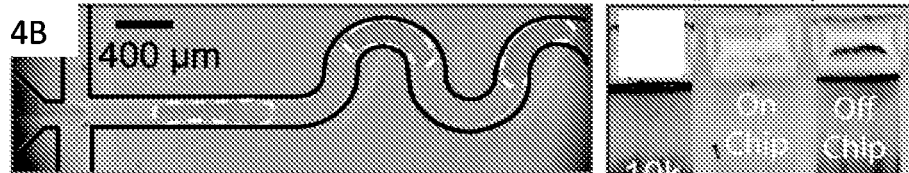
FIG. 4B
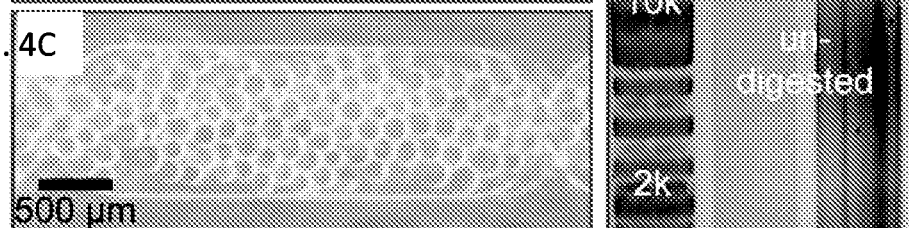
FIG. 4C
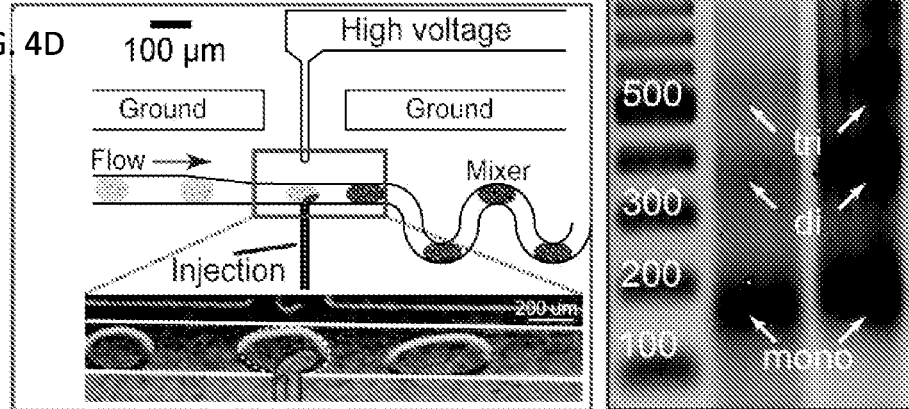
FIG. 4D
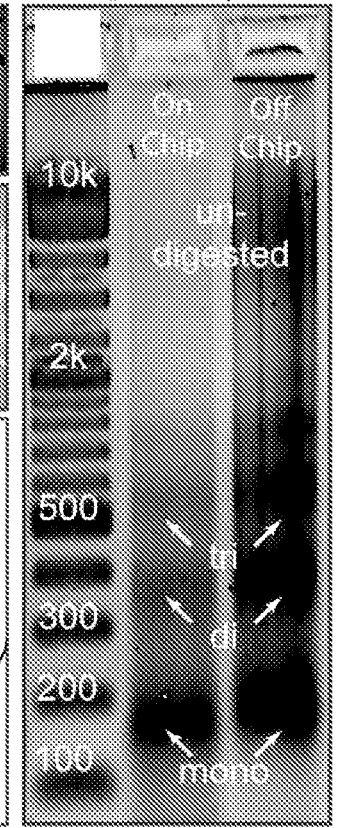
FIG. 4E

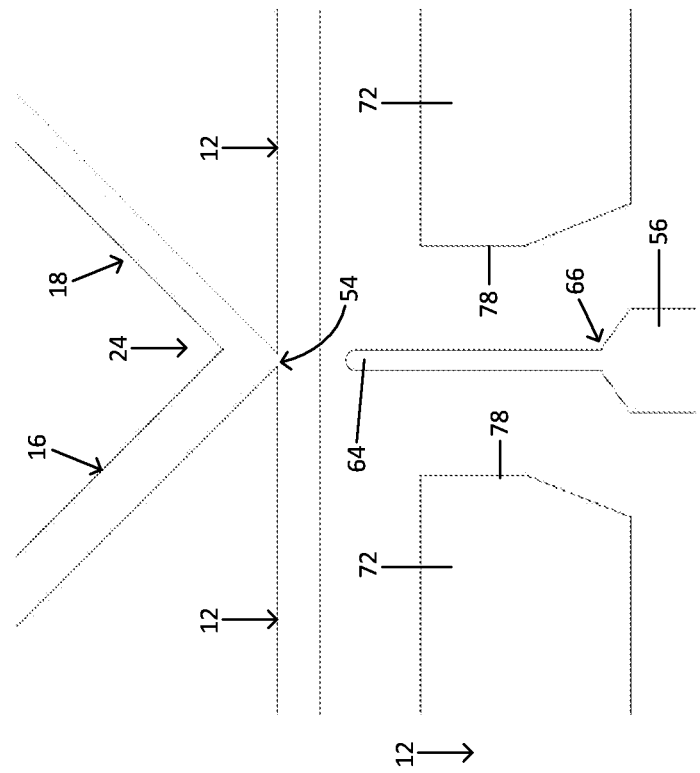
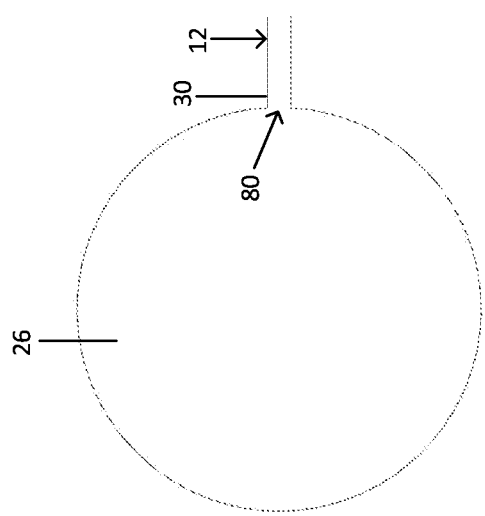

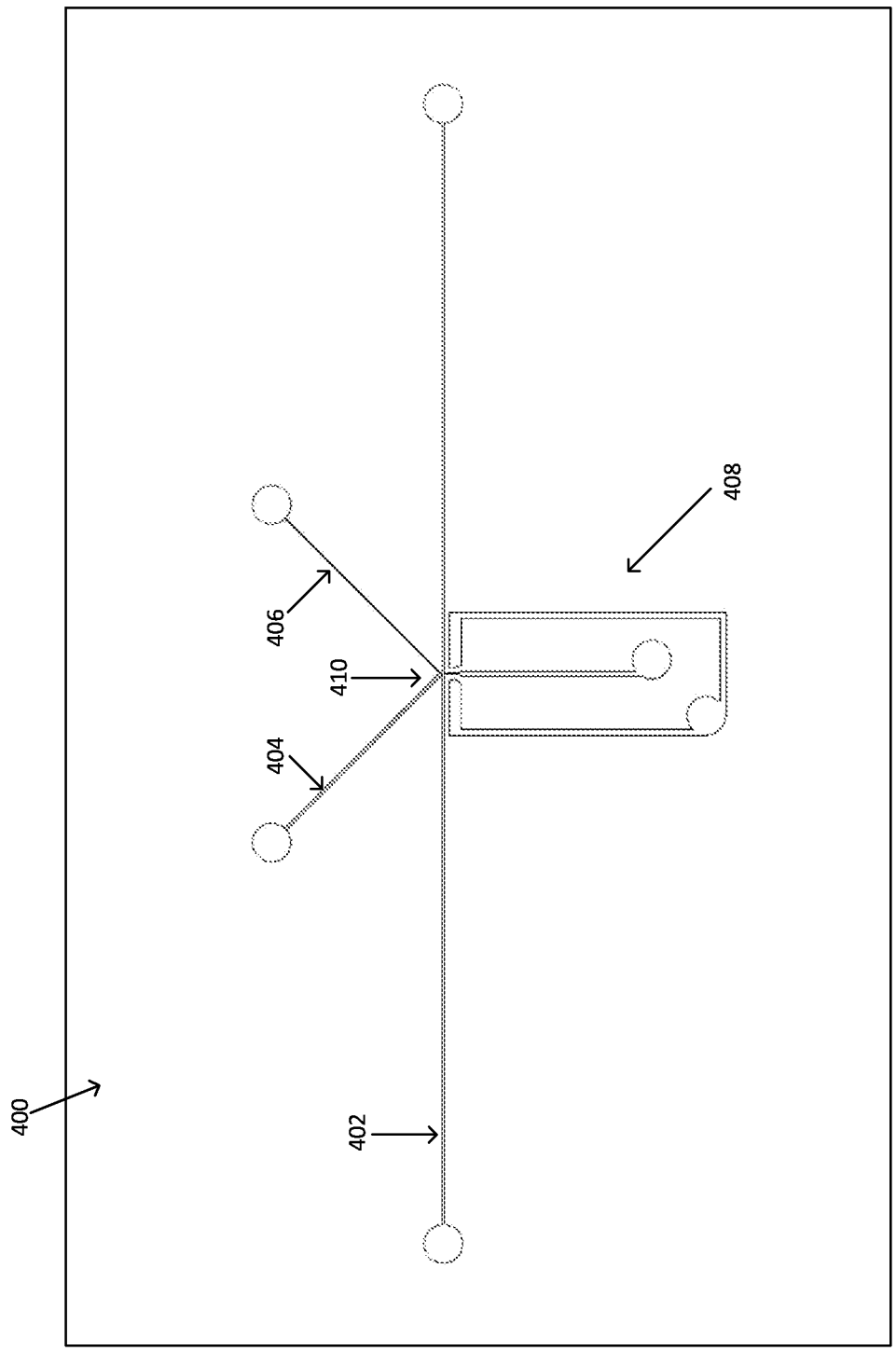

CHROMATIN IMMUNOCAPTURE DEVICES AND METHODS OF USE

CROSS REFERENCE TO RELATED APPLICATION

This application is the U.S. National Stage of International Application No. PCT/US2015/018522 filed Mar. 3, 2015, which was published in English under PCT Article 21(2), which in turn claims priority to U.S. Provisional Application No. 61/947,415 filed Mar. 3, 2014, both herein incorporated by reference.

FIELD

This application provides fluidic devices that can be used to prepare and analyze nucleosomes, as well as methods of analyzing nucleosomes and their associated nucleic acids.

BACKGROUND

Epigenetic control of gene transcription, DNA synthesis and repair plays critical roles in the specification of cell fate and function, aging and carcinogenesis. Accessibility of the genome for these DNA-templated tasks depends on the distribution of nucleosomes, the fundamental repeating unit of chromatin composed of histone proteins and associated DNA. Nucleosome configuration is in turn regulated by a complex interplay among transcription factors, noncoding RNA, post-synthetic DNA and histone modifications, histone variants, and non-histone proteins that write, erase, and interpret chromatin-associated signals. Chromatin immunoprecipitation (ChIP) is the gold standard for probing protein-DNA interactions and is increasingly used in research aiming to identify molecular targets for individualized therapy (e.g., in cancer). In currently available ChIP assays, antibodies targeting specific chromatin components are used to purify fragmented DNA-protein complexes. The pendant DNA is then released and analyzed by qPCR or sequencing.

While powerful, traditional ChIP protocols require a large cellular input ($10^6$-$10^7$ cells), which limits their utility to study biopsies, rare cells (e.g., stem cells, circulating tumor cells), and to assess tumor heterogeneity. ChIP is also laborious, time-consuming, and highly influenced by user skills Recent advances in ChIP technologies including a handful of approaches utilize multi-layered, valved microfluidic devices, offer reduced sample sizes, increased parallelization, and the potential for automation. However, no single approach simultaneously offers these benefits. Furthermore, the published methods did not allow rigorous, genome-wide validation due to lack of scalability. Exemplary desirable improvements include a more comprehensive incorporation of the entire ChIP workflow, amenability to variable levels of cellular input, and on-chip processing that readily interfaces with downstream genomic analyses.

SUMMARY

The present disclosure provides technology that leverages droplet microfluidics to perform automated epigenetic analyses from single cells per droplet and comprehensively allows for highly controlled chromatin processing, immunocapture, and recovery of nucleosome DNA for analysis, for example by PCR (such as qPCR) and/or sequencing. The use of aqueous droplets, which are encapsulated by an immiscible oil phase and thus do not touch the walls of the device, greatly reduces sample loss. Furthermore, the disclosed devices are capable of handling virtually any input from single cells to the inputs used in conventional ChIP by operating for different periods of time, permitting genome-wide validation. This platform enables rigorous epigenetic studies to be performed at single-cell resolution (or cellular materials can be pooled) in a highly automated and parallel manner, thus providing insights into cancer biology and serving as a tool for personalized cancer diagnosis and therapy. Although this disclosure provides specific examples of application of this technology to ChIP analysis of single cells, one skilled in the art will appreciate that this technology can be used for other types of epigenetic analysis (such as at the single-cell level), such as indexing-first chromatin immunoprecipitation (iChIP), methyl-CpG-binding domain protein-based capture, methylated DNA immunoprecipitation, hydroxymethylated DNA immunoprecipitation, DNase hypersensitivity assay, micrococcal nuclease (MNase)-based nucleosome positioning assay, assay for transposase-accessible chromatin, and the like.

The present disclosure provides a droplet microfluidic devices and platforms for the enzymatic processing of single nuclei into nucleosomes (such as mono-, di-, and trinucleosomes), solid-phase-based chromatin immunocapture and purification of chromatin-associated DNA from nucleosomes derived from single cells, or both, suitable for gene-targeted or genome-wide chromatin analysis. The resultant mono-, di- or trinucleosome preparations are also suitable for detecting the association with specific DNA sequences of transcription factors that bind either to nucleosome-associated DNA or DNA located between nucleosomes and left intact by the nuclease treatment. In one example, the device is referred to as a nanoliter-scale chromatin immunocapture (nChIC) device. The disclosed microfluidic devices can be used for the creation and/or manipulation of droplets in droplet-based microfluidic systems. The microfluidic devices can be used to generate droplets, extract or inject volume to droplets, and/or split droplets. The disclosed devices can include electrode channels for droplet destabilization and manipulation.

In some examples, the device includes a main microchannel and at least two other microchannels. The main microchannel defines a main fluid flow path and has an opening, and first and second microchannels defining a first and second fluid flow paths, respectively. The first fluid flow path is in fluidic communication with the main fluid flow path via the opening and forms a first angle relative to the main microchannel less than 90 degrees. The second microchannel defines a second fluid flow path in fluidic communication with the main fluid flow path via the opening and in fluidic communication with the first fluid flow path. The second microchannel forms a second angle relative to the main microchannel less than 90 degrees. The first and second microchannels form a third angle relative to one another, with the third angle being between 60 and 135 degrees.

In some examples, the device includes one or more fluid control members to alter fluid flow and/or pressure in the flow paths. A main fluid control member can be configured to control the flow of a first fluid in the main fluid flow path and at least one additional fluid control member configured to control the flow of a second fluid in the first and second fluid flow paths. In other embodiments, an electric field generator is positioned adjacent the main fluid flow path at the location of the opening.

Also provided are methods for using the device, for example for manipulating droplets in microfluidics system is provided. The method can include delivering a plurality of droplets and a first fluid through a main fluid flow path of a main microchannel and delivering a second fluid through along a side flow path defined by intersecting first and second microchannels. The first and second microchannels can form an angle therebetween and intersect with one another at an opening in the main microchannel. The method can include altering a volume of one or more of the plurality of droplets as respective droplets move along the main fluid flow path and pass the opening in the main microchannel.

In some examples, the act of altering the volume of the one or more of the plurality of droplets includes removing a portion of the one or more droplets and directing the removed portion into the side flow path, and/or increasing the volume of the one or more droplets by injecting a fluid from the side flow path into the main fluid flow path. The relative directions of fluid in the main fluid flow path and the side flow path can vary. The first fluid can be delivered along the main fluid flow path in a first direction and second fluid is delivered along the side flow path in a second direction. At the intersection of the first and second microchannels the second direction can be generally parallel to the first direction or it can be opposite. In some embodiments, the method can include applying an electric field to the plurality of droplets adjacent to the opening in the main microchannel.

Also provided are methods that allow for nucleosome isolation, and in some examples analysis of DNA from the nucleosomes. Such methods can have one or more steps automated, such as all of the steps.

Automated methods of generating nucleosomes, such as mono, di-, and/or trinucleosomes, are provided. Such methods use eukaryotic cells as input and nucleosomes are the output. The resulting nucleosomes from a plurality of cells are pooled into an aqueous quench solution which stops or retards chromatin digestion. Such methods are useful for obtaining nucleosomes and interposed DNA quickly and in an automated way, wherein the resulting mon-, di- and trinucleosomes can be used for subsequent analysis, such as ChIP, variants of ChIP, DNase hypersensitivity or other assays analyzing the distribution of nucleosomes and associated chromatin regulator proteins and transcription factors. In some examples, such methods include encapsulating an aqueous solution comprising a cell suspension (wherein the cells can be crosslinked) and a lysing solution within a droplet, resulting in a single droplet containing a single cell. The droplet has an outer oil-containing layer, which is not miscible with the aqueous solution containing the cell. For example, the droplet can be formed by using an automated droplet-forming means. The cell within the droplet is then incubated under conditions that allow for lysis of the cell within the droplet. Subsequently, a non-nucleosome-cleaving nuclease solution is added to the droplet, thereby cleaving DNA in the droplet without substantially affecting portions of the DNA that interact with histones within the nucleosomes. The degree of cleavage of internucleosomal DNA can be titrated for optimal yields of mono-, di- and trinucleosomes and interposed DNA. For example, the non-nucleosome-cleaving nuclease solution can be added to the droplet by using an automated injection means, such as an injector and a means to apply a voltage (e.g., electric field generator) to the droplet, thereby allowing the non-nucleosome-cleaving nuclease solution to merge with the droplet. After allowing for an adequate amount of DNA digestion, a plurality of the droplets are automatedly moved or transferred to an aqueous quenching solution, under conditions that allow quenching of the non-nucleosome-cleaving nuclease. For example, the droplet can be moved or transferred to an aqueous quenching solution by using an automated means, such as a means to apply a voltage to the droplet (e.g., electric field generator), which allows the droplet to move to a different portion of the device. This results in the generation of a population of nucleosomes in an aqueous phase.

Methods of analyzing DNA associated with nucleosomes, such as from mono, di-, and/or trinucleosomes, are provided. Such methods can have one or more steps automated, and use eukaryotic cells as input and output a droplet containing nucleosomes DNA from a single cell. The DNA in the resulting droplets can be analyzed, thereby allowing single-cell epigenetic information to be obtained, for example allowing for single-cell PCR and/or sequencing analysis. In some examples, such methods include encapsulating an aqueous solution comprising a cell suspension (wherein the cells can be crosslinked) and a lysing solution within a droplet, resulting in a single droplet containing a single cell. The droplet has an outer oil-containing layer, which is not miscible with the aqueous solution containing the cell. For example, the droplet can be formed by using an automated droplet-forming means. The cell within the droplet is then incubated under conditions that allow for lysis of the cell within the droplet. Subsequently, a non-nucleosome-cleaving nuclease solution is added to the droplet, thereby cleaving DNA in the droplet without substantially affecting portions of the DNA that interact with histones within the nucleosomes. For example, the non-nucleosome-cleaving nuclease solution can be added to the droplet by using an automated injection means, such as an injector and a means to apply a voltage to the droplet (e.g., electric field generator), thereby allowing the non-nucleosome-cleaving nuclease solution to merge with the droplet. After allowing for an adequate amount of DNA digestion, which can be optimized for specific downstream applications (e.g., histone marks or chromatin regulator proteins associated with loosely or densely packaged chromatin, transcription factors, etc.), a quenching solution is added to the droplet, thereby quenching the non-nucleosome-cleaving nuclease. For example, the quenching solution can be added to the droplet by using an automated injection means, such as an injector and a means to apply a voltage to the droplet (e.g., electric field generator), thereby allowing the quenching solution to merge with the droplet. After allowing for an adequate amount of quenching, a solution containing a solid support comprising one or more binding reagents (e.g., can specifically bind to a component of the nucleosome) is added to the droplet. For example, the solid support containing solution can be added to the droplet by using an automated injection means, such as an injector and a means to apply a voltage to the droplet (e.g., electric field generator), thereby allowing the solid support containing solution to merge with the droplet. The solid support is incubated under conditions that allow it to bind to targets of the nucleosomes within the droplet. The solid support bound to the histones is then concentrated, and optionally washed, for example by using means that allow for concentration of the solid support (e.g., magnet, centrifugal forces, flow cytometry) and a means that allows for removal of part of the droplet (e.g., means to apply a voltage). An enzyme solution that can release the histones, nonhistone proteins, and DNA from the solid support is added to the resulting portion of the droplet containing the solid support. For example, the enzyme solution can be added to the droplet by using an automated injection means, such as an injector and a means to apply a voltage to the droplet (e.g., electric field generator), thereby allowing the enzyme solution to merge with the droplet. After allowing for an adequate amount of digestion, the droplet is separated into a portion containing the solid support and a portion containing the DNA, for example by using means that allow for concentration of the solid support (e.g., magnet, centrifugal forces, flow cytometry) and a means that allows for removal of part of the droplet (e.g., means to apply a voltage). In one example, the portion of the droplet containing the DNA is collected. The resulting nucleosome DNA from a single cell can then be purified and concentrated if desired, and analyzed (e.g., using PCR and/or sequencing). In another example (discussed in more detail in the paragraph below), the portion of the droplet containing the DNA is subsequently exposed to a solution containing a solid support comprising DNA capture reagents. For example, the solid support containing solution can be added to the droplet by using an automated injection means, such as an injector and a means to apply a voltage to the droplet (e.g., electric field generator), thereby allowing the solid support containing solution to merge with the droplet. The solid support is incubated under conditions that allow it to bind to DNA within the droplet. The solid support bound to the DNA is then concentrated, and optionally washed, for example by using means that allow for concentration of the solid support (e.g., magnet, centrifugal forces, flow cytometry) and a means that allows for removal of part of the droplet (e.g., means to apply a voltage). In some examples, a plurality of single cells within a plurality of single droplets are analyzed contemporaneously.

In some examples, after releasing the histones, nonhistone proteins, and DNA from the solid support, portion of the droplet containing the DNA is incubated with a second solid support that binds to the DNA, for example by using an automated injection means, such as an injector and a means to apply a voltage to the droplet (e.g., electric field generator), thereby allowing the second solid support containing solution to merge with the droplet. After allowing for an adequate amount of binding, the solid supports can be optionally washed, and the bound DNA eluted, and the solid supports separated from the eluted DNA (e.g., by using methods that allow for concentration of the second solid support (e.g., magnet, centrifugal forces, flow cytometry) and a means that allows for removal of part of the droplet (e.g., means to apply a voltage)). In one example, the portion of the droplet containing the DNA is collected. The resulting nucleosome DNA from a single cell can then be purified and concentrated if desired, and analyzed (e.g., using PCR and/or sequencing). In some examples, a plurality of single cells within a plurality of single droplets are analyzed contemporaneously.

In some examples, the step of collecting the portion of the droplet containing the DNA includes combining DNA from a plurality of droplets into a single solution, thereby generating a solution of nucleosome DNA from a plurality of cells. This pooled DNA can be purified and concentrated if desired, and analyzed (e.g., using PCR and/or sequencing).

In some examples, the step of encapsulating includes encapsulating a single cell within the droplet, and subsequently adding to the formed droplet a lysing solution, thereby lysing the cell within the droplet. In another example, the step of encapsulating includes adding a lysing solution to an aqueous solution containing a cell suspension, prior to forming the droplet.

In some examples, the steps that involve adding solutions/reagents to the droplet are achieved by destabilizing the droplet with a high voltage (HV) field.

In some examples, the single cell within a droplet is present in a curved or serpentine microchannel, such as one that is about 20 to 100 μm in diameter. In some examples, all of the steps of nucleosome preparation, immunoprecipitation, and DNA separation from the solid support, take place in the droplet, such that the cell and its contents do not touch the wall of a microchannel in which the droplet is located. For example, the cell and its contents are not anchored or attached to the microchannel.

Any eukaryotic cell can be analyzed with the disclosed devices and methods. In one example the eukaryotic cell is a human cell, invertebrate cell, amphibian cell, bird cell, plant cell, yeast cell or protozoan cell including a cancer cell or cancer stem cell.

The methods allow for a dynamic input, that is, the devices and methods allow for analysis of any number of cells and any size cells. For example, if the sample to be analyzed contains high number of cells, the method and device can be run for longer periods of time. In addition, the droplet formation can be adapted to any size of cell to be analyzed.

The disclosed methods can be performed on the disclosed devices.

The foregoing and other objects and features of the disclosure will become more apparent from the following detailed description, which proceeds with reference to the accompanying figures.

BRIEF DESCRIPTION OF THE DRAWINGS

FIGS. 4A-4E show a device for on-chip MNase processing of crosslinked nuclei into nucleosomes. (A) Schematic illustration of an exemplary device (B) representative droplet formation, (C) a delay channel network to facilitate a controlled droplet transit time of 10 minutes, before the (D) electrode-free injection of an EDTA solution to quench the reaction. (E) Gel electrophoresis analysis comparing on- and off-chip MNase processing of mono+di+trinucleosomes. Identical input was utilized in both on- and off-chip processing and the on-chip processing clearly shows less undigested chromatin.

FIGS. 6B-6C are various detail views of the microfluidic device.

FIG. 19 is a schematic of a microfluidic device, according to another embodiment.

DETAILED DESCRIPTION

Figure 1A:
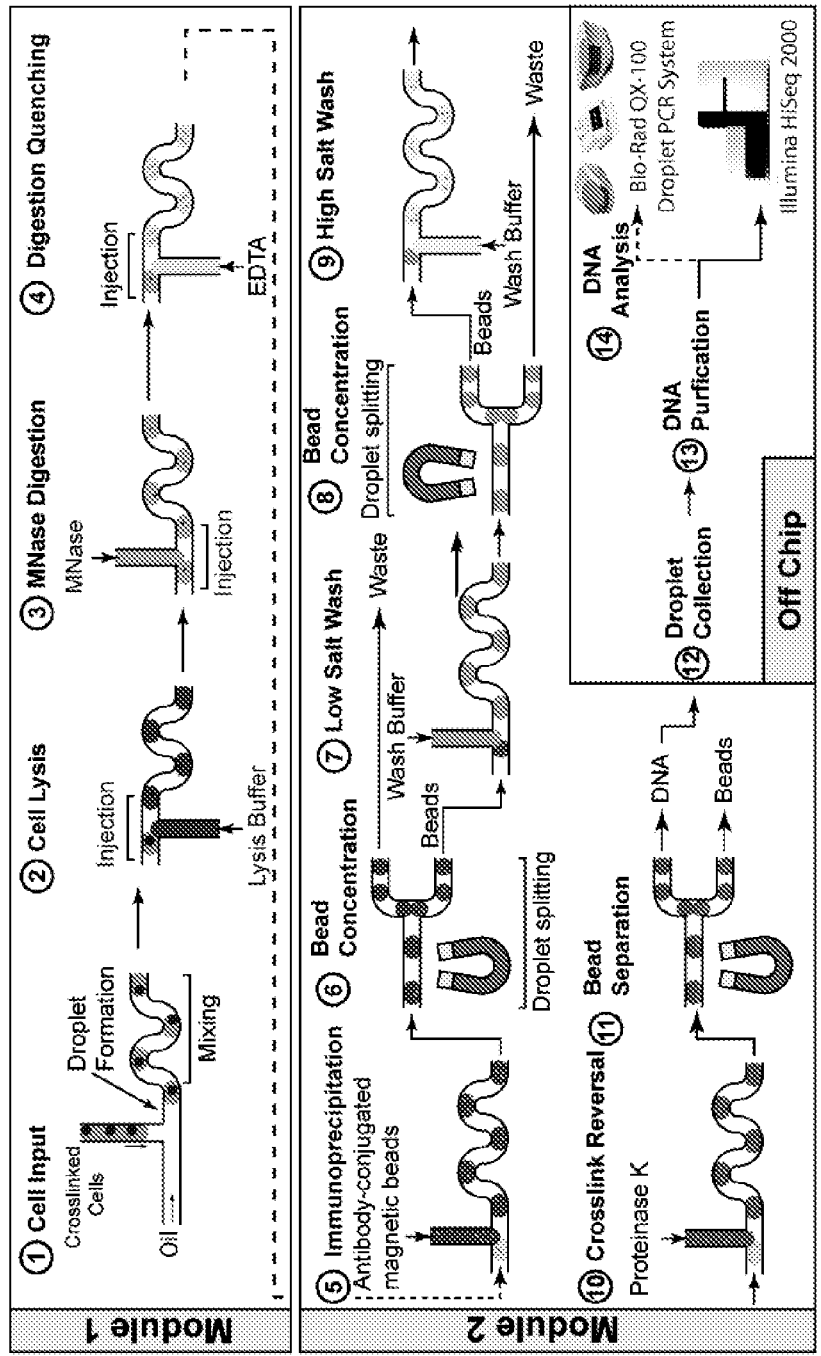
FIGS. 1A-1D are schematic drawings showing an overview of exemplary methods. (A) An automated single-cell method for analyzing DNA from nucleosomes. Module 1 includes encapsulation of single cells into droplets, sequential injection of lysis buffer and MNase (or other nuclease), followed by the downstream injection of a quencher (e.g., EDTA). Module 2 includes the immunocapture of nucleosomes using exemplary antibody-modified magnetic beads, bead washing, DNA release, and purification. The last part of Step 2 analyzes the captured DNA using qPCR and sequencing. This provides the capability to probe immunocaptured DNA from single cells by directly injecting PCR reagents into single droplets for ddPCR analysis. (B) An automated bulk method for analyzing DNA from nucleosomes, wherein DNA from nucleosomes is isolated from single cells, and then pooled. Module 1 includes encapsulation of single cells into droplets, sequential injection of lysis buffer and MNase (or other nuclease), followed by the downstream injection of a quencher (e.g., EDTA). Module 2 includes the immunocapture of nucleosomes using exemplary antibody-modified magnetic beads, bead washing, and DNA release, followed by extraction of the DNA into an aqueous phase. The last part of Step 2 analyzes the DNA, for example using PCR and/or sequencing. This strategy saves the manual step of droplet breaking at the end of the process. This embodiment can be used clinically as it automates the entire process, thus requiring fewer cells than standard methods. (C) An automated method for obtaining nucleosomes from single cells, wherein the generated nucleosomes are pooled into an aqueous phase. The resulting nucleosomes can be analyzed by known epigenetic analysis methods. (D) An automated single-cell method for analyzing DNA from nucleosomes. This is a variant of FIG. 1A, wherein following immunoprecipitation of nucleosomes, the associated DNA is captured using a solid support that binds DNA (step 7), and the DNA eluted (step 10). This provides the capability to probe immunocaptured DNA from single cells by directly injecting PCR reagents into single droplets for ddPCR analysis.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. Whenever a range is given, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein. All art-known functional equivalents, of any such materials and methods are intended to be included in this disclosure. All references including journal articles, patents, and patent applications cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided:

Administration: To provide or give a subject an agent, such as a chemotherapeutic or biologic, by any effective route. Exemplary routes of administration include, but are not limited to, oral, injection (such as subcutaneous, intramuscular, intradermal, intraperitoneal, intravenous, and intratumoral), sublingual, rectal, transdermal, intranasal, vaginal and inhalation routes. For example, following analysis of a cell from a subject using the disclosed methods, the subject may be administered an appropriate therapy based on the results.

Antibody (Ab): A polypeptide that includes at least a light chain or heavy chain immunoglobulin variable region and specifically binds an epitope of an antigen (such as a target agent). Antibodies include monoclonal antibodies, polyclonal antibodies, chimeric antibodies, or fragments of antibodies as well as others known in the art. In some examples, an antibody is specific for a target agent, such as a histone protein (e.g., H2A, H2B, H3, or H4) or covalent modification thereof or a transcription factor, and thus can be used in the methods provided herein.

Antibodies are composed of a heavy and a light chain, each of which has a variable region, termed the variable heavy (VH) region and the variable light (VL) region. Together, the VH region and the VL region are responsible for binding the antigen recognized by the antibody. This includes intact immunoglobulins and the variants and portions of them well known in the art, such as Fab' fragments, F(ab)'2 fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes single-chain antibodies such as $V_HH$ fragments from camelids and $V_{NAR}$ fragments from cartilaginous fishes, as well as recombinant forms such as chimeric antibodies (for example, humanized murine antibodies) and heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

A "monoclonal antibody" is an antibody produced by a single clone of B lymphocytes or by a cell into which the light and heavy chain genes of a single antibody have been transfected. Monoclonal antibodies are produced by methods known to those of ordinary skill in the art, for instance by making hybrid antibody-forming cells from a fusion of myeloma cells with immune spleen cells. These fused cells and their progeny are termed "hybridomas." Monoclonal antibodies include humanized monoclonal antibodies.

Chromatin immunoprecipitation (ChIP): A method that involves immunoprecipitation and can be used to investigate the interaction between proteins and DNA in a cell, for example to determine whether specific proteins are associated with specific genomic regions, such as histones, histone variants, histone modifications, chromatin regulators ('readers', 'writers' and 'erasers' of histone modifications) and transcription factors on promoters, enhancers, gene bodies or other DNA sequences. The term also covers variant methods wherein covalent modifications of DNA or RNA bases including, but not limited to, methylated, hydroxymethylated, formylated and carboxylated cytosine or the 'readers', 'writers' and 'erasers' of these modifications, are detected. Such methods can be used to determine the specific location in the genome that various histone modifications are associated with, indicating the target of the histone modifiers. Exemplary limitations to currently available ChIP methods include the requirement for a large amount of cellular input (input is lost during the numerous steps required), and it is laborious and time-consuming.

Coding sequence: The part of a gene or cDNA which codes for the amino acid sequence of a protein, or for a functional RNA such as a tRNA or rRNA.

Complement or complementary sequence: A sequence of nucleotides which forms a hydrogen-bonded duplex with another sequence of nucleotides according to Watson-Crick base-pairing rules. For example, the complementary base sequence for 5'-AAGGCT-3' is 3'-TTCCGA-5'.

Connected: Generally means that joined or linked such that there is fluidic communication between the elements and does not exclude the presence of intermediate elements between connected items, absent specific contrary language.

Detect: To determine if a particular agent is present or absent, and in some example further includes quantification of the agent if detected.

Downstream: A relative position in a nucleic acid molecule, such as DNA or RNA, and is the region towards the 3' end of a strand.

Epigenetics: Cellular and physiological traits that are heritable by daughter cells and not caused by changes in the DNA sequence, and includes stable, long-term alterations in the transcriptional potential of a cell. Examples of mechanisms that produce such changes include but are not limited to, DNA methylation and histone modifications. Gene expression can be controlled through the action of repressor proteins that attach to silencer regions of the DNA. These epigenetic changes may last through cell divisions for the duration of the cell's life, and may also last for multiple generations even though they do not involve changes in the underlying DNA sequence of the organism.

Epigenetics can be used to diagnose diseases or to determine what drugs/treatments will work best. Examples of epigenetic changes found in some cancers include:

| Cancer | Gene | Epigenetic change |
|---|---|---|
| Breast | BRCA1 | CpG island methylation |
| | WRN | CpG island methylation |
| | WRN | CpG island methylation |
| Ovarian | BRCA1 | CpG island methylation |
| | FANCF | CpG island methylation |
| | RAD51C | CpG island methylation |
| | MGMT | CpG island methylation |
| | WRN | CpG island methylation |
| Colorectal | MLH1 | CpG island methylation |
| | MSH2 | CpG island methylation |
| | ERCC1 | epigenetic type unknown |
| | Xpf | epigenetic type unknown |
| Head and neck | MGMT | CpG island methylation |
| | MLH1 | CpG island methylation |
| | NEIL1 | CpG island methylation |
| | FANCB | CpG island methylation |
| | MSH4 | CpG island methylation |
| | ATM | CpG island methylation |

In addition, some prostate cancers have hypermethylation, resulting in lower gene expression (GSTP1). Other types of epigenetic changes include altered histone acetylation, histone methylation, nucleosome spacing and expression of noncoding RNA species including all RNA types that are not translated into proteins or act as ribosomal components or transfer RNA. These changes may arise from mutations in genes encoding epigenetic regulators or histone proteins, environmentally-dictated dysregulated expression of chromatin regulators especially in non-malignant diseases, as well as abnormal regulation of chromatin regulators by altered cellular signaling.

Expression: The process by which the coded information of a nucleic acid molecule, is converted into an operational, non-operational, or structural part of a cell, such as the synthesis of a protein. Expression of a gene can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule or protein can be altered relative to a normal (wild type) nucleic acid molecule or protein. Alterations in gene expression, such as differential expression, include but are not limited to: (1) overexpression (e.g., upregulation); (2) underexpression (e.g., downregulation); or (3) silencing of expression. Alterations in the expression of a nucleic acid molecule can be associated with, and in fact cause, a change in expression of the corresponding protein, for example relative to a normal control.

Controls or standards for comparison to a sample, for the determination of differential expression, include samples believed to be normal (in that they are not altered for the desired characteristic, for example a normal subject) as well as laboratory values, even though possibly arbitrarily set, keeping in mind that such values can vary from laboratory to laboratory. Laboratory standards and values may be set based on a known or determined population value and can be supplied in the format of a graph or table that permits comparison of measured, experimentally determined values.

Histone: An alkaline protein found in eukaryotic cell nuclei that package and order into structural units called nucleosomes. They are the primary components of chromatin. Examples of histone proteins include H2A, H2B, H3, and H4.

Isolated: An "isolated" biological component (such as a cell, nucleosome, or nucleic acid molecule) has been substantially separated, produced apart from, or purified away from other biological components in the tissue or cell of the organism in which the component naturally occurs, such as other chromosomal and extrachromosomal DNA and RNA, and proteins. Cells which have been "isolated" thus include cells harvested or extracted from an organism, such as a human, by standard methods (e.g., blood draw, tissue biopsy). Nucleic acid molecules and proteins which have been "isolated" include nucleic acids and proteins purified by standard purification methods. The term also embraces nucleic acid molecules and proteins prepared by recombinant expression in a host cell as well as chemically synthesized nucleic acids. A purified or isolated cell, protein, nucleosome, or nucleic acid molecule can be at least 70%, at least 80%, at least 90%, at least 95%, at least 96%, at least 97%, at least 98%, or at least 99% pure.

Label: An agent capable of detection, for example by spectrophotometry, flow cytometry, or microscopy (such as light microscopy). For example, one or more labels can be attached to a cell, for example by using a labeled antibody or labeled nucleic acid probe, thereby permitting detection of proteins or nucleic acids in the cell. Exemplary labels include radioactive isotopes, fluorophores, ligands, chemiluminescent agents, haptens, enzymes, and combinations thereof.

Nucleic acid construct: A nucleic acid molecule isolated from a naturally occurring gene or which has been modified to contain segments of nucleic acid which are combined and juxtaposed in a manner which would not otherwise exist in nature.

Nucleic acid molecule: A single- or double-stranded linear polynucleotide containing either deoxyribonucleotides or ribonucleotides that are linked by 3'-5'-phosphodiester bonds.

Nucleosome: A basic unit of DNA packaging in eukaryotes, which includes a segment of DNA wound in sequence around eight histone protein cores. The nucleosome core particle is approximately 147 base pairs (bp) of DNA wrapped in 1.67 left-handed superhelical turns around a histone octamer consisting of 2 copies each of the core histones H2A, H2B, H3, and H4. Core particles are connected by stretches of linker DNA, which are up to about 90 bp long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. However, this term is also applicable to enhancer regions of DNA, which are not contiguous with the regulated DNA sequences but can be brought into the vicinity of the regulated sequences by looping of the DNA. Furthermore, noncoding RNA generated from regulatory DNA sequences may also control the function of DNA sequences located at various distances from their origin.

Polypeptide: A linear polymer of amino acids that are linked by peptide bonds.

Promoter: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. Promoters are generally 80-120 base pairs long and can be constitutive or inducible.

Recombinant: A recombinant nucleic acid molecule is one that has a sequence that is not naturally occurring or has a sequence that is made by an artificial combination of two otherwise separated segments of sequence. This artificial combination can be accomplished by routine methods, such as chemical synthesis or by the artificial manipulation of isolated segments of nucleic acids, such as by genetic engineering techniques. Similarly, a recombinant protein is one encoded for by a recombinant nucleic acid molecule. Similarly, a recombinant or transgenic cell is one that contains a recombinant nucleic acid molecule and expresses a recombinant protein.

Sample: Any biological specimen that may contain (or is known to contain or is suspected of containing) a target of interest can be used. Biological samples are usually obtained from a subject and can include genomic DNA, RNA (including mRNA), protein, or combinations thereof. Examples that can analyzed with the disclosed methods and devices include but are not limited to a tissue or tumor biopsy, fine needle aspirate, bronchoalveolar lavage, pleural fluid, spinal fluid, saliva, sputum, surgical specimen, lymph node fluid, ascites fluid, peripheral blood (such as serum or plasma), urine, saliva, buccal swab, and autopsy material. Techniques for acquisition of such samples are well known in the art (for example see Schluger et al. *J. Exp. Med.* 176:1327-33, 1992, for the collection of serum samples). Serum or other blood fractions can be prepared in the conventional manner. In a specific example the sample includes circulating tumor cells. In another specific example the sample includes cancer cells. In another specific example the sample includes stem cells.

Subject: An organism from which a sample can be obtained for analysis with the disclosed methods. Exemplary subjects include unicellular eukaryotes (e.g., yeast), plants, insects, reptiles, amphibians, and mammals, such as humans, non-human primates, pigs, sheep, cows, dogs, cats, rodents and the like, from which a biological sample can be obtained. In two non-limiting examples, a subject is a human subject or a murine subject. In some examples, the subject has or is suspected of having cancer and/or a metastasis.

Transduced and Transformed: A virus or vector or nucleic acid molecule "transduces" a cell when it transfers nucleic acid into the cell. A cell is "transformed" or "transfected" by a nucleic acid transduced into the cell when the DNA becomes stably replicated by the cell, either by incorporation of the nucleic acid into the cellular genome, or by episomal replication.

Numerous methods of transduction are known to those skilled in the art, such as: chemical methods (e.g., calcium-phosphate transfection), physical methods (e.g., electroporation, microinjection, particle bombardment), fusion (e.g., liposomes), receptor-mediated endocytosis (e.g., DNA-protein complexes, viral envelope/capsid-DNA complexes) and by biological infection by viruses such as recombinant viruses {Wolff, J. A., ed, Gene Therapeutics, Birkhauser, Boston, USA (1994)}. In the case of infection by retroviruses, the infecting retrovirus particles are absorbed by the target cells, resulting in reverse transcription of the retroviral RNA genome and integration of the resulting provirus into the cellular DNA.

Tumor: Tumors are abnormal growths which can be either malignant or benign, solid or liquid (for example, hematogenous). In some examples, cells are detected by using a sensor that includes a recognition molecule specific for a surface protein, such as a receptor on the surface of the cell. For example, antibodies specific for particular cells are known in the art. Usually, such antibodies recognize a surface protein expressed by the cell, such as a receptor.

Examples of hematological tumors that can be analyzed with the disclosed methods include, but are not limited to: leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (including low-, intermediate- and high-grade), multiple myeloma, Waldenström's macroglobulinemia, heavy chain disease, myelodysplastic syndrome, mantle cell lymphoma and myelodysplasia.

Examples of solid tumors, such as sarcomas and carcinomas, that can be analyzed with the disclosed methods include, but are not limited to: fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, gastrointestinal stromal tumor, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Upstream: A relative position in a nucleic acid molecule, such as DNA or RNA, and is the region towards the 5' end of a strand.

Vector: A nucleic acid molecule as introduced into a host cell, thereby producing a transformed host cell. A vector may include nucleic acid sequences that permit it to replicate in the host cell, such as an origin of replication. A vector may also include one or more coding sequences and/or selectable marker genes and other genetic elements known in the art. A vector can transduce, transform or infect a cell, thereby causing the cell to express nucleic acids and/or proteins other than those native to the cell. A vector optionally includes materials to aid in achieving entry of the nucleic acid into the cell, such as a viral particle, liposome, protein coating or the like. Common vectors include plasmid vectors and phage vectors.

Overview

DNA is compacted in cells by coiling around histones. Modifications to histones, such as methylation, can result in changes in gene expression. Epigenetic regulation of gene expression via histones plays a role in many cellular processes, such as stem cell differentiation and oncogenesis. Chromatin immunoprecipitation (ChIP) can be used to analyze protein-DNA interactions, including the coiling of DNA around histones.

Epigenomic tests are an emerging tool in the development of personalized cancer treatment strategies. Individualized oncology aims to make therapeutic decisions based on each person's unique genomic, molecular and clinical information (1), particularly when conventional, population-based treatments are unavailable or ineffective (2). Analysis of the cancer genome and transcriptome by genomic hybridization and massively parallel sequencing have become the personalized diagnostic methods of choice (2, 3). However, there is a role for the epigenome in development, aging, common diseases and cancer (4-9). The term 'epigenome' refers to the genome-wide collection and distribution of epigenetic regulators and their molecular footprints including transcription factors, noncoding RNA, post-synthetic DNA and histone modifications, histone variants and non-histone proteins, which collectively establish and maintain mitotically heritable phenotypic traits without changes in the DNA sequence (10, 11). These mechanisms control the accessibility of the genome for gene transcription, DNA synthesis, and repair by regulating the distribution of nucleosomes, the fundamental repeating units of chromatin that is composed of an octamer formed by two copies each of core histones H2A, H2B, H3 and H4, as well as 146-147 base pairs (bp) of DNA (12). Since epigenetic mechanisms establish cellular identities (13, 14), they are a source of biological information upon which individualized therapeutic decisions can be based.

One barrier to achieving this goal is the lack of a robust, cost-effective, and automated analysis of genomic localization of chromatin components and regulators that is not dependent on user skills, but is amenable to parallelization and to size-constrained samples such as tumor biopsies, cancer stem cells, and circulating tumor cells. There are additional barriers limiting the use of epigenomic data in individualized medicine. First, epigenomic analysis must deal with many different kinds of molecules—several classes of RNA, DNA and proteins with their many covalent modifications. Second, quantification of proteins requires more input material than analysis of nucleic acids. Third, molecular interactions carry critical information that cannot be revealed by analyzing individual chromatin components. Fourth, bulk tissue samples are not ideal for epigenetic studies since the results reflect several cell types possessing their own unique epigenomic signatures. This problem is particularly acute in the case of rare cells critical for cancer pathogenesis such as stem cells (15), necessitating their isolation that further limits input sizes. Finally, since microenvironmental influences also affect the epigenome, clinical testing is ideally be performed in cells obtained without intervening expansion in culture or as xenografts.

Chromatin immunoprecipitation (ChIP) has emerged as the method of choice for analyzing protein-DNA interactions (16). The basic method involves chemical crosslinking, fragmentation of chromatin into mono/di/trinucleosomes to ensure proper resolution of genomic localization, immunoprecipitation of the targeted components (e.g., transcription factors, histones, histone and DNA modifications, non-histone proteins), separation of bound antibodies, crosslinking reversal, isolation of the released DNA, and its analysis by quantitative (q)PCR or sequencing. A typical ChIP workflow (16) involves about 30 steps, takes at least 4 days, and requires $10^6$-$10^7$ cells as input. The high input (large number of cells) is required because a substantial amount of material is lost at each step due to nonspecific adsorption to plastic tubes and tips. The complicated protocol also makes conventional ChIP prone to user error. Due to these problems, ChIP is typically applied to cell lines or large pieces of bulk tissue, which limits its use in clinical applications. Recent advances in ChIP protocols have significantly reduced the input requirements and/or protocol time (17-24). However, these improved methods still require extensive manual sample handling.

Microfluidic devices offer benefits over traditional macroscale methods including reduced volume requirements, parallelization capability, and automated operation, which make them particularly well-suited to sample-constrained epigenetic analyses (25-29). Multilayered, valved microfluidic devices have been applied to the automated analysis of 2,000 cells (28) and used for screening ChIP antibodies in a multiplexed format (29). Peristaltically driven mixing/reaction loops were used for cell lysis, chromatin preparation, and bead-based immunocapture. Beads were manually removed from the device prior to DNA isolation and qPCR. Another strategy to perform ChIP on as few as 50 cells (30) used a valved, multilayered microfluidic device featuring a packed bed of antibody-modified beads that served as a filter to physically block cells prior to on-chip lysis and then as a nucleosome capture support. After capture, the beads were manually removed for the release of DNA and qPCR. These two designs demonstrated the potential of microfluidics for sample-limited ChIP; however, there is still need for improvement. A concern with both devices is sample loss due to non-specific adsorption on the walls. Additionally, one device utilized a fixed volume mixing ring that requires about 20% of the input material to be expelled upon the addition of additional reagents, thus further increasing input requirements. The second device avoided this problem, but it could only achieve very modest specific target enrichment. Furthermore, it requires optimization of the number of beads for different sizes of input, which complicates clinical utility and generality to variable input sizes.

Point-of-care devices capable of providing robust and automated epigenetic analyses from sample limited inputs have the potential to revolutionize individualized medicine. The disclosed platform is a novel combination of droplet microfluidic sample manipulations, which can replace macroscale ChIP protocols, and permit high throughput studies of epigenomic heterogeneity. The disclosed droplet microfluidic platforms are suited to automated and ultralow-input (i.e., single-cell) analyses due to intrinsically low sample loss and amenability to tunable input, which is in contrast to previous microfluidic approaches for which aspects of device design and operation are fundamentally tied to cell input. This technology can be used with individualized medicine by enabling cost-effective epigenetic testing to be routinely applied to very small and heterogeneous samples at the point of care.

The disclosed droplet microfluidics-based, nanoliter-scale Chromatin ImmunoCapture (nChIC) platforms described herein, can be used for individualized medicine applications. The devices and methods utilize droplet microfluidics (31-34), in which the biological targets (cells, nucleosomes, DNA) are encapsulated in nano- or picoliter volume drops surrounded by an immiscible oil. The droplets can (i) reduce non-specific sample loss—through the use of surfactants, the biological contents in the aqueous droplets do not come into contact with biofouling-prone polymer sidewalls (35); (ii) allow rapid mixing—droplets have natural internal fluid circulation leading to extremely rapid (msec-scale) mixing (36); (iii) allow single cell analytical capabilities-individual cells can be easily encapsulated and analyzed in single droplets (37-40); and (iv) indeterminate operation—in contrast to determinate microfluidics that have defined volumes devoted to specific assay steps, droplets can be continuously generated and manipulated over variable amounts of time, allowing the accommodation of any number of cells into the protocol without specifically optimizing the operational characteristics of the device for various input sizes. In short, variable cell inputs can be handled simply by operating the device for different periods of time. This attribute permits the rigorous evaluation of device performance genome-wide using conventional techniques, a critical issue in light of the highly variable chromatin compaction across the nucleus affecting sensitivity to fragmentation (41)—a consideration not adequately addressed in previous studies reporting microfluidic ChIP devices. (28-30)

The fully automated droplet microfluidic platforms provided herein integrates enzymatic chromatin processing, and in some examples also magnetic immunocapture, washing and DNA collection. Droplet encapsulation significantly reduces sample loss and rapid mixing allows for rapid and well-controlled sample processing and target recognition. In one example, every step in the workflow is automated prior to genetic analyses of the DNA. In some examples, the resulting generation of a droplet containing nucleosome DNA allows direct interfacing with droplet digital (dd)PCR for genetic analysis. In one example, the device permits genome-wide validation of performance by deep sequencing. The disclosed droplet microfluidic approach provides the opportunity to study epigenetic profiles of single cells (or populations of cells) allowing both the assessment of cell heterogeneity within complex clinical samples and the application of cost-effective epigenetic testing to very small samples in individualized medicine settings directly at the point of care.

Unlike other devices and methods, those disclosed are able to perform a complete ChIP workflow on single cells per droplet and allows direct interfacing with ddPCR capable of detecting single copies of ChIP-DNA, thus offering the capability of single cell analysis and, thereby, minimizing input sizes and informing about cancer heterogeneity. The disclosed devices and methods have a scalability of inputs from single cells to numerous number of cells, permitting rigorous, genome-wide validation of performance, thus facilitating interfacing with deep sequencing and handling various clinical samples.

The disclosed devices and methods can be used for any epigenomics analysis methods, such as ChIP or variants such as indexing-first chromatin immunoprecipitation (iChIP), methyl-CpG-binding domain protein-based capture, methylated DNA immunoprecipitation and hydroxymethylated DNA immunoprecipitation, as well as micrococcal nuclease (MNase)-based nucleosome positioning assay, assay for transposase-accessible chromatin (ATAC) and DNase hypersensitivity (DHS) assay, etc. ATAC and DHS analysis can be used to analyze chromatin structure and identify genomic regulatory elements. Thus, nucleosomes obtained using the disclosed automated methods can be analyzed using known ChIP or DHS steps, such as immunoprecipitation and retrieval of nucleosome-associated DNA or retrieval of nucleosome-free DNA following the immunoprecipitation and removal of the nucleosomes. In one example, the methods are used to measure cellular heterogeneity (e.g., heterogeneity present in a tissue sample, such as a cancer biopsy or a complex biopsied or postmortem tissue sample such as liver or brain). Because the method analyzes single cells, the heterogeneity within a tissue comprised of numerous cells can be determined.

In one example, the methods are used to identify epigenomic changes involved in the epithelial to mesenchymal transition (EMT), such as those that occur during cancer development, such as pancreatic cancer or gastric cancer. For example, changes in the repressive H3K27me3 and the activating H3K4me3 marks associated with the promoters of genes that are differentially expressed in normal epithelial cells and cells undergoing EMT can be determined using the disclosed methods. In one example, the methods are used to identify patients that are likely to, and not likely to, respond to a particular therapy. In some examples, the method includes administering an appropriate therapy (such as a chemotherapeutic or biologic) to a patient that the assay indicated will be responsive to the treatment. Thus, the methods allow for the development and implementation of personalized approaches to patient treatment.

In one example, the methods are used to determine if a subject will respond to a drug that targets epigenetic regulators (e.g., DNA methyltransferase and histone deacetylase inhibitors), such as those used in cancer treatment. Such methods help ensure that patients are ideally matched with available treatments.

In one example, the methods are used to identify epigenetic changes that occur in a subset of cells in a complex tissue such as CD34+ hematopoietic stem/progenitor cells of the bone marrow of patients with myelodysplastic syndrome prior to the development of acute myeloid leukemia.

In one example, the methods are used to detect epigenomic changes in very small biopsies obtained e.g. via endoscopic techniques from lesions within the gastrointestinal tract to determine their biological behavior and drug responsiveness. Current epigenomic methods are not typically suitable for the analysis of small samples obtained by minimally invasive techniques and require open surgeries, which carry considerably higher risk and cost more.

Provided herein are microfluidic devices that can be used for the creation and/or manipulation of droplets in droplet-based microfluidic systems, as well as systems and methods for using the same. Such devices can be used to perform the methods provided herein. The microfluidic devices can be used to generate droplets, extract or inject volume to droplets, and/or split droplets.

In particular examples, a microfluidic device includes at least one "K-junction." As used herein, the term "K-junction" means a device or portion of a device that includes at least one main channel and at least two side channels that intersect or engage with the main channel at an angle, resulting in a shape that resembles the letter "K." In some embodiments, the K-junction can be configured to generate droplets, extract or inject volume to droplets, split droplets, or otherwise process a fluid traveling in the main and/or side channels. This can improve the functionality and versatility of the microfluidic device.

In particular examples, a microfluidic device includes one or more electrode channels at or near the K-junction. The electrode channels can be configured to enhance droplet destabilization and manipulation at the K-junction.

Figure 1B:
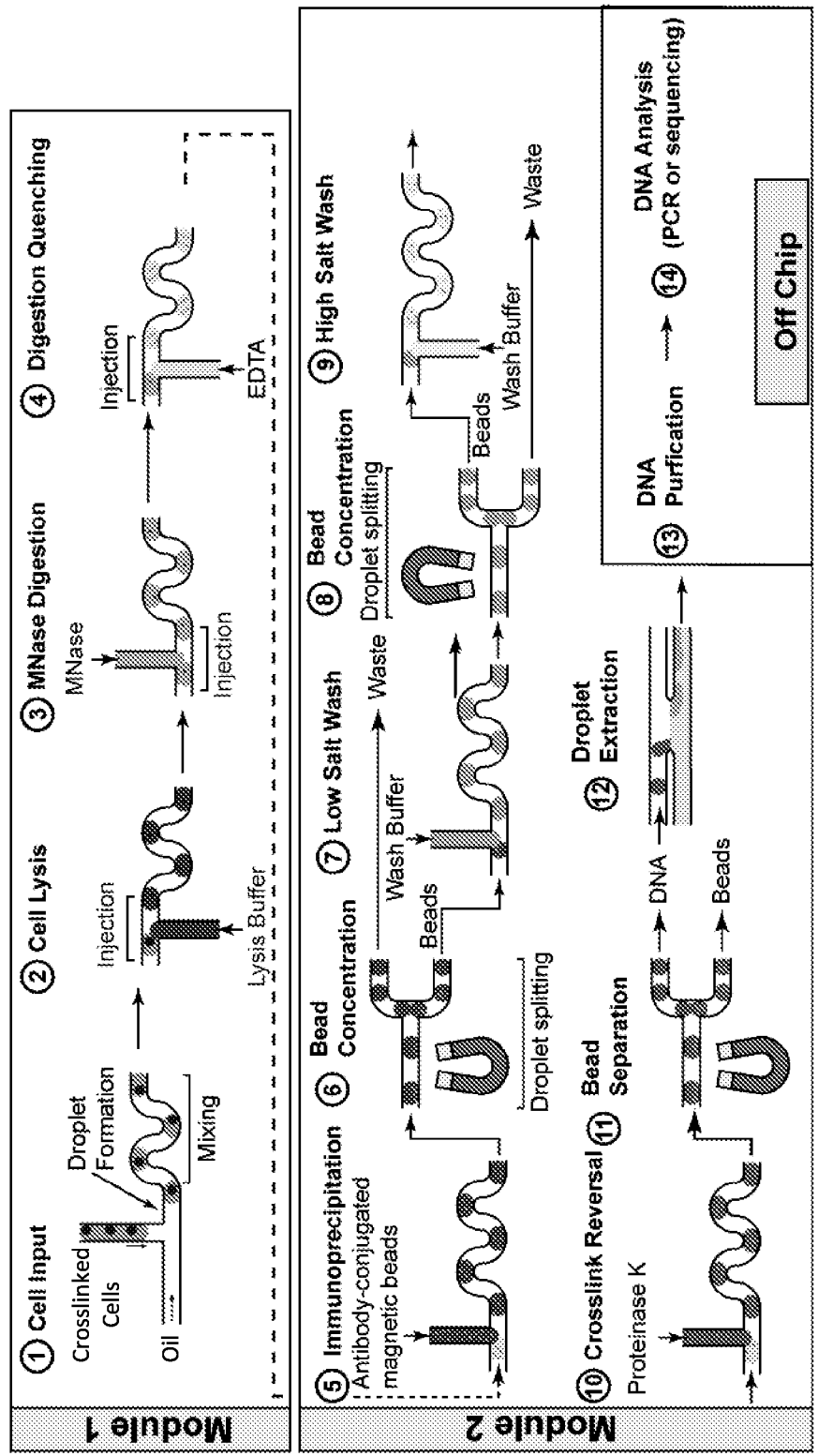
Figure 1C:
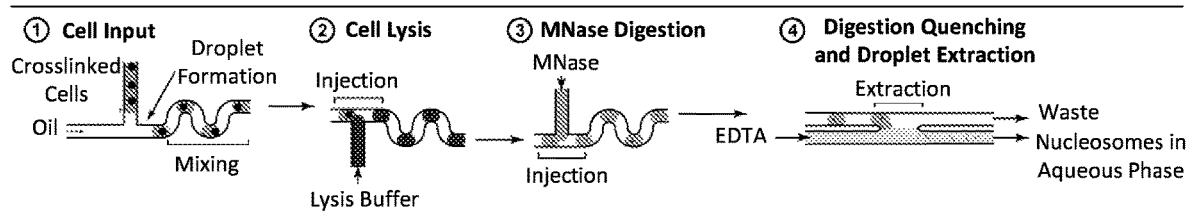

The disclosure provides automated methods of generating nucleosomes, such as mono, di-, and/or trinucleosomes (e.g., see FIG. 1C). Such methods use a suspension of crosslinked eukaryotic cells as input and nucleosomes from the cells are the output. Alternatively, nucleosome-free, fragmented DNA can also be utilized as output, for example, in the context of DNase hypersensitivity assay. The resulting nucleosomes from a plurality of cells (such as at least 100 cells, at least 1000 cells, at least 10,000 cells, at least 100,000 cells, or even at least 1,000,000 cells) can be pooled into an aqueous quench solution which stops or retards chromatin digestion. Such methods provide an automated method of quickly obtaining nucleosomes, wherein the resulting nucleosomes can be used for subsequent analysis, such as epigenetic analysis (e.g., ChIP or other assays). In some examples, such methods include encapsulating an aqueous solution that includes a suspension of cells (wherein the cells can be crosslinked) and a lysing solution within a droplet, resulting in droplets that contain in some examples not more than a single cell. The droplet has an outer oil-containing layer, which is not miscible with the aqueous solution containing the cell. For example, the droplet can be formed by using an automated droplet formation means. The cell within the droplet is then incubated under conditions that allow for lysis of the cell within the droplet. Subsequently, a nuclease solution (e.g., one that does not cleave the nucleosome, such as MNase, or DNAase I) is added to the droplet, thereby cleaving DNA in the droplet without substantially affecting portions of the DNA that interact with histones within the nucleosomes. For example, the nuclease solution can be added to the droplet by using an automated injection means, such as an injector and a means to apply a voltage (e.g., electric field generator) to the droplet, thereby allowing the non-nucleosome-cleaving nuclease solution to merge with the droplet. After allowing for an adequate amount of DNA digestion, a plurality of the droplets are automatedly moved or transferred to an aqueous quenching solution, under conditions that allow quenching of the non-nucleosome-cleaving nuclease. For example, the droplet can be moved or transferred to an aqueous quenching solution by using an automated means, such as a means to apply a voltage (e.g., electric field generator) to the droplet, which allows the droplet to move to a different portion of the device. This results in the generation of a population of nucleosomes in an aqueous phase.

Methods of analyzing DNA associated with nucleosomes, such as from mono, di-, and/or trinucleosomes, are provided. Such methods can have one or more steps automated (such as automation of the steps from lysis of the cell to isolation of DNA from the nucleosomes), and use crosslinked eukaryotic cells as input with droplets each containing nucleosome DNA from a single cell (e.g., see FIG. 1A). The DNA in the resulting droplets can be analyzed, thereby allowing single-cell epigenetic information to be obtained, for example allowing for single-cell amplification (e.g., PCR) and/or sequencing analysis. In some examples, such methods include encapsulating an aqueous solution that contains a cell suspension (wherein the cells can be crosslinked) and a lysing solution within a droplet, resulting in the production of single droplets each containing a single cell. The droplet has an outer oil-containing layer, which is not miscible with the aqueous solution containing the cell. For example, the droplet can be formed by using an automated droplet formation means. The cell within the droplet is then incubated under conditions that allow for lysis of the cell within the droplet. Subsequently, a nuclease solution (such as one that does not cleave nucleosomes) is added to the droplet, thereby cleaving DNA in the droplet without substantially affecting portions of the DNA that interact with histones within the nucleosomes. For example, the nuclease solution can be added to the droplet by using an automated injection means, such as an injector and a means to apply a voltage (e.g., electric field generator) to the droplet, thereby allowing the nuclease solution to merge with the droplet. After allowing for an adequate amount of DNA digestion, a quenching solution is added to the droplet, thereby quenching the activity of the nuclease. For example, the quenching solution can be added to the droplet by using an automated injection means, such as an injector and a means to apply a voltage (e.g., electric field generator) to the droplet, thereby allowing the quenching solution to merge with the droplet. After allowing for an adequate amount of quenching, a solution containing a solid support comprising one or more-specific binding reagents (such as those can specifically bind to a portion of a nucleosome, such as one or more transcription factors, histones, modified amino acids within histones, DNA, modified bases within DNA, and non-histone proteins) is added to the droplet. For example, the solid support containing solution can be added to the droplet by using an automated injection means, such as an injector and a means to apply a voltage (e.g., electric field generator) to the droplet, thereby allowing the solid support containing solution to merge with the droplet. The solid support is incubated under conditions that allow it to bind to portions of the nucleosomes within the droplet. The solid support bound to the nucleosomes (e.g., histones) is then concentrated, and optionally washed, for example by using means that allow for concentration of the solid support (e.g., magnet, centrifugal forces, flow cytometry) and a means that allows for removal of part of the droplet (e.g., means to apply a voltage). An enzyme solution that can release the histones and DNA from the solid support is added to the resulting portion of the droplet containing the solid support. For example, the enzyme solution can be added to the droplet by using an automated injection means, such as an injector and a means to apply a voltage (e.g., electric field generator) to the droplet, thereby allowing the enzyme solution to merge with the droplet. After allowing for an adequate amount of digestion, the droplet is separated into a portion containing the solid support and a portion containing the DNA, for example by using means that allow for concentration of the solid support (e.g., magnet, centrifugal forces, flow cytometry) and a means that allows for removal of part of the droplet (e.g., means to apply a voltage). The portion of the droplet containing the DNA is collected, for example using an automated means. The resulting nucleosome DNA from a single cell can then be purified and concentrated if desired, and analyzed (e.g., using PCR and/or sequencing). In another example, the portion of the droplet containing the DNA is then exposed to a solution containing a solid support that includes (e.g., is coated with) DNA capture reagents. For example, the solution containing the solid support can be added to the droplet by using an automated injection means, such as an injector and a means to apply a voltage to the droplet (e.g., electric field generator), thereby allowing the solid support containing solution to merge with the droplet. The solid support is incubated under conditions that allow it to bind to DNA within the droplet. The solid support bound to the DNA is then concentrated, and optionally washed, for example by using means that allow for concentration of the solid support (e.g., magnet, centrifugal forces, flow cytometry). The DNA is eluted from the beads, and the solid support removed (e.g., using a magnet, centrifugal forces, flow cytometry). The resulting nucleosomal DNA from a single cell can then be further concentrated if desired, and analyzed (e.g., using PCR and/or sequencing). In some examples, a plurality of single cells within a plurality of single droplets are analyzed contemporaneously.

In some examples, the nucleosome and associated DNA can be removed following immunoprecipitation with an affinity reagent (antibody) targeting all nucleosomes to allow the selective harvesting of internucleosomal DNA for downstream analysis.

In some examples, the step of collecting the portion of the droplet containing the DNA that was associated with the nucleosomes includes combining DNA from a plurality of droplets into a single solution, thereby generating a solution of nucleosome DNA from a plurality of cells (e.g., see FIG. 1B). This pooled DNA can be purified and concentrated if desired, and analyzed (e.g., using PCR or other amplification=and/or sequencing).

In some examples, the step of encapsulating includes encapsulating a single cell within the droplet, and subsequently adding to the formed droplet a lysing solution, thereby lysing the cell within the droplet. In another example, the step of encapsulating includes adding a lysing solution to an aqueous solution containing a cell suspension, cell prior to forming the droplet.

In some examples, the steps that involve adding solutions/reagents to the droplet are achieved by destabilizing the droplet with a high voltage (HV) field.

In some examples, the single cell within a droplet is present in a microchannel, such as a curved or serpentine microchannel, or a double-walled microchannel, such as one that is about 20 to 100 μm in diameter. In some examples, all of the steps of nucleosome preparation, immunoprecipitation, and DNA separation from the solid support, take place in the droplet, such that the cell and its contents do not touch the wall of a microchannel in which the droplet is located. For example, the cell and its contents are not anchored or attached to the microchannel.

In some examples, instead of using a nuclease (e.g., MNase) to digest the chromatin, a two-step nucleosome targeting scheme using hyperactive Tn5 transposase, which can simultaneously fragment and tag accessible chromatin while being unable to disrupt compacted chromatin (see e.g., Buenrostro et al., *Nat Meth* 2013; 10:1213), with MNase following the removal of the tagged, digested nucleosomes, is used. Such a method may reduce or eliminate the chance of overdigesting accessible chromatin with nuclease while dissociating heterochromatin.

Any eukaryotic cell can be analyzed with the disclosed devices and methods. In one example the eukaryotic cell is a human cell, invertebrate cell, amphibian cell, or bird cell, plant cell, such as a cancer cell or cancer stem cell.

Methods of Analyzing Nucleosomes

Provided herein is a microfluidics platform which can be used to analyze one or more nucleosomes in a cell (such as a mono-, di-, or trinucleosomes, or combinations thereof), for example to perform genome-wide ChIP analysis on a single cell or a plurality of cells. Although the specific examples herein describe how the method can be used for ChIP analysis, similar methods can be used for variants of ChIP assay such as indexing-first chromatin immunoprecipitation (iChIP), methyl-CpG-binding domain protein-based capture, methylated DNA immunoprecipitation and hydroxymethylated DNA immunoprecipitation, as well as micrococcal nuclease (MNase)-based nucleosome positioning assay, assay for transposase-accessible chromatin (ATAC) and DNase hypersensitivity (DHS) assay. In one example, the disclosed methods allow for a determination of the presence of zero, one or two copies of the targeted DNA (assuming single, diploid cells) in a single cell (e.g., detected by digital droplet PCR reporting); i.e., differential occupancy (by histone markers and the like) of the same genomic sequences in different alleles.

Figure 1D:
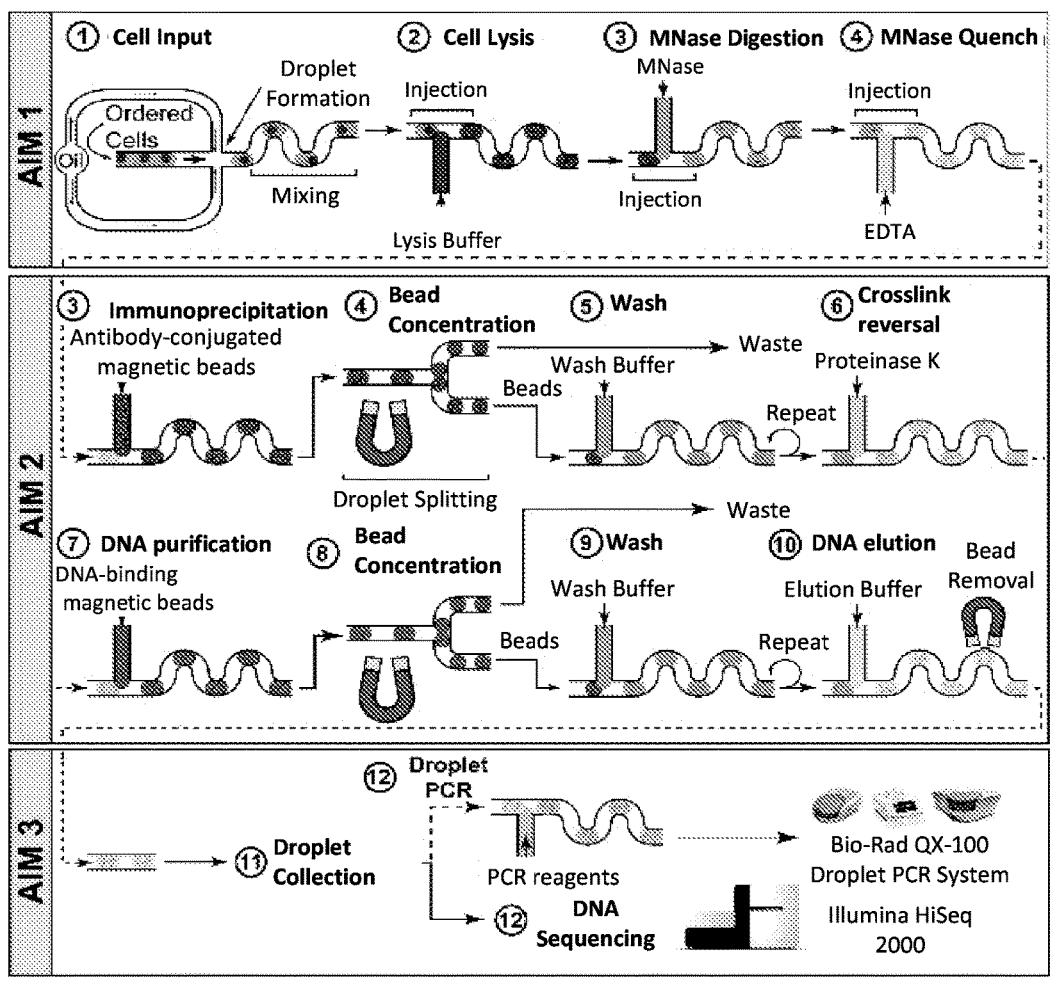

Exemplary embodiments of the methods are provided in FIGS. 1A-1D. As shown in FIG. 1A, the method can include using crosslinked cells as input and obtaining droplets with a single cell (step 1), to eventually generate droplets, each containing DNA associated with nucleosomes from a single cell (step 12). The resulting droplets are ready for single-cell analysis, for example amplification (e.g., polymerase chain reaction (PCR) including nested PCR, quantitative or real-time PCR (qPCR), and digital droplet PCR (ddPCR)) and/or sequencing. Such methods allow for the identification of epigenetic information from single cells. A modification of the method of FIG. 1A is shown in FIG. 1D, wherein DNA associated with nucleosomes is isolated using solid supports and eluted (steps 7 to 10 of FIG. 1D), instead of merely isolating a portion of a droplet containing DNA following treatment with an enzyme that digests proteins (steps 10-11 of FIG. 1A). Alternatively, as shown in FIG. 1B, the method can include using crosslinked cells as input (step 1) and obtaining DNA associated with nucleosomes from a plurality of cells in aqueous phase as output by extracting droplets automatically (step 12). That is, the DNA associated with nucleosomes from single cells is pooled into an aqueous phase. This strategy saves the manual step of droplet breaking at the end of the process. This embodiment can be used clinically as it automates the entire process, thus requiring fewer cells than standard methods (e.g., can be used to automate standard ChIP protocols and use fewer cells). In some examples, as shown in FIG. 1C, the method can include using crosslinked cells as input (step 1) and obtaining nucleosomes from a plurality of cells in aqueous phase as output by extracting droplets to quench prior chromatin digestion (step 4). This embodiment can be used clinically to obtain nucleosomes from a plurality of cells, which can then be processed using other protocols (e.g., can be used with other standard ChIP steps and use fewer cells). This embodiment automates part of the ChIP process, thus requiring fewer cells than standard ChIP methods.

In some examples, for example where a DNase hypersensitivity (DHS) assay is performed, the non-nucleosome DNA is retained (instead of retaining the nucleosome DNA).

The disclosed device and method permit the formation of uniform, nanoliter-scale droplets containing in some examples one cell. Additional reagents (such as lysis buffer, nuclease, and quencher) can be injected or introduced into the droplet by destabilizing the droplet with a high voltage (HV) field.

Single Cell Nucleosome Analysis

An overview of one embodiment of the method is provided in FIG. 1A. This example of the method includes two general modules: (1) cell lysis and chromatin shearing, and (2) immunoprecipitation using a solid support (e.g., beads). The goal of module 1 is to obtain nuclear material of a specific size (e.g., mixture of mono-, di-, and/or trinucleosomes), and the goal of module 2 is to obtain the DNA associated with the nucleosome(s) for individual cells.

Such methods and devices permit encapsulation of single cells within droplets and the multiple downstream processing steps (e.g., cell lysis, nucleosome preparation, bead capture and washing, etc.) can be performed in a manner in which the original genomic content of a single cell remains within a single droplet (e.g., materials from single cells are not combined). The generation of ChIP-DNA from single cells within single droplets is compatible with digital droplet qPCR (ddPCR) and provides a high throughput method for assessing single cell epigenomics. An example of the type of data that can be obtained is the percentage of cells that have a specific epigenomic mark at a particular genomic region, which is useful for understanding epigenomic heterogeneity.

Cell Lysis and Chromatin Shearing

As shown in FIG. 1A, at step 1 (cell input), cells are encapsulated in droplets, for example by using a microfluidic droplet maker (e.g., within an aqueous environment contained within an oil). Typically, the cells are encapsulated within droplets at a density such that on average, each droplet contains one cell (or less). Thus, in some examples, individual droplets contain a single cell (that is, one cell per droplet), allowing for reactions to be performed on a single cell. This makes the need for large amounts of sample unnecessary. Within a droplet, a cell is exposed to additional reagents, such as those that permit lysis of the cell, and cleavage of DNA.

A liquid suspension containing single cells (or even a single cell) that have been crosslinked is introduced into the device, for example via injection. In some examples, the cells are present in a buffer. In one example, the suspension of crosslinked single cells is present in an aqueous phase.

Figure 2A:
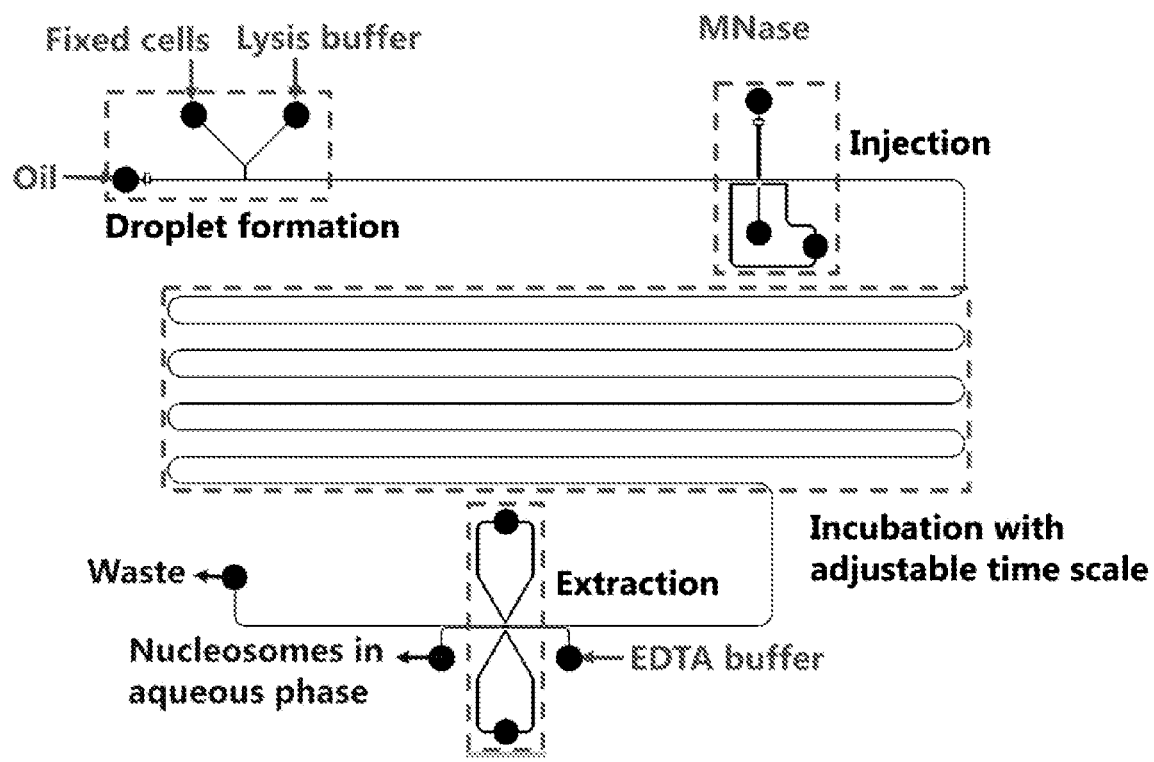
FIG. 2A provides an exemplary device of droplet making, which can be used to generate cell-containing droplets, and add or subtract materials from the droplet. Fixed/crosslinked cells in an aqueous suspension are introduced into the device along with a lysis buffer. An exemplary Y-junction is shown, but other junctions could be used (such as a K-junction). An oil phase is also introduced into the device, which interacts with the aqueous phase, thereby forming droplets. The cell-containing droplets flow to an injection port, which allows materials to be added to the droplet, such as MNase or other nuclease. The device can include additional injection ports if desired, or a single injection port can be used to introduce a plurality of different reagents. The device includes microfluidic channels, which can be curved (e.g., serpentine) or straight. In some examples, the channel is straight, and includes a parallel set of channels that can allow material in one channel to enter another channel. The device also includes an extraction port, which allows materials to be removed.
Figure 2B:
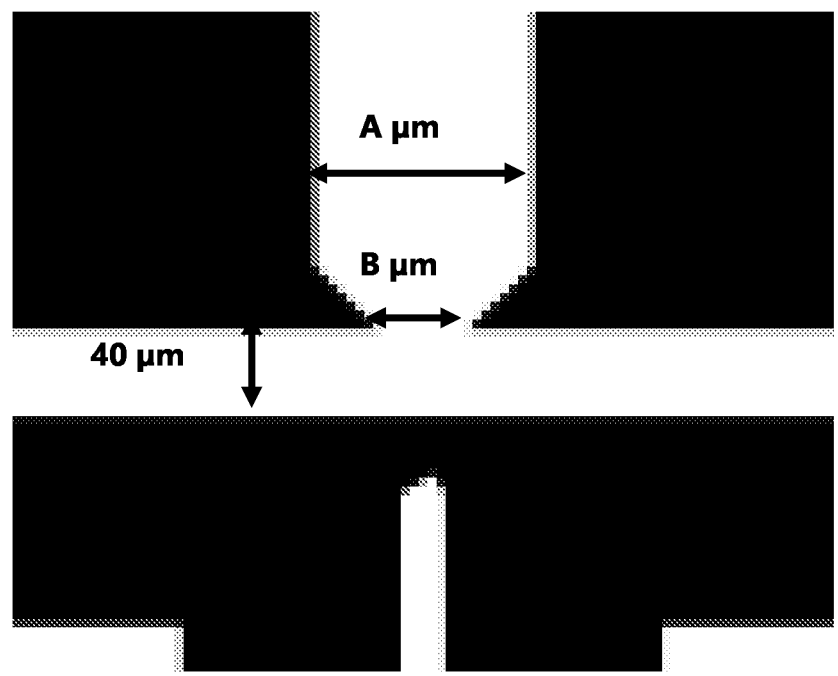
FIG. 2B provides a schematic of an exemplary injection site.
Figure 2C:
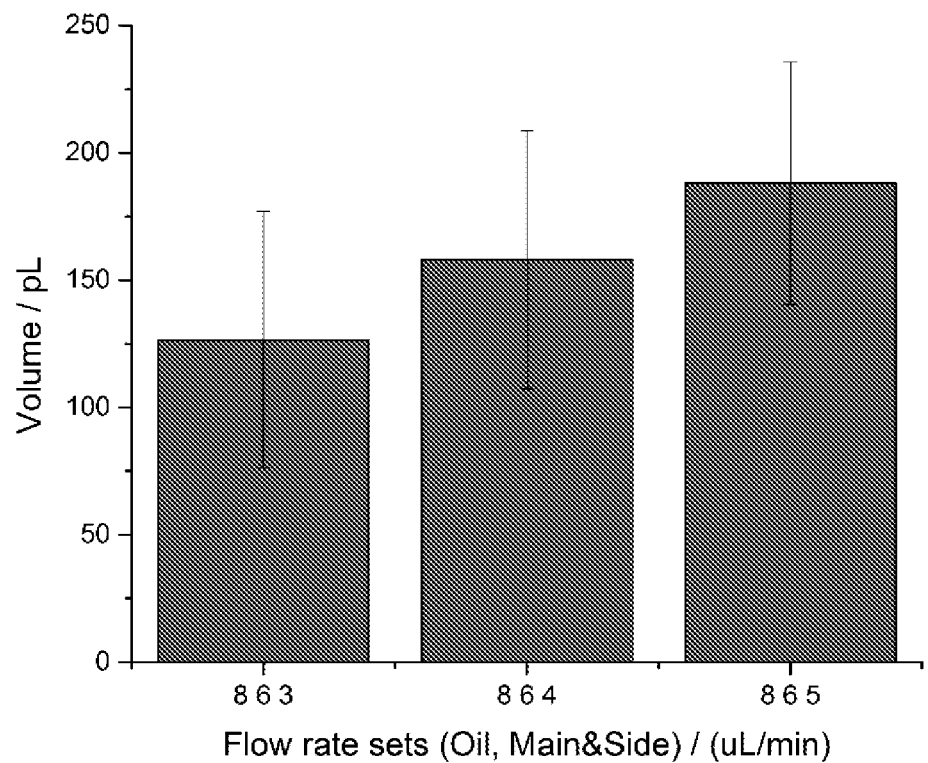
FIG. 2C is a graph showing injection with and without destabilization by high voltage electric field. This figure represents amount of volume injected into a droplet. Y axis is the volume added per droplet in picoliters.

The crosslinked cells are then incorporated or encapsulated into a microdroplet. As shown in FIG. 2A, droplets are formed by allowing an oil phase containing a surfactant to interact with or contact the aqueous cell-containing solution under conditions that permit a single cell to become encapsulated within a single droplet. In one example, the oil phase includes 2% (weight percentage) surfactant. Any biocompatible oil can be used, such as a, fluorinated oil (e.g., FC40, FC70, and the like). In one example the oil phase containing a surfactant includes or consists of 3M® Novec™ 7500 engineered fluid and fluorosurfactant. The interaction between the two different phases results in the formation of a droplet containing single cells.

As shown in FIG. 1A, at step 2 (cell lysis), the cells contained within the droplets are exposed to one or more reagents that permit lysis of the cells within the droplet. For example, cells can be exposed to one or more enzymes or chemicals, such as one or more detergents (e.g., Triton, Triton X-100, saponin, NP-40, and the like) for at least 0.1 seconds, such as at least 0.5, or at least 1 second. In one example, the lysis buffer is 10 mM Tris-HCl, pH 7.5, 10 mM NaCl, 0.5% NP-40, and the incubation is for 1 to 60 seconds or 5 to 10 minutes. Another exemplary lysis buffer is 10 mM HEPES, pH 7.9, 1.5 mM $MgCl_2$, 10 mM KCl, 0.5% IGEPAL-CA630 and optionally 0.5 mM dithiothreitol (DTT). The cell lysis reagents are incubated with the droplets under conditions sufficient for the cells in the droplets to be lysed, such that the nucleosomes in the cell can be accessed. In some examples, the lysis buffer is allowed to interact with the cells in the droplets for at least 5 minutes, at least 10 minutes, at least 20 minutes, or at least 30 minutes, such as 5 to 60 minutes. In some examples, the droplets move or flow through the device and arrive at a stage of the device that permits their injection with a lysis buffer or permits introduction of a lysis buffer, for example by merging the cell-containing droplet with a lysis buffer droplet (e.g., see FIG. 4D). In some examples, the droplet is "mixed" by moving the droplet through a serpentine microchannel. In some examples, the lysis solution is added to the device with the cell suspension, to form a solution containing lysis buffer and crosslinked cell, and then this solution mixed with oil to form the droplets, thereby resulting in the lysis buffer becoming incorporated into the droplet containing the cell (e.g., see FIG. 2A).

As shown in FIG. 1A, at step 3 (MNase digestion), the DNA of the lysed cells is exposed to an enzyme, such as a non-nucleosome-cleaving nuclease or other enzyme able to cleave the DNA without destroying epigenetic information. In one example, the enzyme is micrococcal nuclease (MNase). In another example, the enzyme is DNase I or Tn5 transposase. In one example, the nuclease is present in the buffer 20 mM Tris-HCl, pH 7.5, 15 mM NaCl, 60 mM KCl, 1 mM $CaCl_2$, or the buffer 20 mM Trizma hydrochloride, pH 7.5, 15 mM NaCl, 60 mM KCl, 5 mM $CaCl_2$, 0.15 mM spermine, 0.5 mM spermidine, and optionally 1% Pluronic and 0.1% BSA, which cleaves the DNA in the lysed cell into smaller fragments, without substantially affecting those portions of the DNA that interact with the histones within the nucleosome structures. The solution containing the enzyme is incubated with the droplets under conditions sufficient for the DNA in the droplets to be cleaved. In some examples, the solution containing the enzyme is allowed to interact with the cells in the droplets for at least 5 minutes, at least 10 minutes, at least 20 minutes, or at least 30 minutes, such as 5 to 60 minutes. In some examples, the droplets move or flow through the device and arrive at a stage of the device that permits their injection with a solution containing the enzyme or permits introduction of a solution containing the enzyme, for example by merging the cell-containing droplet with a nuclease-containing droplet (e.g., see FIG. 4D).

In some examples, the enzyme (e.g., MNase) concentration and reaction time achieves (i) a ≥85% mono+dinucleosome yield (e.g., determined by quantitative fragment analysis) from nuclei as input; (ii) demonstrate single cell droplet encapsulation with ≥75% efficacy (e.g., determined by microscopy); (iii) demonstrate ≥70% mono+dinucleosome yield from droplet-encapsulated single cells (e.g., by fragment analysis); and (iv) directly benchmark upscaled on- vs. off-chip MNase in terms of broad genomic accessibility using MNase-qPCR and MNase-seq and quantitative criteria.

As shown in FIG. 1A, at step 4 (MNase quench), the enzyme reaction performed in step 3 is stopped (quenched), by adding an appropriate reagent to the droplet, such as EDTA. In one example, the quencher solution is 100 mM Tris-HCl, pH 8, 20 mM EDTA, 200 mM NaCl, 2% Triton-X 100, 0.2% Sodium dodecyl sulfate. The quencher solution is incubated with the droplets under conditions sufficient to significantly reduce the enzyme activity and reduce DNA cleavage. In some examples, quencher solution is allowed to interact with the cells in the droplets for at least 5 minutes, at least 10 minutes, at least 20 minutes, or at least 30 minutes, such as 5 to 60 minutes. In some examples, the droplets move or flow through the device and arrive at a stage of the device that permits their injection with a quencher solution or permits introduction of a quencher solution, for example by merging the cell-containing droplet with a quencher-containing droplet (e.g., see FIG. 4D).

In one example, the volume added to the droplet to provide the necessary reagents is about 100 pL, about 150 pL or about 200 pL, such as 100 to 200 pL.

Immunoprecipitation and Analysis of DNA

Module 2 of one example of the method involves isolating or concentrating the nucleosomes generated in Module 1, and then analyzing the DNA associated with the nucleosomes. As shown in FIG. 1A, at step 5 (immunoprecipitation), the nucleosome(s) in each droplet (and thus the nucleosome from a single cell) is captured using immunoprecipitation using one or more reagents that specifically bind to one or more histone proteins (such as 1, 2, 3 or 4 of H2A, H2B, H3, and H4), their variants, covalent modifications, transcription factors, and non-histone proteins, as well as DNA modifications, allowing the unlabeled chromatin in each droplet to be removed in subsequent steps. For example antibodies, antibody fragments, or other specific binding reagents (such as a functional nucleic acid, e.g., aptamer, DNAzyme, RNAzyme, aptazyme, and the like) can be used.

The specific binding reagent is present on a solid support, such as a bead, microsphere, or other particle. Methods of attaching or immobilizing a specific binding agent to a solid support are known. In some examples, the solid support is composed of metal (e.g., gold, silver, platinum), metal (e.g., zinc oxide, zinc sulfide, copper sulfide, cadmium sulfide), non-metal (e.g., silica or a polymer), or magnetic materials (e.g., iron oxide, manganese oxide). In some examples the solid support is a latex or glass bead. In one example, the solid support is magnetic bead. The size of the solid support is not critical; exemplary sizes include beads that are 5 nm to 5000 nm in diameter, such as 1 to 100 nm, 1 to 50 nm, 1 to 10 nm, 2 to 20 nm, or 5 to 25 nm. In one example such particles are about 1 µm in diameter.

Thus, the method includes contacting the cells in the droplets that were lysed and contacted with the non-nucleosome-cleaving nuclease and quencher, with particles containing immobilized binding agents that are specific for a histone protein, or a histone variant, histone modification, nonhistone protein, transcription factor, or DNA modification, for example by introducing such particles into the droplet containing the nucleosomes. The particles are incubated with the droplets under conditions sufficient for targets in the droplet to bind to the specific binding agent on the particles. In some examples, the particles are allowed to interact with the nucleosomes in the droplets for at least 5 minutes, at least 10 minutes, at least 20 minutes, or at least 30 minutes, such as 5 to 60 minutes.

To dilute out the unbound chromatin, the droplet-containing particles are subjected to a series of concentration steps and washes, such as with a salt-containing solution. As shown in FIG. 1A, at step 6 (bead concentration), the particles (which will have nucleosome(s) bound to them) are concentrated, and the size of the droplet is reduced by at least 10%, at least 20%, at least 25%, at least 30%, at least 40%, at least 50%, at least 60%, at least 66%, at least 75%, at least 80%, or at least 90% (such as 25 to 75%) of the volume of the droplet is removed.

For example, the droplet can be treated to generate a portion of the droplet containing unbound chromatin and another portion of the droplet containing the solid support bound to the target(s). These portions of the droplet can be treated or "split" to substantially remove the portion of the droplet containing unbound chromatin, thereby leaving the portion of the droplet containing the solid support bound to histones/nucleosomes. In some examples, at least 10%, at least 20%, at least 40%, at least 50%, at least 75%, at least 80%, at least 90%, at least 95%, or at least 99% (such as 25 to 75%) of the portion of the droplet containing unbound chromatin is removed, thereby resulting in a smaller droplet containing the solid support bound to targets. For example, if the particles are magnetic, then the droplets can be exposed to a magnetic force, and the droplet split, so that the portion of the droplets containing the particles is divided or separated from the portion of the droplets not containing the solid support. Other methods of separation can be used, such as centrifugal forces, which will precipitate the solid support, or flow cytometry methods, which can collect the portion of the droplet containing the solid support or the portion containing the unbound chromatin.

As shown in FIG. 1A, at step 7 (low salt wash), the portion of the droplet containing the solid support (which have nucleosome(s) bound to them) can be subjected to a low salt wash, for example by introducing a low salt buffer into the droplet containing the solid support. In one example, the low salt buffer includes about 100 to 200 nM salt, such as about 150 mM salt, such as 150 mM NaCl, for example in the presence of a detergent (such as 20 mM Tris-HCl (pH 8.1), 2 mM EDTA, 150 mM NaCl, 0.1% SDS, and 1.0% Triton X-100). In some examples, the solid support in the droplets are allowed to interact with the low salt wash buffer for at least 5 minutes, at least 10 minutes, at least 20 minutes, or at least 30 minutes, such as 5 to 60 minutes.

The droplets can be split and washed one or more times (such as 1, 2, 3, 4, 5, 6, 7, 8, 9 or 10 times), to achieve desired levels of purity.

As shown in FIG. 1A, at step 8 (bead concentration), following a first wash (e.g., low salt wash), the process of concentrating the solid support is repeated, reducing the size of the droplet (e.g., as described for the process described for step 6). For example, if the solid supports are magnetic, then the droplets can be exposed to a magnetic force, and the droplet split, so that the portion of the droplets containing the solid support is divided or separated from the portion of the droplets not containing the solid support. Other methods of separation can be used.

As shown in FIG. 1A, at step 9 (high salt wash), the portion of the droplet containing the solid support (which have nucleosome(s) bound to them) can be subjected to a high salt wash, for example by introducing a high salt buffer into the droplet containing the solid support. In one example, the high salt buffer includes about 300 to 600 nM salt, such as about 500 mM salt, such as 500 mM NaCl, for example in the presence of a detergent (such as 20 mM Tris-HCl (pH 8.1), 2 mM EDTA, 500 mM NaCl, 0.1% SDS, and 1.0% Triton X-100). In some examples, the solid support in the droplets are allowed to interact with the high salt wash buffer for at least 5 minutes, at least 10 minutes, at least 20 minutes, or at least 30 minutes, such as 5 to 60 minutes.

After diluting out or substantially removing chromatin not bound to the particles, the droplet containing the solid support is exposed to reagents that release the materials bound to the particles, thus reversing the crosslinking between the proteins and the DNA. For example, as shown in FIG. 1A, at step 10 (crosslink reversal), the droplets can be treated with (e.g., by introducing into the droplet) an enzyme that digests proteins (such as antibodies and histone proteins), such as proteinase K (e.g., at about 0.1 mg/ml). RNA present in these preparations may also be digested with RNase A. In some examples, the particles in the droplets are allowed to interact with the enzyme for at least 5 minutes, at least 10 minutes, at least 20 minutes, at least 30 minutes, at least 60 minutes, at least 120 minutes, or at least 4 hours, such as 5 to 60 minutes.

After releasing the DNA from the solid support, the droplet containing the DNA and solid support can be exposed to conditions that allow the solid support to be separated from the DNA. For example, as shown in FIG. 1A, at step 11 (bead separation), the particles are concentrated, and the size of the droplet is reduced, similar to the process used in steps 6 and 8. For example, if the particles are magnetic, then the droplets can be exposed to a magnetic force, and the droplet split, so that the portion of the droplets containing the particles is divided or separated from the portion of the droplets containing the DNA. Other methods of separation can be used. An alternative means to obtain the nuclesomal DNA is shown in FIG. 1D, wherein DNA associated with nucleosomes is isolated using solid supports (e.g., similar to those described above for immunoprecipitation) and eluted (steps 7 to 10 of FIG. 1D), instead of merely isolating a portion of a droplet containing DNA following treatment with an enzyme that digests proteins (steps 10-11 of FIG. 1A). In some examples, after the crosslink reversal, such as after the droplet containing the DNA and solid support are exposed to conditions that allow the solid support to be separated from the DNA (e.g., after step 11 FIG. 1A, discussed above), the resulting DNA in the droplet is concentrated or purified, for example by introducing solid supports that bind to the DNA, such as a beads containing an appropriate nucleic acid molecule (e.g., one with a sequence complementary to the DNA in the droplet or using other appropriate reagents (e.g., Dynabeads from Invitrogen) (step 7 of FIG. 1D). The resulting solid supports bound to the DNA that was on the nucleosome can be concentrated and washed as described above (steps 8-9 of FIG. 1D). The DNA on the solid support can be eluted, and separated from the solid support (step 10 of FIG. 1D), and the resulting DNA-containing droplet collected and analyzed (steps 11-12 of FIG. 1D). Thus, in some examples, after releasing the histones, nonhistone proteins, and DNA from the solid support, portion of the droplet containing the DNA is incubated with a second solid support that binds to the DNA, for example by using an automated injection means, such as an injector and a means to apply a voltage to the droplet (e.g., electric field generator), thereby allowing the second solid support containing solution to merge with the droplet. After allowing for an adequate amount of binding, the solid supports can be optionally washed, and the bound DNA eluted, and the solid supports separated from the eluted DNA (e.g., by using methods that allow for concentration of the second solid support (e.g., magnet, centrifugal forces, flow cytometry) and a means that allows for removal of part of the droplet (e.g., means to apply a voltage)). In one example, the portion of the droplet containing the DNA is collected. The resulting nucleosome DNA from a single cell can then be purified and concentrated if desired, and analyzed (e.g., using PCR and/or sequencing). In some examples, a plurality of single cells within a plurality of single droplets are analyzed contemporaneously.

The DNA-containing droplet (or portion of the droplet containing the DNA from the isolated nucleosomes), can then be analyzed. The DNA (which may still be present in a droplet) can be then exposed to reagents that permit amplification (such as PCR reagents, e.g., Taq Polymerase, dNTPs, primers, $MgCl_2$) and/or reagents for sequencing. Exemplary methods of amplification include PCR, such as real-time (quantitative) PCR, digital droplet PCR (ddPCR). For example, the DNA can be analyzed using the Bio-Rad QX-100 droplet PCR system and/or the Illumina HiSeq 2000 system (or other equivalent).

Nucleosome Analysis from Multiple Cells

An overview of one embodiment of the method is provided in FIG. 1B. This example of the method includes two general modules: (1) cell lysis and chromatin shearing, and (2) immunoprecipitation using a solid support (e.g., beads). The goal of module 1 is to obtain nuclear material of a specific size (e.g., mixture of mono-, di-, and/or trinucleosomes), and the goal of module 2 is to obtain the DNA associated with the nucleosome(s) for a plurality of cells. The method is similar to the one shown in FIG. 1A, except that at step 12, instead of collecting individual droplets containing the DNA from individual cells, the DNA from all of the cells analyzed is pooled together. This embodiment can be used clinically as it automates the entire process, thus requiring fewer cells than standard methods (e.g., can be used to automate standard ChIP or DNase hypersensitivity protocols (but wherein the DNA is obtained from non-nucleosome DNA as described below) and use fewer cells).

In this method, the cells are lysed, droplets formed, nucleosomes generated and imunoprecipitated, and DNA isolated from the nucleosomes, as described above (e.g., steps 1 to 11 are the same). However, at step 12 of FIG. 1B, after the DNA is released from the particle, the droplet containing the DNA is transferred to an aqueous phase, resulting in a pooling of DNA from all of the cells analyzed.

In some examples, the DNA in the aqueous phase is concentrated or purified, for example by using routine DNA purification methods (e.g., ethanol extraction, particles). In one example particles that bind to the DNA, such as a beads contain an appropriate nucleic acid molecule (e.g., one with a sequence complementary to the DNA in the droplet) are used. The resulting particles bound to the DNA that was on the nucleosome can be concentrated and washed as described above. The DNA on the particles can be eluted, and separated from the beads, and the resulting DNA analyzed.

The pooled DNA can then be analyzed (FIG. 1B, step 14). For example, the DNA can be then exposed to reagents that permit amplification (such as PCR reagents, e.g., Taq Polymerase, dNTPs, $MgCl_2$, primers) and/or reagents for sequencing.

Analysis of Non-Nucleosome DNA

The disclosure provides methods of analyzing non-nucleosomal DNA, instead of nucleosome DNA. For example, such methods can be used for DNase hypersensitivity (DHS) assays. The methods are similar to those described above, except that instead of keeping the DNA from the nucleosomes, the non-nucleosomal DNA is retained and analyzed.

As shown in FIGS. 1A and 1D, at step 1 (cell input), cells are encapsulated in droplets, for example by using a microfluidic droplet maker (e.g., within an aqueous environment contained within an oil). Typically, the cells are encapsulated within droplets at a density such that on average, each droplet contains one cell (or less). Thus, in some examples, individual droplets contain a single cell (that is, one cell per droplet), allowing for reactions to be performed on a single cell. This makes the need for large amounts of sample unnecessary. Within a droplet, a cell is exposed to additional reagents, such as those that permit lysis of the cell, and cleavage of DNA.

A liquid suspension containing single cells (or even a single cell) that have been crosslinked is introduced into the device, for example via injection. In some examples, the cells are present in a buffer. In one example, the suspension of crosslinked single cells is present in an aqueous phase.

The crosslinked cells are then incorporated or encapsulated into a microdroplet. As shown in FIG. 2A, droplets are formed by allowing an oil phase containing a surfactant to interact with or contact the aqueous cell-containing solution under conditions that permit a single cell to become encapsulated within a single droplet. In one example, the oil phase includes 2% (weight percentage) surfactant. Any biocompatible oil can be used, such as a, fluorinated oil (e.g., FC40, FC70, and the like). In one example the oil phase containing a surfactant includes or consists of 3M® Novec™ 7500 engineered fluid and fluorosurfactant. The interaction between the two different phases results in the formation of a droplet containing single cells.

As shown in FIGS. 1A and 1D, at step 2 (cell lysis), the cells contained within the droplets are exposed to one or more reagents that permit lysis of the cells within the droplet. For example, cells can be exposed to one or more enzymes or chemicals, such as one or more detergents (e.g., Triton, Triton X-100, saponin, NP-40, and the like) for at least 0.1 seconds, such as at least 0.5, or at least 1 second. In one example, the lysis buffer is 10 mM Tris-HCl, pH 7.5, 10 mM NaCl, 0.5% NP-40, and the incubation is for 1 to 60 seconds or 5 to 10 minutes. Another exemplary lysis buffer is 10 mM HEPES, pH 7.9, 1.5 mM $MgCl_2$, 10 mM KCl, 0.5% IGEPAL-CA630 and optionally 0.5 mM dithiothreitol (DTT). The cell lysis reagents are incubated with the droplets under conditions sufficient for the cells in the droplets to be lysed, such that the nucleosomes in the cell can be accessed. In some examples, the lysis buffer is allowed to interact with the cells in the droplets for at least 5 minutes, at least 10 minutes, at least 20 minutes, or at least 30 minutes, such as 5 to 60 minutes. In some examples, the droplets move or flow through the device and arrive at a stage of the device that permits their injection with a lysis buffer or permits introduction of a lysis buffer, for example by merging the cell-containing droplet with a lysis buffer droplet (e.g., see FIG. 4D). In some examples, the droplet is "mixed" by moving the droplet through a serpentine microchannel. In some examples, the lysis solution is added to the device with the cell suspension, to form a solution containing lysis buffer and crosslinked cell, and then this solution mixed with oil to form the droplets, thereby resulting in the lysis buffer becoming incorporated into the droplet containing the cell (e.g., see FIG. 2A).

Instead of digesting with a non-nucleosome-cleaving nuclease as shown in FIGS. 1A and 1D at step 3, instead the DNA of the lysed cells is exposed to a harsher nuclease, such as DNase I or DNase I. In one example, the nuclease is present in the buffer 20 mM Tris-HCl, pH 7.5, 15 mM NaCl, 60 mM KCl, 1 mM $CaCl_2$, or the buffer 20 mM Trizma hydrochloride, pH 7.5, 15 mM NaCl, 60 mM KCl, 5 mM $CaCl_2$, 0.15 mM spermine, 0.5 mM spermidine, and optionally 1% Pluronic and 0.1% BSA, which cleaves the DNA in the lysed cell into smaller fragments. The solution containing the enzyme is incubated with the droplets under conditions sufficient for the DNA in the droplets to be cleaved. In some examples, the solution containing the enzyme is allowed to interact with the cells in the droplets for at least 5 minutes, at least 10 minutes, at least 20 minutes, or at least 30 minutes, such as 5 to 60 minutes. In some examples, the droplets move or flow through the device and arrive at a stage of the device that permits their injection with a solution containing the enzyme or permits introduction of a solution containing the enzyme, for example by merging the cell-containing droplet with a nuclease-containing droplet (e.g., see FIG. 4D).

As shown in FIGS. 1A and 1D, at step 4, the enzyme reaction performed in step 3 is stopped (quenched), by adding an appropriate reagent to the droplet, such as EDTA. In one example, the quencher solution is 100 mM Tris-HCl, pH 8, 20 mM EDTA, 200 mM NaCl, 2% Triton-X 100, 0.2% Sodium dodecyl sulfate. The quencher solution is incubated with the droplets under conditions sufficient to significantly reduce the enzyme activity and reduce DNA cleavage. In some examples, quencher solution is allowed to interact with the cells in the droplets for at least 5 minutes, at least 10 minutes, at least 20 minutes, or at least 30 minutes, such as 5 to 60 minutes. In some examples, the droplets move or flow through the device and arrive at a stage of the device that permits their injection with a quencher solution or permits introduction of a quencher solution, for example by merging the cell-containing droplet with a quencher-containing droplet (e.g., see FIG. 4D).

The resulting droplets containing nucleosomes and free DNA (non-nucleosome DNA) are then subjected to immunoprecipitation, such as step 5 in FIG. 1A (aim 2, step 3 of FIG. 1D). The nucleosome(s) in each droplet (and thus the nucleosome from a single cell) is captured using immunoprecipitation using one or more reagents that specifically bind to one or more histone proteins (such as 1, 2, 3 or 4 of H2A, H2B, H3, and H4), their variants, covalent modifications, transcription factors, and non-histone proteins, as well as DNA modifications, allowing the unlabeled chromatin in each droplet to be isolated in subsequent steps for DHS analysis. For example antibodies, antibody fragments, or other specific binding reagents (such as a functional nucleic acid, e.g., aptamer, DNAzyme, RNAzyme, aptazyme, and the like) can be used. In a specific example, an antibody that generally targets all nucleosomes is used (e.g., a specific binding agent that targets H4 or H2B or using specific binding agents that do not distinguish e.g., between H3 variants).

The specific binding reagent is present on a solid support, such as a bead, microsphere, or other particle. Methods of attaching or immobilizing a specific binding agent to a solid support are known. In some examples, the solid support is composed of metal (e.g., gold, silver, platinum), metal (e.g., zinc oxide, zinc sulfide, copper sulfide, cadmium sulfide), non-metal (e.g., silica or a polymer), or magnetic materials (e.g., iron oxide, manganese oxide). In some examples the solid support is a latex or glass bead. In one example, the solid support is magnetic bead. The size of the solid support is not critical; exemplary sizes include beads that are 5 nm to 5000 nm in diameter, such as 1 to 100 nm, 1 to 50 nm, 1 to 10 nm, 2 to 20 nm, or 5 to 25 nm. In one example such particles are about 1 µm in diameter.

Thus, the method includes contacting the cells in the droplets that were lysed and contacted with the non-nucleosome-cleaving nuclease and quencher, with particles containing immobilized binding agents that are specific for a histone protein, or a histone variant, histone modification, nonhistone protein, transcription factor, or DNA modification, for example by introducing such particles into the droplet containing the nucleosomes. The particles are incubated with the droplets under conditions sufficient for targets in the droplet to bind to the specific binding agent on the particles. In some examples, the particles are allowed to interact with the nucleosomes in the droplets for at least 5 minutes, at least 10 minutes, at least 20 minutes, or at least 30 minutes, such as 5 to 60 minutes.

To capture the unbound chromatin, the droplet-containing particles are subjected to a series of concentration steps and washes, such as with a salt-containing solution. As shown in FIG. 1A, at step 6 (bead concentration) (and steps 4-5 in aim 2 of FIG. 1D), the particles (which will have nucleosome(s) bound to them) are concentrated, and the size of the droplet is reduced by at least 10%, at least 20%, at least 25%, at least 30%, at least 40%, at least 50%, at least 60%, at least 66%, at least 75%, at least 80%, or at least 90% (such as 25 to 75%) of the volume of the droplet is removed. However, instead of keeping the portion of the droplet containing the solid support as described above, the portion of the droplet containing the non-nucleosomal DNA is retained.

For example, the droplet can be treated to generate a portion of the droplet containing unbound non-nucleosomal DNA and another portion of the droplet containing the solid support bound to the target(s). These portions of the droplet can be treated or "split" to retain the portion of the droplet containing non-nucleosomal DNA, can discarding leaving the portion of the droplet containing the solid support bound to nucleosomes. In some examples, at least 10%, at least 20%, at least 40%, at least 50%, at least 75%, at least 80%, at least 90%, at least 95%, or at least 99% (such as 25 to 75%) of the portion of the droplet containing the solid support is removed, thereby resulting in a smaller droplet containing the non-nucleosomal DNA. For example, if the particles are magnetic, then the droplets can be exposed to a magnetic force, and the droplet split, so that the portion of the droplets containing the particles is divided or separated from the portion of the droplets not containing the particles. Other methods of separation can be used, such as centrifugal forces, which will precipitate the particles, or flow cytometry methods, which can collect the portion of the droplet containing the non-nucleosomal DNA.

The resulting portion of the droplet containing non-nucleosomal DNA can then be treated to capture the DNA, for example using a solid support. For DNA can be isolated using solid supports and eluted (e.g., generally shown in steps 7 to 10 of FIG. 1D). The non-nucleosomal DNA in the droplet can be concentrated or purified, for example by introducing solid supports that bind to the DNA, such as a beads containing an appropriate nucleic acid molecule (e.g., one with a sequence complementary to the DNA in the droplet or using other appropriate reagents (e.g., Dynabeads from Invitrogen) (e.g., similar to step 7 of FIG. 1D). The resulting solid supports bound to the non-nucleosomal DNA can be concentrated and washed as described above (e.g., similar to steps 8-9 of FIG. 1D). The non-nucleosomal DNA on the solid support can be eluted, and separated from the solid support (e.g., similar to step 10 of FIG. 1D), and the resulting DNA-containing droplet collected and analyzed (e.g., similar to step 11-12 of FIG. 1D). In some examples, a plurality of non-nucleosomal DNA droplets are combined (e.g., similar to step 12 of FIG. 1B) instead of being analyzed separately. Thus, in some examples, the portion of the droplet containing the non-nucleosomal DNA is incubated with a second solid support that binds to the DNA, for example by using an automated injection means, such as an injector and a means to apply a voltage to the droplet (e.g., electric field generator), thereby allowing the second solid support containing solution to merge with the droplet. After allowing for an adequate amount of binding, the solid supports can be optionally washed, and the bound DNA eluted, and the solid supports separated from the eluted DNA (e.g., by using methods that allow for concentration of the second solid support (e.g., magnet, centrifugal forces, flow cytometry) and a means that allows for removal of part of the droplet (e.g., means to apply a voltage)). In one example, the portion of the droplet containing the DNA is collected. The resulting non-nucleosomal DNA from a single cell (or from a plurality of cells) can then be purified and concentrated if desired, and analyzed (e.g., using PCR and/or sequencing). In some examples, a plurality of single cells within a plurality of single droplets are analyzed contemporaneously.

The non-nucleosomal DNA-containing droplet can then be analyzed. The DNA (which may still be present in a droplet) can be then exposed to reagents that permit amplification (such as PCR reagents, e.g., Taq Polymerase, dNTPs, primers, $MgCl_2$) and/or reagents for sequencing. Exemplary methods of amplification include PCR, such as real-time (quantitative) PCR, digital droplet PCR (ddPCR). For example, the DNA can be analyzed using the Bio-Rad QX-100 droplet PCR system and/or the Illumina HiSeq 2000 system (or other equivalent).

In one example, the volume added to the droplet to provide the necessary reagents is about 100 pL, about 150 pL or about 200 pL, such as 100 to 200 pL.

Automated Generation of Nucleosomes

An overview of one embodiment of the method is provided in FIG. 1C. This example of the method includes two general modules: (1) cell lysis and chromatin shearing to generate nucleosomes from a plurality of cells which are pooled in an aqueous phase, and (2) epigenetic analysis of the pooled nucleosomes (not shown). The goal of module 1 is to obtain nuclear material of a specific size (e.g., mixture of mono-, di-, and/or trinucleosomes), and the goal of module 2 is to analyze the nucleosomes, for example using additional ChIP steps. This example allows the initial steps of ChIP or other epigenetic analysis to be automated.

Cell Lysis and Chromatin Shearing

As shown in FIG. 1C, at step 1 (cell input), cells are encapsulated in droplets, for example by using a microfluidic droplet maker (e.g., within an aqueous environment contained within an oil). Typically, the cells are encapsulated within droplets at a density such that on average, each droplet contains one cell (or less). Thus, in some examples, individual droplets contain a single cell (that is, one cell per droplet), allowing for reactions to be performed on a single cell. This makes the need for large amounts of sample unnecessary. Within a droplet, a cell is exposed to additional reagents, such as those that permit lysis of the cell, and cleavage of DNA.

A liquid suspension containing single cells (or even a single cell) that have been crosslinked is introduced into the device, for example via injection. In some examples, the cells are present in a buffer. In one example, the suspension of crosslinked single cells is present in an aqueous phase.

The crosslinked cells are then incorporated or encapsulated into a microdroplet. As shown in FIG. 2A, droplets are formed by allowing an oil phase containing a surfactant to interact with or contact the aqueous cell-containing solution under conditions that permit a single cell to become encapsulated within a single droplet. In one example, the oil phase includes 2% (weight percentage) surfactant. Any biocompatible oil can be used, such as a, fluorinated oil (e.g., FC40, FC70, and the like). In one example the oil phase containing a surfactant includes or consists of 3M® Novec™ 7500 engineered fluid and fluorosurfactant. The interaction between the two different phases results in the formation of a droplet containing single cells.

As shown in FIG. 1C, at step 2 (cell lysis), the cells contained within the droplets are exposed to one or more reagents that permit lysis of the cells within the droplet. For example, cells can be exposed to one or more enzymes or chemicals, such as one or more detergents (e.g., Triton, Triton X-100, saponin, NP-40, and the like) for at least 0.1 seconds, such as at least 0.5, or at least 1 second. In one example, the lysis buffer is 10 mM Tris-HCl, pH 7.5, 10 mM NaCl, 0.5% NP-40, and the incubation is for 1 to 60 seconds or 5 to 10 minutes. Another exemplary lysis buffer is 10 mM HEPES, pH 7.9, 1.5 mM $MgCl_2$, 10 mM KCl, 0.5% IGEPAL-CA630 and optionally 0.5 mM dithiothreitol (DTT). The cell lysis reagents are incubated with the droplets under conditions sufficient for the cells in the droplets to be lysed, such that the nucleosomes in the cell can be accessed. In some examples, the lysis buffer is allowed to interact with the cells in the droplets for at least 5 minutes, at least 10 minutes, at least 20 minutes, or at least 30 minutes, such as 5 to 60 minutes. In some examples, the droplets move or flow through the device and arrive at a stage of the device that permits their injection with a lysis buffer or permits introduction of a lysis buffer, for example by merging the cell-containing droplet with a lysis buffer droplet (e.g., see FIG. 4D). In some examples, the droplet is "mixed" by moving the droplet through a serpentine microchannel. In some examples, the lysis solution is added to the device with the cell suspension, to form a solution containing lysis buffer and crosslinked cell, and then this solution mixed with oil to form the droplets, thereby resulting in the lysis buffer becoming incorporated into the droplet containing the cell (e.g., see FIG. 2A).

As shown in FIG. 1C, at step 3 (MNase digestion), the DNA of the lysed cells is exposed to an enzyme, such as a non-nucleosome-cleaving nuclease or other enzyme able to cleave the DNA without destroying epigenetic information. In one example, the enzyme is micrococcal nuclease (MNase). In another example, the enzyme is DNase I, DNase II, or Tn5 transposase. In one example, the nuclease is present in the buffer 20 mM Tris-HCl, pH 7.5, 15 mM NaCl, 60 mM KCl, 1 mM $CaCl_2$, or the buffer 20 mM Trizma hydrochloride, pH 7.5, 15 mM NaCl, 60 mM KCl, 5 mM $CaCl_2$, 0.15 mM spermine, 0.5 mM spermidine, and optionally 1% Pluronic and 0.1% BSA, which cleaves the DNA released from the lysed cell into smaller fragments, without substantially affecting those portions of the DNA that interact with the histones within the nucleosome structures. The solution containing the enzyme is incubated with the droplets under conditions sufficient for the DNA in the droplets to be cleaved. In some examples, the solution containing the enzyme is allowed to interact with the cells in the droplets for at least 5 minutes, at least 10 minutes, at least 20 minutes, or at least 30 minutes, such as 5 to 60 minutes. In some examples, the droplets move or flow through the device and arrive at a stage of the device that permits their injection with a solution containing the enzyme or permits introduction of a solution containing the enzyme, for example by merging the cell-containing droplet with a nuclease-containing droplet (e.g., see FIG. 4D).

In some examples, the enzyme (e.g., MNase) concentration and reaction time achieves (i) a ≥85% mono+dinucleosome yield (e.g., determined by quantitative fragment analysis) from nuclei as input; (ii) demonstrate single cell droplet encapsulation with ≥75% efficacy (e.g., determined by microscopy); (iii) demonstrate ≥70% mono+dinucleosome yield from droplet-encapsulated single cells (e.g., by fragment analysis); and (iv) directly benchmark upscaled on- vs. off-chip MNase in terms of broad genomic accessibility using MNase-qPCR and MNase-seq and quantitative criteria.

As shown in FIG. 1C, at step 4 (Digestion quenching and Droplet Extraction), the enzyme reaction performed in step 3 is stopped (quenched), by allowing the droplets move into a portion of the device containing an aqueous phase (such as one containing an EDTA solution) to inhibit and dilute out the enzyme (e.g., MNase or other nuclease). In one example, the quencher solution is 100 mM Tris-HCl, pH 8, 20 mM EDTA, 200 mM NaCl, 2% Triton-X 100, 0.2% Sodium dodecyl sulfate. The resulting nucleosomes in the aqueous phase can be then analyzed in bulk, for example using additional ChIP. For example, DNA and/or proteins associated with the nucleosomes can be analyzed for epigenetic information (e.g., amplified, sequenced). Fewer cells are needed than with conventional ChIP methods, as the generation of the nucleosomes is automated.

In one example, the generated nucleosomes are analyzed using standard ChIP methods. For example, the method can include adding to the nucleosomes the antibody targeting a histone, histone variant, histone modification, nonhistone protein, transcription factor or DNA modification or non-specific IgG (as control). Protein G-agarose beads are added, and the reaction incubated (e.g., for 1-4 hours). The beads are washed, and the bound chromatin eluted and reverse-crosslinked (e.g., 65° C. overnight). The free DNA is then purified (e.g., using Min-Elute PCR Purification kit (Qiagen)) after treatment with RNase A and proteinase K. ChIP quality is analyzed by targeted real-time PCR using primers designed to identify genomic regions known to bind to or lack the immunoprecipitated target protein. Following verification of at least 5-fold enrichment of positive vs. negative loci, high-throughput sequencing libraries are prepared (e.g., from 10 ng of ChIP and input DNA). The ChIP-seq libraries are sequenced.

Exemplary Cells

The cells analyzed with the disclosed methods and devices can be a eukaryotic cell, such as a mammalian cell, fish cell, amphibian cell, invertebrate cell, or a bird cell (e.g., human, dog, cat, cow, chicken, mouse, zebra fish, fruit fly, frog, and the like), or plant cell, yeast cell or protozoan cell. In some examples, the cell analyzed is a cancer cell, a stem cell (such as a cancer stem cell), or a circulating tumor or cancer cell. In some examples, the cell analyzed is a mesenchymal or epithelial cell. In some examples, the cell analyzed is a cell that is a marker of a disease, such as various leukocytes in leukemia. Cells harvested from any type of biopsy (liver, kidney, muscle, skin, bone marrow, intestine, bronchial lavage, etc.) or biological fluid can also be investigated using the methods described herein. In some examples, the cell is not cultured (e.g., not subjected to tissue culture) prior to analysis with the disclosed methods.

In one example the cells to be analyzed are labeled, for example to permit their detection within a droplet. Such methods can be used to screen droplets for the presence of cells, for example to determine how many cells are present in each droplet. In some examples, the methods provided herein include removal of droplets containing more than one cell, and/or droplets containing no cells, for example automatedly (e.g., by applying a voltage to the undesired droplet such that it is transferred to an extraction or waste portion of the device). Such steps can be performed at any time during the method, such as after droplet formation (e.g., after step 1 of FIG. 1A). Methods of labeling cells are routine, and can include the use of labeled antibodies specific for a protein found in or on the cell to be analyzed, DAPI to label the nucleus, nucleic acid probes that include a label and which can specifically hybridize to a nucleic acid present in the cell to be analyzed, or any other label that permits detection of a cell (e.g., using microscopy, spectrometry, or flow cytometry). In one example, cells are labeled using green fluorescent protein.

In some examples, the methods include the step of obtaining the sample containing cells to be analyzed. Methods of obtaining cells from a subject or biological tissue are routine. In some the cells or tissues can be obtained from a healthy subject, or one that is diseased or suspected of being diseased. In one example, blood cells from a subject are removed and analyzed using the methods provided herein to determine epigenetic differences or changes in the epigenetic profile of those cells, for example to determine if the subject is healthy or has a disease, for example, if the subject has cancer (e.g., by detecting cancer cells within the blood). In some cases, cells from a tumor (e.g., biopsy) are analyzed, and the epigenetic profile of the tumor determined. For instance, the cells can be examined to determine if any of the cells are cancer stem cells.

Methods of obtaining a single cell or a suspension of single cells are known in the art, and can include treatment with enzymes (such as collagenase used in tissues, trypsin used in cell cultures) or agitation, laser-capture, or combinations thereof.

The cells to be analyzed are treated with one or more agents that crosslink DNA-protein complexes. Crosslinking is the process of chemically joining two or more molecules by a covalent bond. Crosslinking reagents (or crosslinkers) contain two or more reactive ends capable of chemically attaching to specific functional groups (primary amines, sulfhydryls, etc.) on proteins or other molecules. Such methods are known in the art, and exemplary crosslinkers that can be used include formaldehyde, such as 1% formaldehyde. In one example, cells or homogenized tissues are cross-linked with 1% formaldehyde for 10 minutes, followed by quenching with 125 mM glycine for 5 minutes at room temperature. Fixed cells can be washed, for example with Tris-buffered saline (TBS) or PBS, and resuspended in buffer (e.g., at a density optimized for cell encapsulation). In one examples, cells are suspended at about $1 \times 10^3$ cells/ml, $1 \times 10^4$ cells/ml, $1 \times 10^5$ cells/ml, $1 \times 10^6$ cells/ml or $1 \times 10^7$ cells/ml, for example in PBS.

Formation and Manipulation of Droplets

Any methods for generating droplet-encapsulated cells can be used. In one example, the deterministic cell-in-droplet method (37-40) is used. This design incorporates a curved microchannel to introduce a Dean force, causing cells to spatially order with respect to one another. The channel geometry and flow rates can be designed to give cell spacings matched to droplet generation rates, hence achieving a high yield of droplets encapsulating a single cell. In one example the device generates droplets at a frequency of ~1000 Hz, resulting in single-cell encapsulation. In some examples, at least 75% of the droplets have a single cell.

In one example, a junction of channels is used to create the droplets. The junction may be, for instance, a T-junction, a K-junction (e.g., see 24 of FIG. 6A), a V-junction, a Y-junction, a channel-within-a-channel junction (e.g., in a coaxial arrangement, or comprising an inner channel and an outer channel surrounding at least a portion of the inner channel), a cross (or "X") junction, a flow-focus junction, or any other suitable junction for creating droplets (e.g., see PCT/US2004/010903, PCT/US2013/029123, PCT/US2003/02054). In some embodiments, the junction may be configured and arranged to produce substantially monodisperse droplets. In a specific example, the junction is a K-junction (see 24 of FIG. 6A).

In some examples, the fluid containing the cells is substantially immiscible with the carrying fluid of the droplets. Two immiscible liquids are used to form droplets. In one example oil with surfactants is the continuous phase; hydrophilic phase (buffer) with cells is the dispersed phase. The dispersed phase is cut off into droplets by the continuous phase. For example, the cell solution can be hydrophilic or aqueous, while the droplet fluid may be hydrophobic or an "oil," or vice versa. Typically, a "hydrophilic" fluid is one that is miscible with pure water, while a "hydrophobic" fluid is a fluid that is not miscible with pure water. The term "oil" merely refers to a fluid that is hydrophobic and not miscible in water. Thus, the oil can be a hydrocarbon in some embodiments, but in other embodiments, the oil can be (or include) other hydrophobic fluids (for example, octanol). The hydrophilic or aqueous fluid need not be pure water. For example, the hydrophilic fluid may be an aqueous solution, for example, a buffer solution, a solution containing a dissolved salt, or the like. A hydrophilic fluid may also be, or include, for example, ethanol or other liquids that are miscible in water, e.g., instead of or in addition to water.

The formed droplets containing the cells can be in a state of flow through the device. Thus, in some examples the droplets are not anchored or attached to the walls/surface of the channel in which the droplet is present (e.g., using magnetic tweezers other interactions that would allow, for example, droplets to attach to the wall of the channel in which the droplet is present). In some examples, none of the reaction steps used to generate nucleosomes (FIG. 1C) or DNA from nucleosomes (steps 1-11 of FIG. 1A, or steps 1-11 of FIG. 1B) includes anchoring or attaching droplets to the walls/surface of the channel in which the droplet is present. In some examples the droplets touch one another in the channel (e.g., microchannel) but do not fuse with one another.

In addition, the droplets ensure that the cells in the droplets (or parts of the cells, such as nucleosomes, histones, DNA from the nucleosomes) do not touch or come in contract with the walls or inner surface of the channels (e.g., microfluidic channels) of the device. Thus, one or more of the reaction steps can be performed within the droplet itself (see FIGS. 1A-1C). In some examples, none of the reaction steps used to generate nucleosomes (FIG. 1C) or DNA from nucleosomes (steps 1-11 of FIG. 1A, or steps 1-11 of FIG. 1B) includes anchoring or attaching cells (or parts of the cells, such as nucleosomes, histones, DNA from the nucleosomes) to the walls/surface of the channel in which the droplet is present (e.g., using magnetic tweezers other interactions that would allow, for example, nucleosomes, histones, or DNA to attach to the wall of the channel in which the droplet is present).

In some examples, the droplets have an average dimension or diameter of less than about 1 mm, less than about 500 micrometers, less than about 300 micrometers, less than about 200 micrometers, less than about 100 micrometers, less than about 75 micrometers, less than about 50 micrometers, less than about 30 micrometers, less than about 25 micrometers, less than about 10 micrometers, less than about 5 micrometers, less than about 3 micrometers, or less than about 1 micrometer, such as 7 to 100, 7 to 25, or 7 to 50 micrometers. In some examples, the average diameter of the droplet is at least about 1 micrometer, at least about 2 micrometers, at least 20 about 3 micrometers, at least about 5 micrometers, at least about 10 micrometers, at least about 15 micrometers, or at least about 20 micrometers. The droplets can be spherical or non-spherical. The average diameter or dimension of a droplet, if the droplet is non-spherical, may be taken as the diameter of a perfect sphere having the same volume as the non-spherical droplet. In one example, the droplets have an average volume of less than about 1000 pl, less than about 700 pl, less than about 500 pl, less than about 400 pl, or less than about 200 pl, such as about 50 to 1000 pl, about 100 to 500 pl, about 100 to 200 pl, about 70 to 150 pl, or about 150 to 250 pl, such as 200 pl.

In one example, the oil phase used to generate the cell-containing droplet includes 3M™ Novec™ 7500 Engineered Fluid (The 3M Company, Maplewood, Minn.) with 2% by weight poly(ethylene glycol) di-(krytox-FSH amide) (Ran Biotechnologies, Inc., Beverly, Mass.) added as a surfactant to stabilize droplets. Aqueous dye can also be included in the droplet solution.

The geometries and flow rates of the device can be controlled to generate droplets of any desired size (e.g., for larger cells larger droplets are used). In one example, the contents of the droplet are thoroughly mixed by passing through a serpentine channel before moving into a delay channel (for example to allow the cells, nucleosomes, solid support, and the like, to incubate with desired reagents for a desired amount of time). The repeatedly-constricted delay channel geometry, in which the periodic constrictions are roughly the size of a droplet, can help ensure equal transit/reaction times. In one example, the overall length of the delay channel is designed to give a 10 minute incubation time.

The droplets containing the cells (or parts thereof, such as nucleosomes, histones, and DNA) can be present in a microfluidic channel, such as one that has a curved or serpentine shape, or one that includes parallel microfluidic channels that can interact with one another. In one example, the microfluidic channel is no more than 500 microns in diameter, such as 1 to 500 microns, 10 to 200 microns, or 20 to 100 microns in diameter. In one example, the microfluidic channel is made of plastic, silicone, polydimethylsiloxane (PDMS), or glass. In some examples, the channel is pretreated to increase its hydrophobicity, for example with 1% by volume (tridecafluoro-1,1,2,2-tetrahydrooctyl)trichlorosilane in Fluoroinert FC-40 carrier fluid.

The microfluidic droplets containing cells can be used to keep the cells of a plurality of cells separate and identifiable, such that epigenetic or genetic differences between the different cells can be identified. Thus, a plurality of cells can be contained within a plurality of droplets. In some examples, the encapsulation rate achieves an average density of about 1 cell/droplet, or less, such as less than about 0.95 cells/droplet, less than about 0.9 cells/droplet, less than about 0.8 cells/droplet, less than about 0.7 cells/droplet, less than about 0.6 cells/droplet, less than about 0.5 cells/droplet, less than about 0.4 cells/droplet, less than about 0.3 cells/droplet, or less than about 0.2 cells/droplet, such as 0.1 to 1 cell/droplet. As a result, in some examples, the cells are contained such that no more than about 25%, no more than about 15%, no more than about 10% no more than about 5%, no more than about 3%, no more than about 1%, or no more than 0.1% of the droplets contains more than one cell. In some examples, the number of cells per droplet is not critical, as the DNA from the nucleosomes from a plurality of cells (e.g., FIG. 1B), or the nucleosomes from a plurality of cells (e.g., FIG. 1C), are pooled.

In some cases, the cells may be encapsulated within the droplets at a relatively high rate. For example, the rate of cell encapsulation in droplets may be at least about 10 cells/s, at least about 30 cells/s, at least about 100 cells/s, at least about 300 cells/s, at 10 least about 1,000 cells/s, at least about 3,000 cells/s, at least about 10,000 cells/s, at least about 30,000 cells/s, at least about 100,000 cells/s, at least about 300,000 cells/s, or at least about $10^6$ cells/s. The droplets can be substantially monodisperse.

In one example, the flow rates can be about 8 µL/min for oil, 2 µL/min for cells and 2 µL/min for lysis buffer to produce droplets of the volume of (95.60±7.13) pL, and 1 µL/min for MNase (or other nuclease) or other materials to be injected into droplets. In one example, the flow rate for a solution to extract the passing droplets can be about 8 µL/min (step 4, FIG. 1C). In one example the flow rates are about 3 to 15 µL/min.

In one example, microfluidic devices include one or more injectors or syringes (e.g., Hamilton Gastight Syringes (Reno, Nev.) connected to a pump (e.g., Harvard Plus 1000 Syringe Pumps from Harvard Bioscience Inc. (Holliston, Mass.) allow for materials to be introduced into the device and/or droplets in the device. The flow rates for oil, cells and lysis buffer (e.g., "droplet formation" in FIG. 2A) can be tunable to obtain droplets with different sizes. The flow rate for pico-, nano-, or micro-injecting reagents (such as a solution containing a nuclease, solid particles that can specifically bind to nucleosomes, wash buffers, and the like) into the droplets, as well as the flow rate for removing portions of droplets or extracting droplets to a different portion of the device (e.g., waste or different microfluidic channel) can also be tunable and depend on the droplet formation rates. In some examples, the volume delivered into the droplets does not exceed the volume of the droplet (e.g., a volume of 75% or less, 60% or less, 50% or less, or 25% or less is injected). For example if the droplet is 200 pl, less than 200 pl is injected (e.g., a volume of 100 pl is injected). In one example, fluids are delivered into the devices using PTFE tubing (such as #30 AWG PTFE tubing, Cole Parmer, Vernon Hills, Ill.) inserted into inlets from a vial pressurized with $N_2$ or other inert gas. Pressure delivery to the vials can be controlled by solenoid valves. Valves can be actuated, for example using a NI PCIe-6251 Multifunction Data Acquisition device (National Instruments, Austin, Tex.) with an SCB-68 Shielded I/O Connector Block (National Instruments, Austin, Tex.). In one example, oil for droplet formation is delivered at 65 kPa. In some examples, the electric field is supplied to devices via 0.5 M NaCl in electrode channels using a regulated power supply (e.g., Tenma 72-6628 DC Regulated Power Supply, MCM Electronics, Dayton, Ohio), which can include a DC to AC converter.

Microfluidics-Based Chromatin ImmunoCapture Platform

Provided herein is a microfluidics platform which can be used to perform genome-wide ChIP analysis on a single cell. As shown in FIG. 1A, at step 1, single cells are encapsulated in droplets, allowing for reactions to be performed on a single cell. This makes the need for large amounts of sample unnecessary. In some examples, the cell analyzed is a cancer cell, a stem cell (such as a cancer stem cell), or a circulating tumor or cancer cell. Other exemplary examples are provided herein.

Figure 6A:
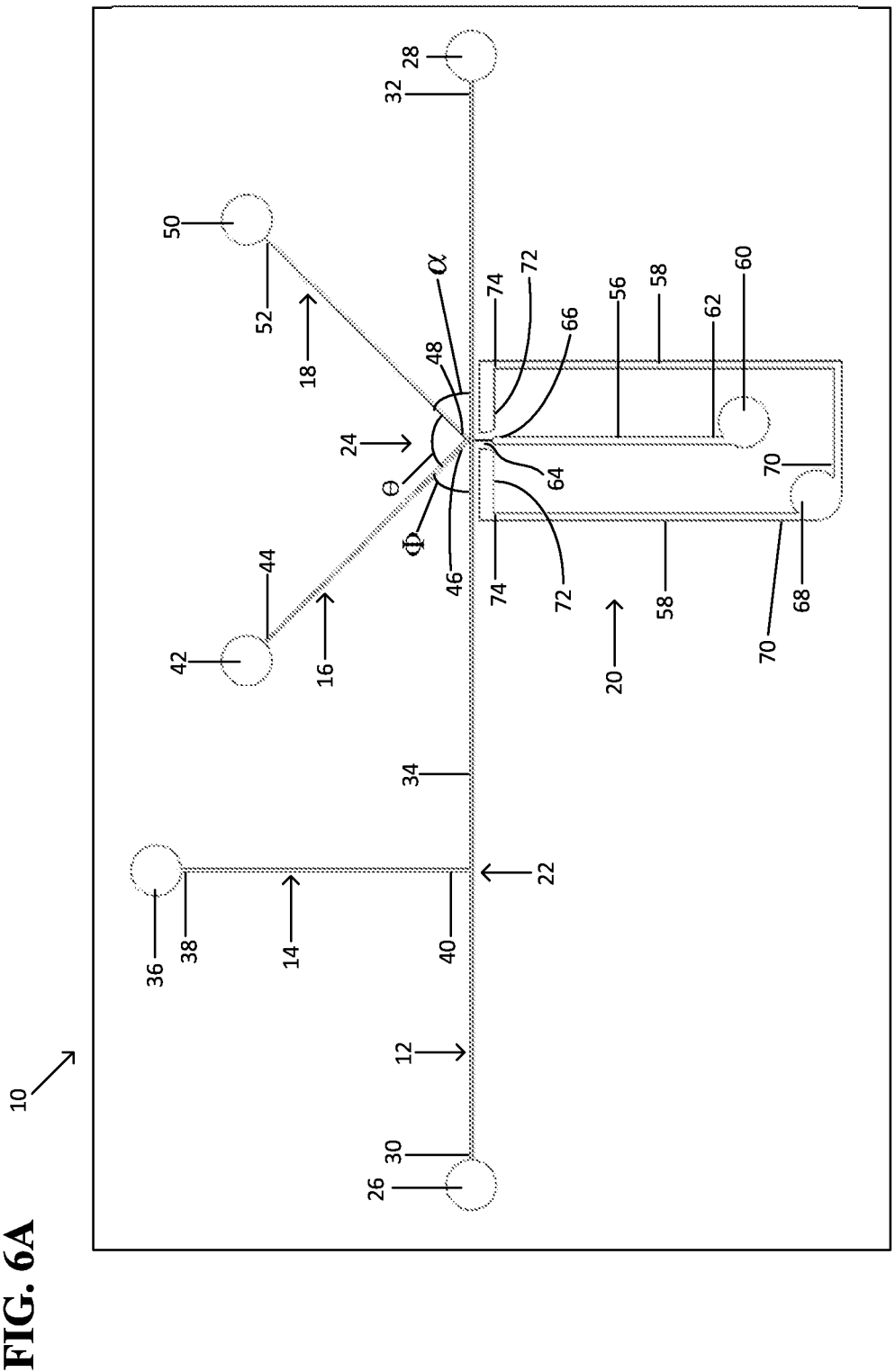
FIG. 6A is a schematic of a microfluidic device, according to one embodiment.
Figure 6D:
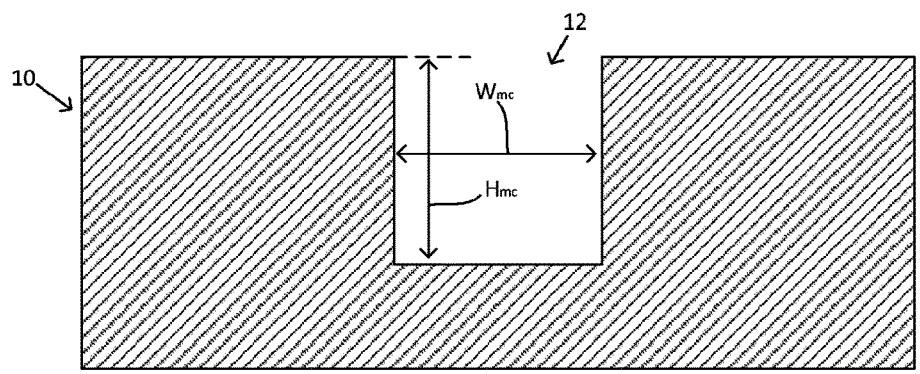
FIGS. 6D-6G are various partial cross-sectional views of the microfluidic device.

Referring to FIG. 6A, there is shown an example of a microfluidic device 10 comprising a K-junction, according to one embodiment. The microfluidic device 10 can comprise a main channel 12, a droplet formation channel 14, a first side channel portion 16, a second side channel portion 18, and an electric field generator portion 20. The first, side channel 14 can, for example, be connected to the main channel 12 by forming a T-junction 22 between the first side channel 14 and the main channel 12, as further described below. The first and the second side channels 16, 18 can, for example, each be connected to the main channel portion 12 to each other by forming a K-junction 24 between the main channel 12 and the first and second side channels 16, 18, as further described below. The electrical field generator portion 20 can be disposed near or adjacent to the K-junction 24 formed by the main channel 12 and the first and second side channels 16, 18, as further described below.

Exemplary Description of a Main Channel

The main channel 12 can comprise a first port or opening 26 and a second port or opening 28. The first port 26 can be connected to a first end portion 30 of the main channel 12, and the second port 28 can be connected to a second end portion 32 of the main channel 12. The first and second ends 30, 32 of the main channel 12 can be separated by an intermediate portion 34 of the main channel 12. The T-junction 22 and the K-junction 24 can be spaced apart (relative to each other) and disposed on intermediate portion 34 of the main channel 12. For example, the T-junction 22 can be disposed on the intermediate portion 34 towards the first end 30, relative to the K-junction 34.

The main channel 12 can be configured with various dimensions and/or cross-sectional shapes. For example, as best shown in FIG. 1D, the main channel 12 has a generally rectangular cross-sectional shape with a height $H_{mc}$ and a width $W_{mc}$. In some embodiments, the height $H_{mc}$ can be about 10 µm to 200 µm and the width $W_{mc}$ can be about 10 µm to about 200 µm. In preferred embodiments, the height $H_{mc}$ can be about 30 µm to about 50 µm and the width $W_{mc}$ can be about 30 µm to about 50 µm. In the illustrated embodiment, for example, the height $H_{mc}$ can be about 40 µm and the width $W_{mc}$ can be about 40 µm.

The main channel 12 can also comprise a length (i.e., the distance from the first end 30 to the second end 32 of the main channel 12). The length can vary depending on the application. In the illustrated embodiment of FIG. 6A, for example, the length of the main channel 12 is about 15 mm.

Exemplary Description of a Droplet Formation Channel

The droplet formation channel 14 can comprise a third port 36 which is connected to a first end 38 of the droplet formation channel 14. A second end 40 of the droplet formation channel 14 can be connected to the main channel 12 at the T-junction 22. The droplet formation channel 14 can be configured with various dimensions and/or cross-sectional shapes, similar to the main channel 12. Although not shown, the droplet formation channel can have a generally rectangular cross-sectional shape with a height and a width. In some embodiments, the droplet formation channel 14 can, for example, have height of about 10 µm to 200 µm and a width of about 10 µm to about 200 µm. In some embodiments, the droplet formation channel 14 can, for example, have a height of about 30 µm to about 50 µm and a width of about 30 µm to about 50 µm. In the illustrated embodiment, for example, the droplet formation channel 14 has a height of about 40 µm and the width of about 40 µm.

The droplet formation channel 14 can also comprise a length (i.e., the distance from the first end 38 to the second end 40 of the droplet formation channel 14). The length can vary depending on the application. In the illustrated embodiment of FIG. 1A, for example, the length of the droplet formation channel 14 is about 4 mm.

Exemplary Description of a First Side Channel

A K-junction can be formed of at least two side channels, such as first side channel 16 and second side channel 18 as shown in FIG. 6A.

The first side channel 16 can comprise a fourth port 42 which is connected to a first end 44 of the first side channel 16. A second end 46 of the first side channel 16 can be connected to the intermediate portion 34 of the main channel 12 and to a second end 48 of the third side channel 18, as best shown in FIG. 6C and further described below.

Figure 6E:
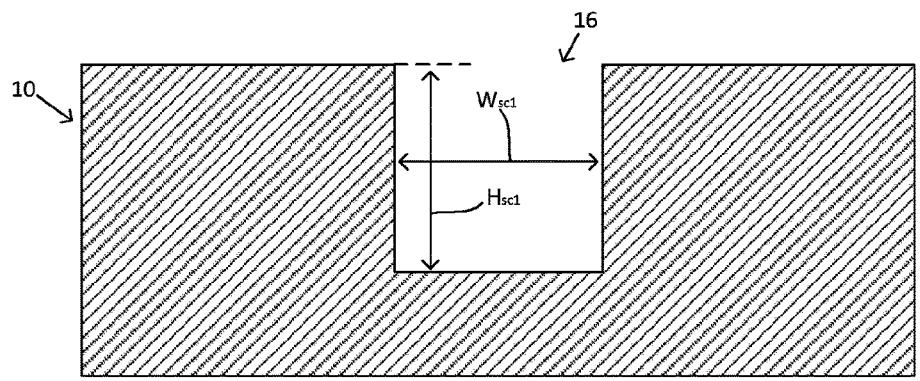
Figure 6F:
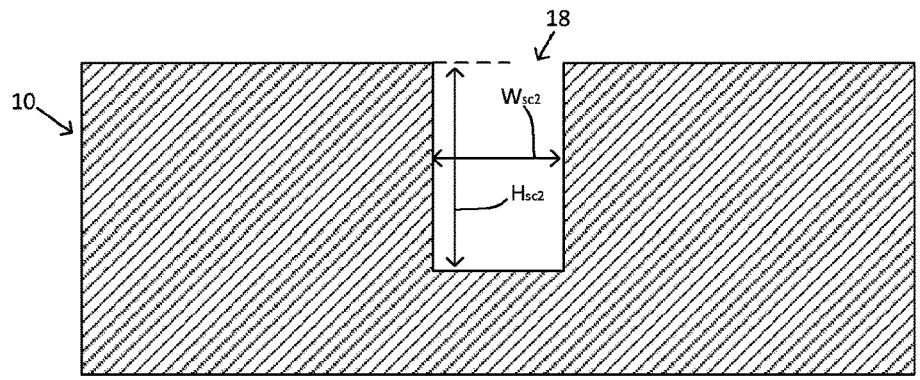

The first side channel 16 can be configured with various dimensions and/or cross-sectional shapes. For example, as best shown in FIG. 6E, the first side channel 16 has a generally rectangular cross-sectional shape with a height $H_{sc1}$ and a width $W_{sc1}$. In some embodiments, the height $H_{sc1}$ can be about 10 μm to about 200 μm and the width $W_{sc1}$ can be about 10 μm to about 200 μm. In preferred embodiments, the height $H_{sc1}$ can be about 30 μm to about 50 μm and the width $W_{sc1}$ can be about 30 μm to about 50 μm. In one particular embodiment, the height $H_{sc1}$ can be about 40 μm and the width $W_{sc1}$ can be about 40 μm. In the illustrated embodiment, for example, the height $H_{sc1}$ is about 40 μm and the width $W_{sc1}$ is about 40 μm.

The first side channel 16 can also comprise a length (i.e., the distance from the first end 44 to the second end 46 of the first side channel 16). The length can vary depending on the application. In the illustrated embodiment of FIG. 6A, the length of the first side channel 16 is about 4 mm.

Exemplary Description of a Second Side Channel

The second side channel 18 can comprise a fifth port 50 which is connected to a first end 52 of the second side channel 18. As mentioned above, the second end 48 of the second side channel 18 can be connected to the intermediate portion 34 of the main channel 12 and to a second end 46 of the first side channel 16, as best shown in FIG. 6C and further described below.

The second side channel 18 can be configured with various dimensions and/or cross-sectional shapes. For example, as best shown in FIG. 1F, the second side channel 18 has a generally rectangular cross-sectional shape with a height $H_{sc2}$ and a width $W_{sc2}$. In some embodiments, the height $H_{sc2}$ can be about 10 μm to about 200 μm and the width $W_{sc2}$ can be about 10 μm to about 200 μm. In preferred embodiments, the height $H_{sc2}$ can be about 30 μm to about 50 μm and the width $W_{sc2}$ can be about 10 μm to about 50 μm. In one particular embodiment, the height $H_{sc2}$ can be about 40 μm and the width $W_{sc2}$ can be about 40 μm. In yet another particular embodiment, the height $H_{sc2}$ can be about 40 μm and the width $W_{sc2}$ can be about 15 μm. In the illustrated embodiment, for example, the height $H_{sc2}$ is about 40 μm and the width $W_{sc2}$ is about 25 μm.

The second side channel 18 can also comprise a length (i.e., the distance from the first end 52 to the second end 48 of the first side channel 16). The length can vary depending on the application. In the illustrated embodiment of FIG. 6A, for example, the length of the second side channel 18 is about 4 mm.

At the K-junction 24, the first and second side channels 16, 18 can, for example, be connected by chamfering or beveling the second ends 46, 48 of the first and second side channels 16, 18 relative to each other such the second ends 46, 48 open into each other, as shown in the illustrated embodiment. In an alternative embodiment, the first and second channels can, for example, be connected by a radius or curved joint or connecting portion.

Figure 6G:
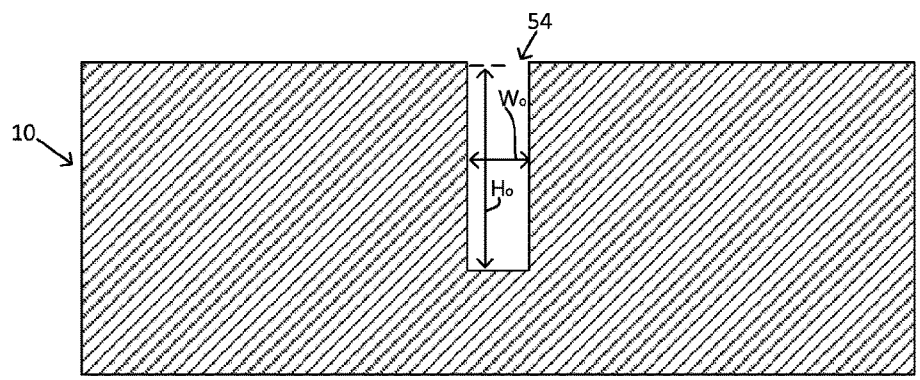

The first and second channels 16, 18 can be connected to the main channel by an opening 54, as best shown in FIG. 6C. The opening 54 can be configured with various dimensions and/or cross-sectional shapes. For example, as best shown in FIG. 6G, the opening 54 has a generally rectangular cross-sectional shape with a height $H_o$ and a width $W_o$. In some embodiments, the height $H_o$ can be about 10 μm to about 200 μm and the width $W_o$ can be about 10 μm to about 200 μm. In preferred embodiments, the height $H_o$ can be about 30 μm to about 50 μm and the width $W_o$ can be about 5 μm to about 30 μm. In the illustrated embodiment, for example, the height $H_o$ is about 40 μm and the width $W_o$ is about 10 μm.

The second side 16 can be positioned at an angle θ relative to the second side channel 18, and the first and second sides 16, 18 can be positioned at respective angles φ and α relative to the main channel 12. In some embodiments, (e.g., the illustrated embodiment) the angles φ and α can be substantially equal. Or in other words, the first channel 16 and the second channel 18 can be substantially symmetrical relative to the main channel 12. In alternative embodiments, the angles φ and α can be different such that the first channel 16 and the second channel 18 are asymmetrical relative to the main channel 12.

In some embodiments, the angle θ can be from about 60 degrees to about 135 degrees. In preferred embodiments, the angle θ can be from about 75 degrees to about 115 degrees. In the illustrated embodiment, for example, the angle θ is about 90 degrees. In some embodiments, the angle φ can be about 20 degrees to about 60. In the illustrated embodiment, for example, the angle φ is about 45 degrees. In some embodiments, the angle α can be about 20 degrees to about 60 degrees. In the illustrated embodiment, for example, the angle α is about 45 degrees.

The electrical field generator 20 can include at least one source channel portion 56 (one in the illustrated embodiment) and at least one ground channel portion 58 (two in the illustrated embodiment), as best shown in FIG. 6A. The source channel 56 can be connected to a sixth port 60 at a first end 62 of the source channel 56, and the source channel 56 can comprise an electrode 64 portion (FIG. 6C) at a second end 66 of the source channel 56. The ground channels 58 can each be connected to a seventh port 68 at first ends 70 of the ground channels 58, and the ground channels 58 can each comprise a respective electrode 72 portion (FIG. 6C) at second ends 74 of the ground channels 58, as best shown in FIG. 6A.

The source channel 56 and ground channel 58 can be configured with various dimensions and/or cross-sectional shapes. For example, the source channel 56 and ground channels 58 can have a generally rectangular cross-sectional shape with a height and a width, and the height of the source channel 56 is about 40 μm, and the width of the source channel 56 is about 100 μm.

The electrode portion 72 of each ground channel 58 can be spaced apart relative to each other, spanning the opening 54, and the tips 78 of the electrodes 72 can be directed substantially towards each other, as best shown in FIG. 6C. The electrode 64 of the source channel 56 can be spaced apart from and disposed between the tips 78 of the electrodes 72 of the ground channels 58. The electrode 64 of the source channel 56 can be spaced apart from and disposed near or adjacent to the K-junction 24. When configured in this manner, the electrical field generator 20 can, for example, be used to generate an electrical field at the K-junction 24 when the electrical field generator 20 is connected to a power supply, as further described below.

The ports (e.g., ports 26, 28, 36, 42, 50, 60, 68) can, for example, be connected to the respective channels (e.g., channels 12, 14, 16, 18, 56, 58) by at least one opening in the ports. For example, the first port 26 has an opening 80 which connects the first port 26 to the first end 30 of the main channel 12, as best shown in FIG. 6B. The ports can include various shapes and sizes. The ports can, for example, be generally cylindrical in shape.

The microfluidic device 10 can be formed using photolithography, as will be appreciated by one of ordinary skill in the art. For example, SU8-2025 photoresist can be spin coated onto silicon wafers to create a master mold. Photolithography can then be conducted by placing a photomask with the desired dimensions of the microfluidic device 10 over the photoresist and exposing the mold to an ultraviolet source, followed by development with PGMEA. The master can be surface treated for 4 to 24 hours with (tridecafluoro-1,1,2,2-tetrahydrooctyl) trichlorosilane under vacuum to increase channel hydrophobicity. The PDMS device can be assembled by mixing RTV615A and RTV615B and degassing under vacuum. After curing (e.g., at 65° C. for 1 hour), the PDMS device can be cut out and inlet holes can be perforated with needles. The PDMS device and a glass slide can be cleaned and plasma treated to irreversibly bond the PDMS device to glass, thus forming the microfluidic device 10. The microfluidic device 10 can be pre-treated with 1% by volume (tridecafluoro-1,1,2,2-tetrahydrooctyl)trichlorosilane in Fluoroinert FC-40 carrier fluid to increase channel hydrophobicity.

When the microfluidic device is configured in this manner, the main channel 12, and channels 14, 16, 18 can all be in fluidic communication with each other. For example, a fluid can flow from the first port 26 into and through the main channel 12 and out of the second port 28, or vice versa.

Fluid can be injected and/or extracted from any of the ports and/or that fluid can flow in any direction within the channels. It should also be noted that multiple fluid types (e.g., aqueous and/or oil) can flow within the various channels and that multiple fluid types can flow within each channel simultaneously and/or sequentially.

Further, when configured in this manner, the K-junction 24 of the microfluidic device 10 can, for example, be used to generate and/or manipulate droplets. In some particular embodiments, the K-junction 24 can be used for example to inject volume into the droplets, extract volume from the droplets, generate or form droplets, and/or split the droplets.

For example, FIGS. 7A-12D show the microfluidic device 10 being used for multiple fluidic manipulations. Although not shown, to perform the fluidic manipulations, the microfluidic device 10 can, for example, be configured with various fluid supply devices and control mechanisms. For example, fluids can be delivered into the micro fluidic device using tubing (e.g., 30 AWG PTFE) which can be injected into the ports from a vial pressurized with compressed gas (e.g., $N_2$). Pressure delivery to the vials can, for example, be controlled by solenoid valves. The solenoid valves can be actuated by a multifunction data acquisition device controlled by software (e.g., LabView). One or more pumps can be controllable to vary the rate of flow of fluid in the channels. Suitable pumps can include, for example, syringe pumps.

In each of the examples shown in FIGS. 7A-11D, the microfluidic device 10 is configured such that the main channel 12 and the channels 14, 16 each have a height of about 40 μm and width of about 40 μm. The second side channel 18 has a height of about 40 μm and width of about 25 μm. The opening 54 from the first and second channels 16, 18 into the main channel 12 has a height of about 40 μm and width of about 10 μm. The K-junction 24 is configured such that the angle θ is about 90 degrees, and the angles ϕ and α are each about 45 degrees.

The electric field generator 20 can be configured such an electric field can be generated at the K-junction 24 by providing an electrolytic solution 128 (e.g., 0.5 M NaCl) connected to AC power supply in the source channel 56 and to a ground in the ground channel 58. The electric field is not present in FIGS. 9A-11D. Various other parameters are further described below.

Figure 7A:
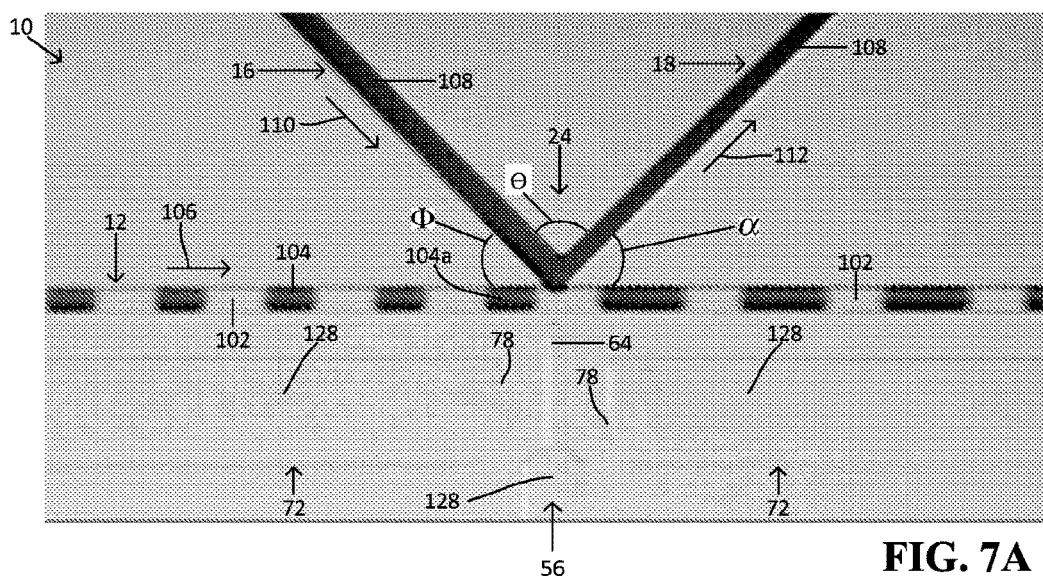
FIGS. 7A-11D show the microfluidic device performing various exemplary functions.
Figure 7B:
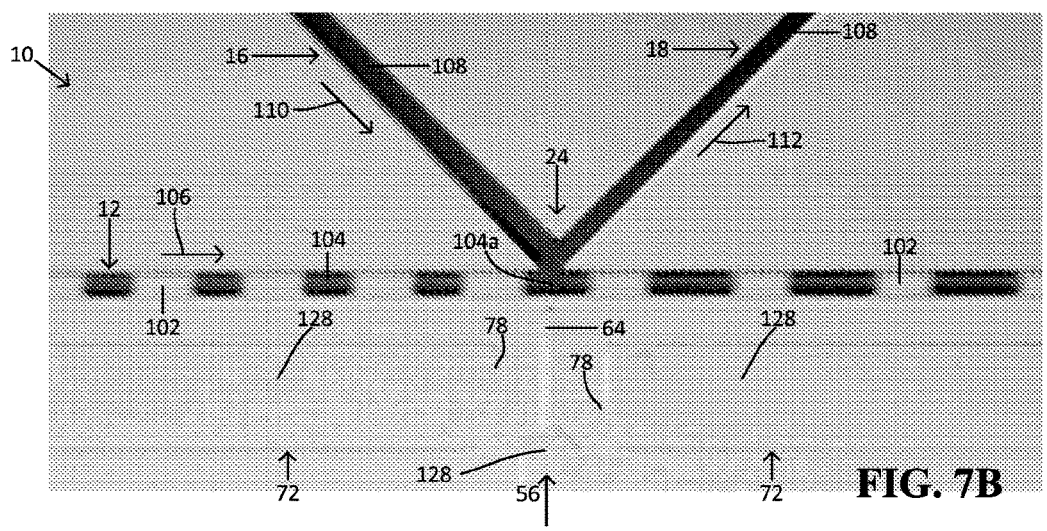
Figure 7C:
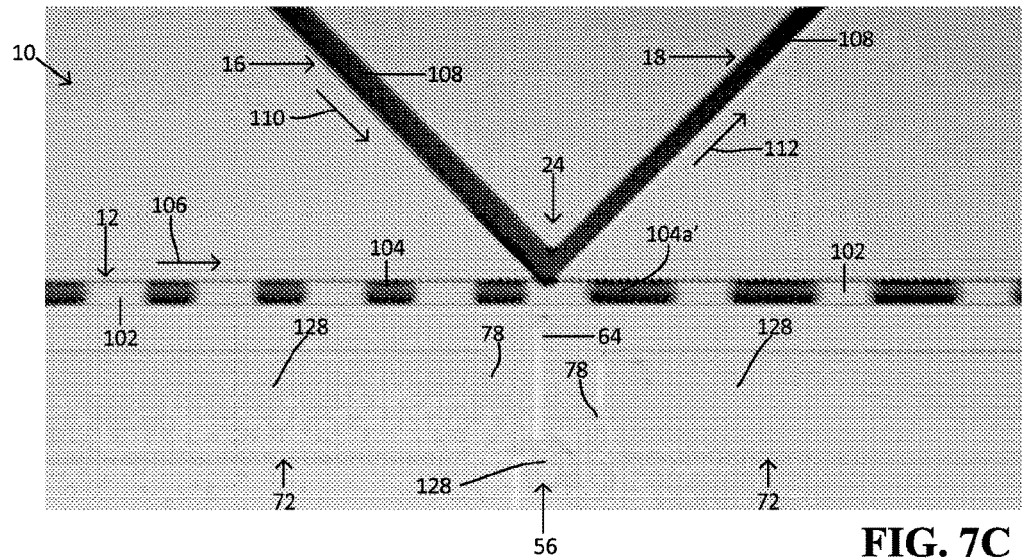

FIGS. 7A-7C show the microfluidic device 10 using a first aqueous fluid 100 and an oil 102 (e.g., 3M® Novec® 7500 Engineered Fluid with 2% by weight poly(ethylene glycol) di-(krytox-FSH amide) added as a surfactant to stabilize droplets) to generate a plurality of aqueous droplets 104. Although not shown, the aqueous droplets 104 can, for example, be formed by injecting the oil 102 into the first port 26 and flowing the oil 102 through the main channel 12 at a pressure of 65 kPa towards the second port 28 (i.e., in the direction shown by arrow 106 (FIG. 7A)) and by injecting the first aqueous fluid 100 into the third port 36 and flowing the first aqueous fluid 100 through the droplet formation channel 14 towards the T-junction 22 at a pressure of 60 kPa. At the T-junction 22, the microfluidic device 10 forms the aqueous droplets 104 separated by the oil 102. Due to the pressure in the main channel 12, the formed aqueous droplets flow from the T-junction toward the K-junction 24.

As shown, the K-junction 24 can, for example, be configured such that a second aqueous fluid 108 flows into the fourth port 42, through the first side channel 16 (i.e., in the direction shown by arrow 110) toward the K-junction 24, and through the third side channel 18 towards the fifth port 50 (i.e., in the direction shown by arrow 112) at a pressure of 45 kPa. Generally speaking, the second aqueous fluid 108 is flowing generally parallel to the flow of the main channel 12.

When configured in this manner, the K-junction 24 can inject or add volume to the droplets 104 as the droplets 104 pass by the K-junction 24. For example, FIG. 7A shows a particular droplet 104*a* approaching the K-junction 24. FIG. 7B shows the droplet 104*a* at the K-junction. At this point, the droplet 104*a* increases its volume by receiving a portion of the second aqueous fluid 108 through the opening 54. Thus, the droplet 104*a* becomes droplet 104*a'*, 104*a'* being the droplet 104*a* formed from the first aqueous fluid 100 plus the additional volume of second aqueous fluid 108, as best shown in FIG. 7C.

Figure 12A:
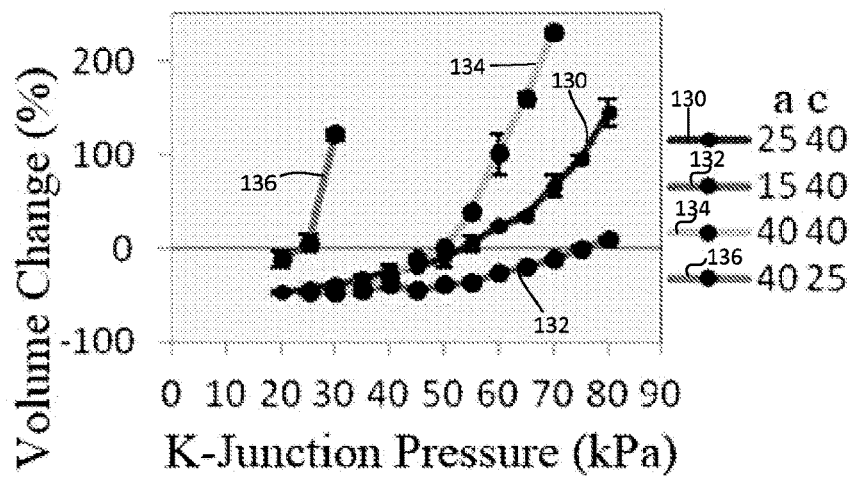
FIGS. 12A-14B are graphs providing data about various embodiments of a microfluidic device.
Figure 12B:
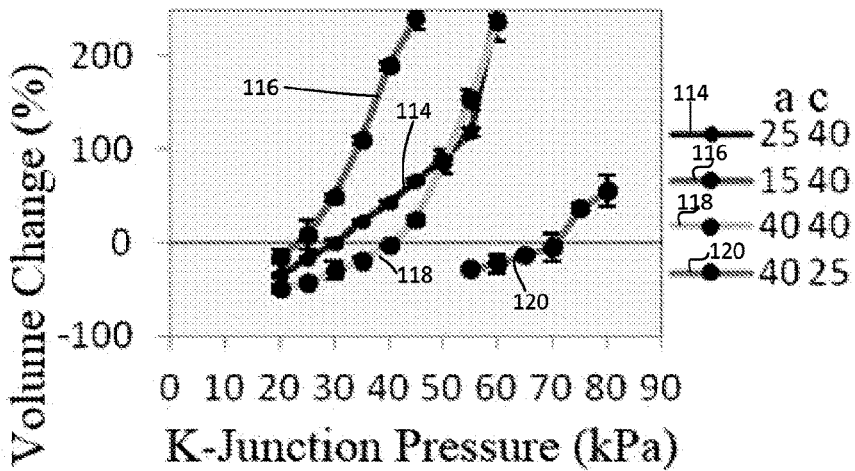

The change in volume from the initially formed droplet (e.g., droplet 104*a*) to the droplet altered by the second aqueous fluid 108 at the K-junction 24 (e.g., droplet 104*a'*) can be adjusted by altering the pressure in the main channel 12 and opening 54 at the K-junction 24. The change in volume can also be adjusted by altering the dimensions (e.g., the widths) of the first and second side channels 16, 18. For example, FIG. 12B shows various percent changes in volume of the droplet for a variety of K-junction pressures and a variety of widths of the first and second side channels 16, 18. In FIG. 12B, "a" indicates the width (in μm) of the second side channel 18 and "c" indicates the width (in μm) of the first side channel 16. For example, the plot line 114 represents the embodiment shown in FIGS. 7A-7C. Other plots lines 116, 118, 120 show, for example, other configuration and the versatility and tunability of a single K-junction geometry. This can, for example, advantageously allow a user of the microfluidic device 10 to desirably select the pressures and/or dimensions for the desired output. To summarize, the overall trend of this configuration is an increase in volume for a wide range of pressure changes and widths.

Figure 8A:
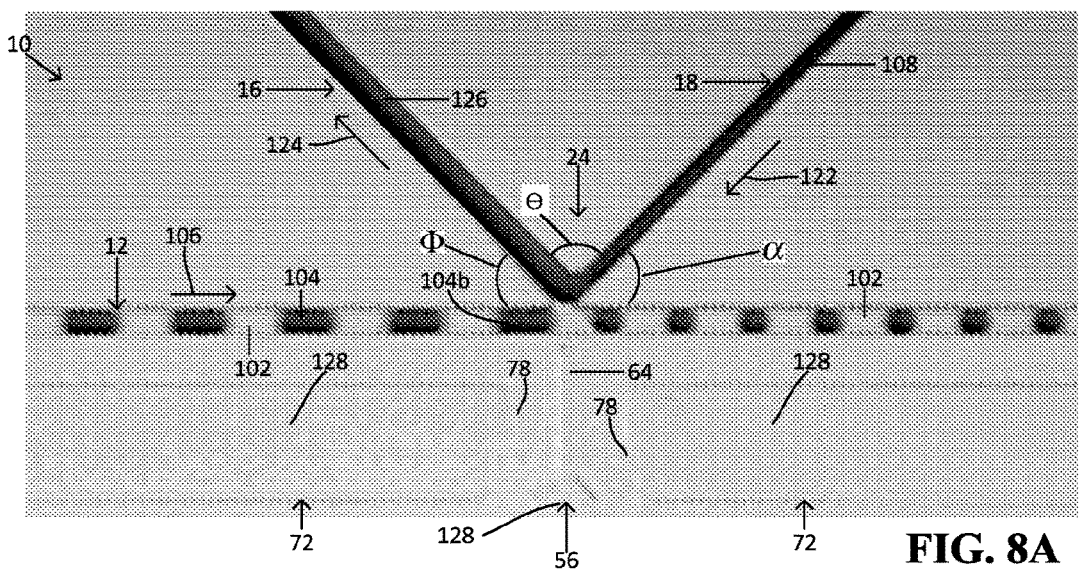
Figure 8B:
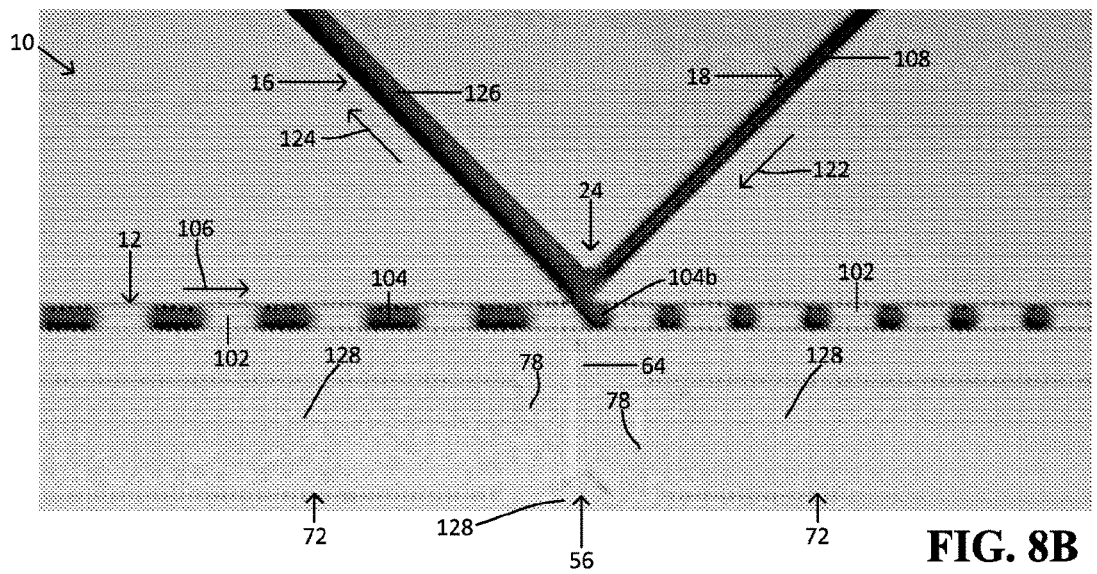
Figure 8C:
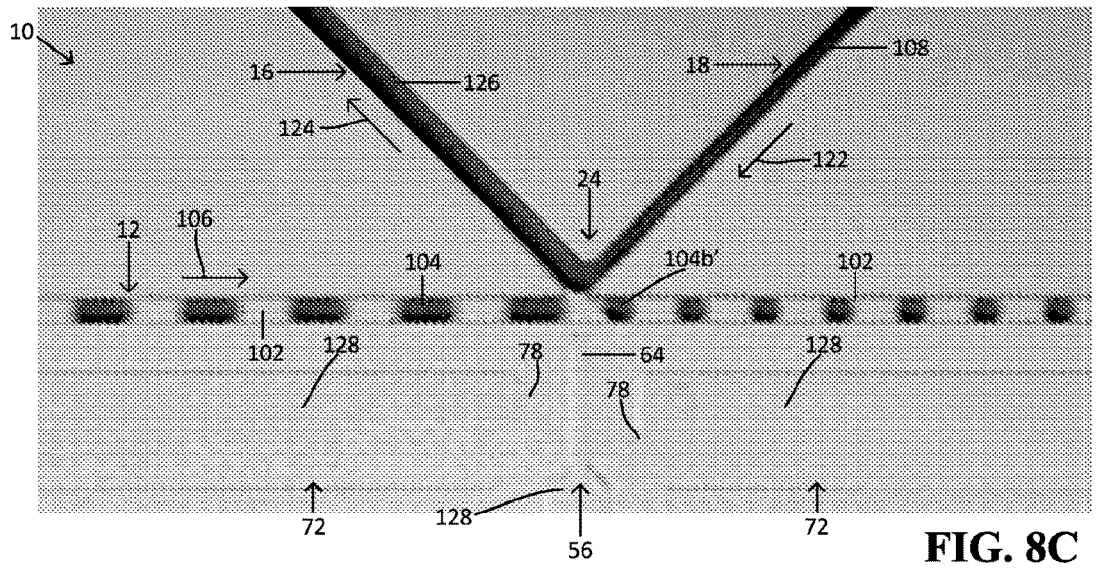

Also, the K-junction can, for example, be used to extract volume from the droplets 104, as shown in FIGS. 8A-8C. In this embodiment, the parameters are the same as in FIGS. 7A-7C except that the second aqueous fluid 108 is flowing in the opposite direction, i.e., the second aqueous fluid 108 is flowing from the fifth port 50, through the second side channel 18 towards the K-junction 24 (i.e., in the direction shown by arrow 122), through the first side channel 16 away from the K-junction 24 (i.e., in the direction shown by arrow 124), towards the fourth port 42. Generally speaking, the second aqueous fluid 108 is flowing generally anti-parallel to the flow of the main channel 12. Also, the pressure at the opening 54 has been changed to 20 kPa.

When configured in this manner, the K-junction 24 can extract or remove volume from the droplets 104 as the droplets 104 pass by the K-junction 24. For example, FIG. 3A shows a particular droplet 104b approaching the K-junction 24. FIG. 3B shows the droplet 104b at the K-junction. At this point, the volume of the droplet 104b decreases as a portion of first aqueous fluid 100 is drawn or pulled through the opening 54 into the first side channel 16. Thus, the droplet 104a becomes droplet 104b', 104b' being the droplet 104a formed from the first aqueous fluid 100 minus the volume extracted at the K-junction 24, as best shown in FIG. 3C. In addition the second fluid 108 flowing through the first side channel is also altered by the addition of the volume of the first fluid 100 that is extracted from the droplets 104. As such, the second fluid 108 becomes third aqueous fluid 126.

The change in volume from the initially formed droplet (e.g., droplet 104b) to the droplet reduced at the K-junction 24 (e.g., droplet 104b') can be adjusted by altering the pressure in the main channel 12 and opening 54 at the K-junction 24. The change in volume can also be adjusted by altering the dimensions (e.g., the widths) of the first and second side channels 16, 18. For example, FIG. 12A shows various percent changes in volume of the droplet for a variety of K-junction pressures and a variety of widths of the first and second side channels 16, 18. In FIG. 12A, "a" indicates the width (in µm) of the second side channel 18 and "c" indicates the width (in µm) of the first side channel 16. For example, the plot line 130 represents the embodiment shown in FIGS. 8A-8C. Other plots lines 132, 134, 136 show, for example, other configurations. To summarize, the overall trend of this configuration is a reduction of volume for a wide range of pressure changes and widths.

In the illustrated embodiments (e.g., FIGS. 7A-7C), the first aqueous fluid 100 and the second aqueous fluid 108 are the same fluid. In these embodiments, the when the first aqueous fluid 100 and the second aqueous fluid 108 are mixed to form a third aqueous fluid 128, the third fluid will also be the same. In alternative embodiments, the first and the second aqueous fluids 100, 108 can, for example, be different fluids.

Figure 9A:
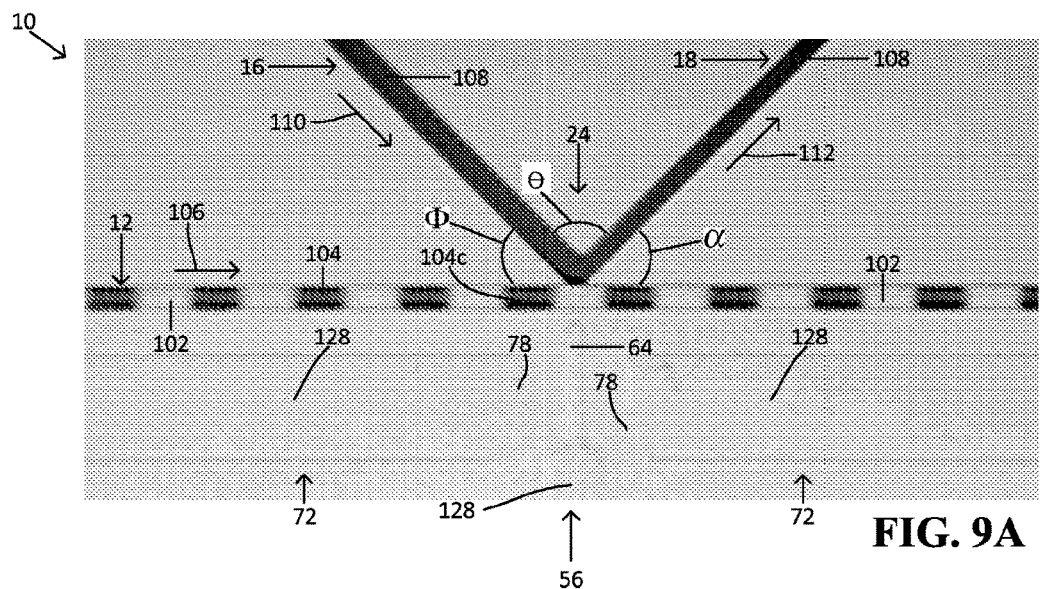
Figure 9B:
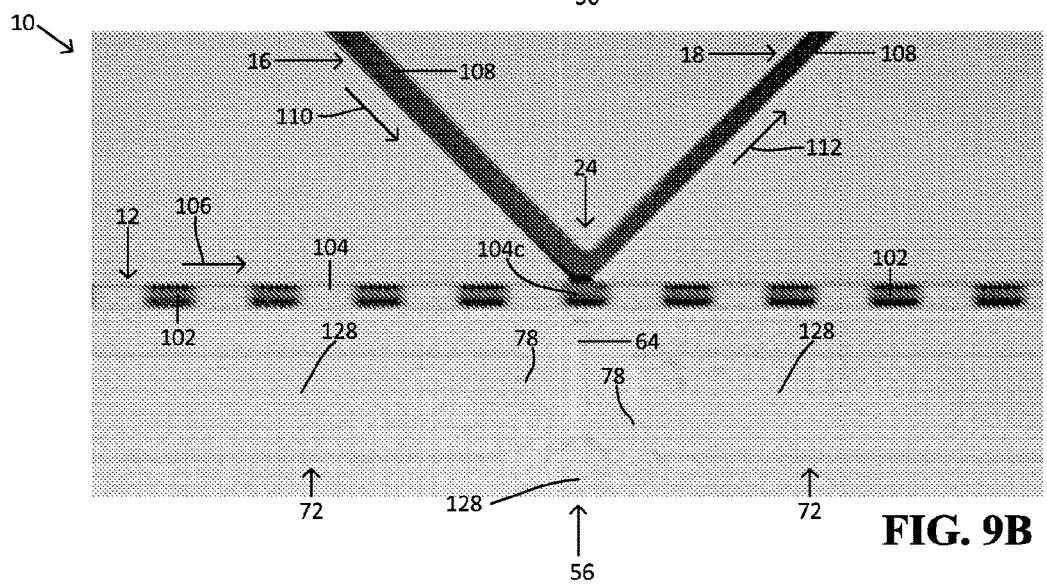
Figure 9C:
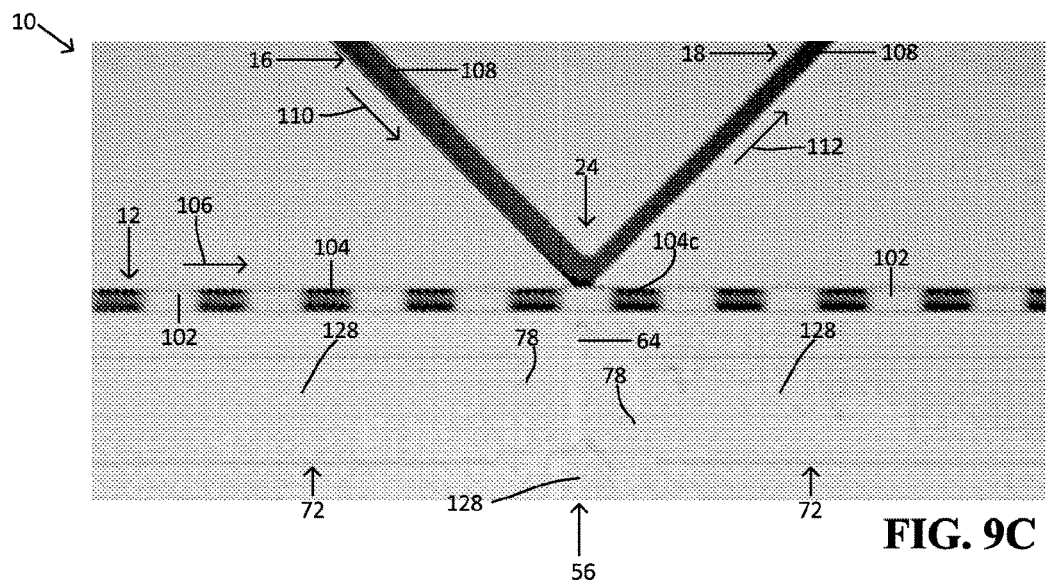

In addition, the K-junction 24 can, for example, be used to balance the aqueous solution 108 with passing droplets 104 using parallel flow in the absence of an electric field, as shown in FIGS. 9A-9C. In this embodiment, the parameters are the same as in FIGS. 7A-7C, except that the pressure at the opening 54 has been changed to 27 kPa and the electrical field has been removed by turning off the power supply which is connected to the source and ground channels 56, 58. When configured in this manner, the droplets 104 are unaltered as they pass by the K-junction. For example, FIGS. 9A-9C show a particular droplet 104c passing by the K-junction.

Further, the K-junction 24 can, for example, be used to form or generate droplets 104 using anti-parallel aqueous fluid 100 flow in the first and second side channels 16, 18 (i.e., flow in the directions shown by arrows 122, 124, respectively). In this particular example, there is an absence of an electric field. As shown, the pressure of the first aqueous solution 100 at the opening 54 is about 40 kPA. Oil can, for example, flow through the main channel at 60 kPa in the direction shown by arrow 106.

Figure 10A:
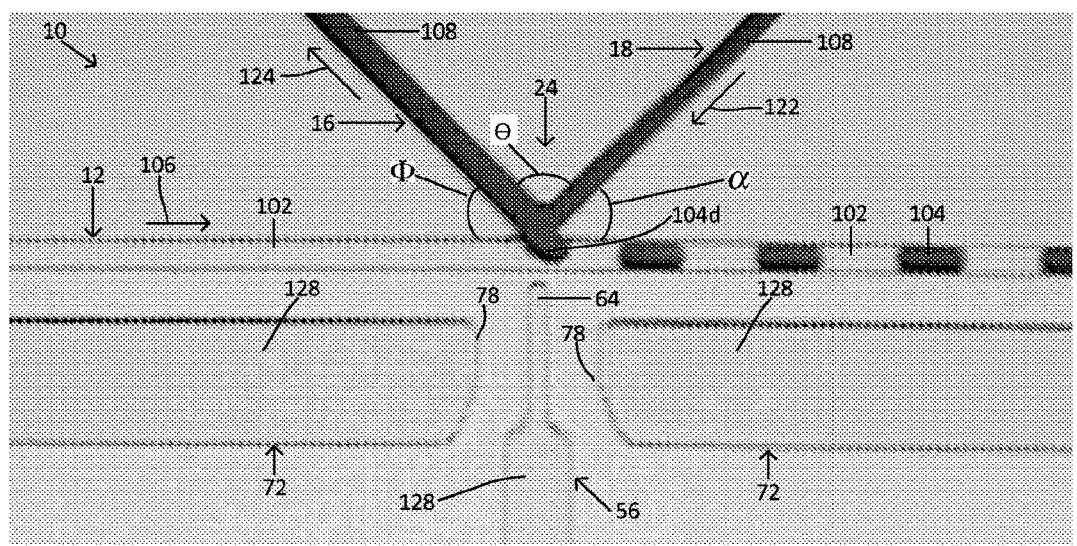
Figure 10B:
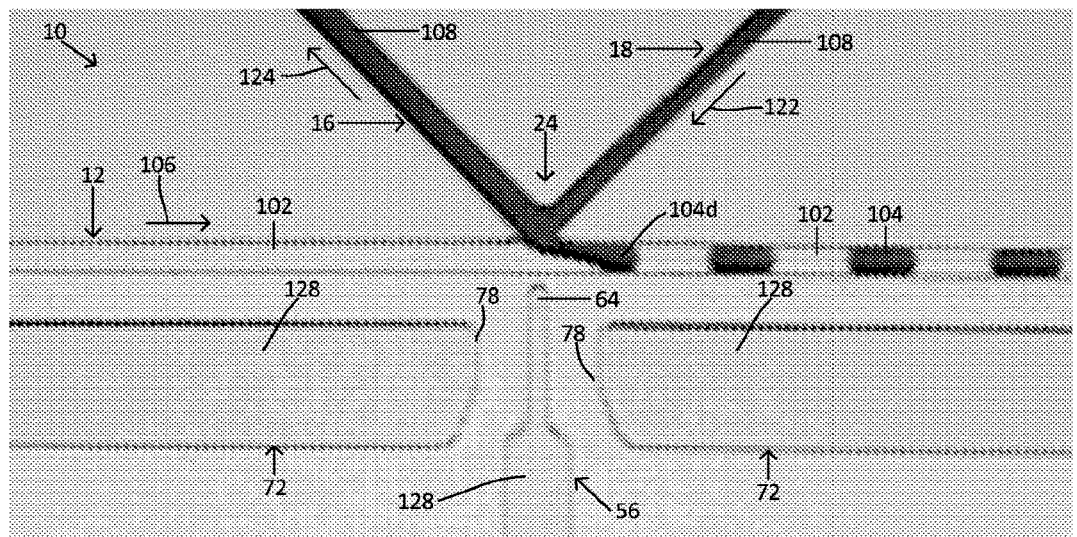
Figure 10C:
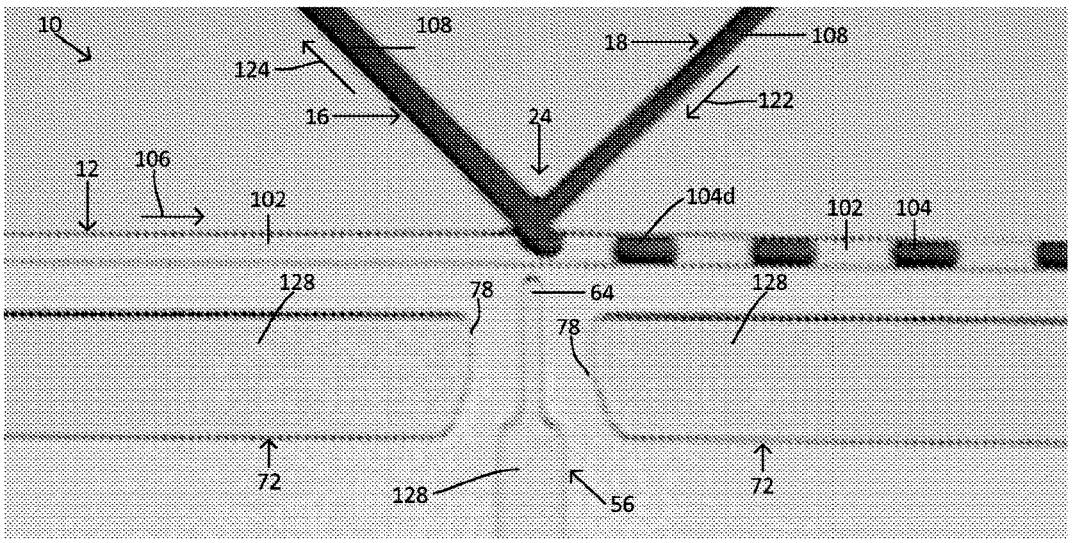

For example, FIG. 10A shows a particular droplet 104d forming at the opening 54 and entering into the main channel 12. FIG. 10B shows the droplet 104d separating from the first aqueous solution 100 and entering the oil 102. FIG. 10C shows the fully formed droplet 104d in the main channel 12.

When forming droplets using a K-junction, as described above, a microfluidic device can be configured without a droplet formation channel (e.g., droplet formation channel 14). For example, FIG. 19 shows an exemplary embodiment of a microfluidic device 400 which can, for example, be used to generate droplets. In the illustrated embodiment, the microfluidic device 400 is configured in a manner similar to the microfluidic device 10 and includes a main channel 402, a first side channel 404, a second side channel 406, and an electric field generator 408. As shown, the microfluidic device 400 does not have a separate droplet formation channel (e.g., droplet formation channel 14) because the microfluidic device 400 can, for example, use a K-junction 410 (i.e., the junction formed at the intersection of the main channel 402 and the first and second side channels 404, 406) to form the droplets in a manner similar to the K-junction 24 of microfluidic device 10 (e.g., as shown in FIGS. 10A-10C).

In yet another configuration, the K-junction 24 can for example be used to split or divide droplets 104 using anti-parallel flow in the absence of an electric field, as shown in FIGS. 11A-11D. The parameters in this configuration are substantially similar to the configuration of FIGS. 8A-8C except that oil 102 rather than aqueous fluid 100 is flowing in an anti-parallel direction through the first and second side channels 16, 18, relative to the main channel 12. The pressure of the oil 102 at the opening 54 is 20 kPa.

Figure 11A:
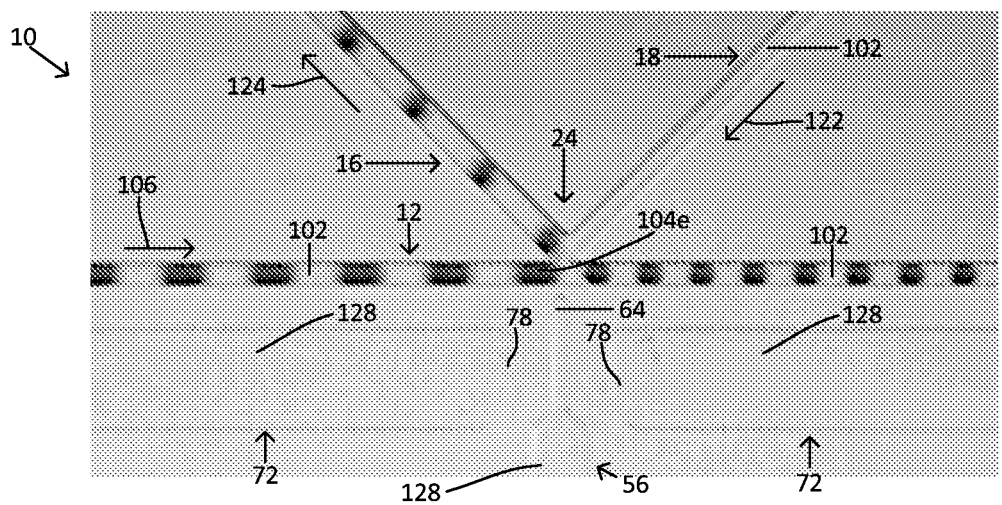
Figure 11B:
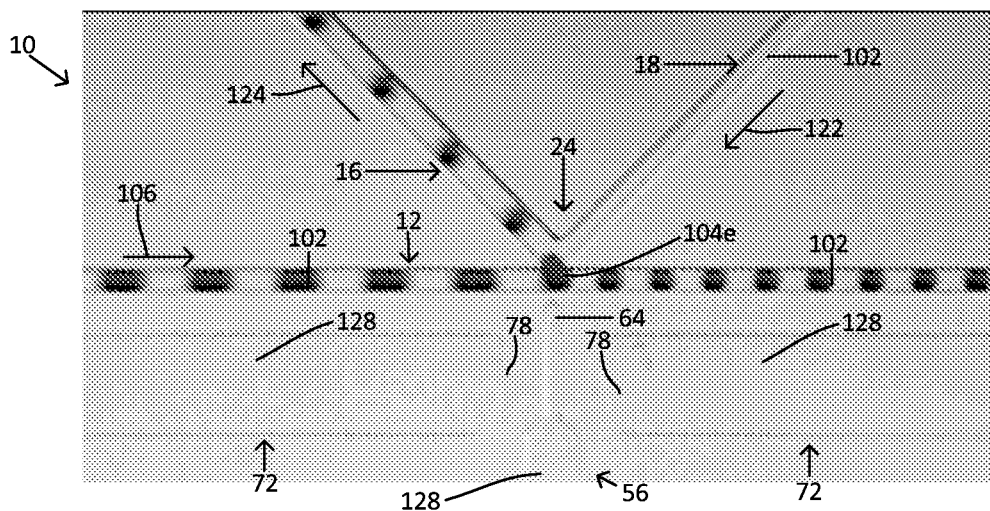
Figure 11C:
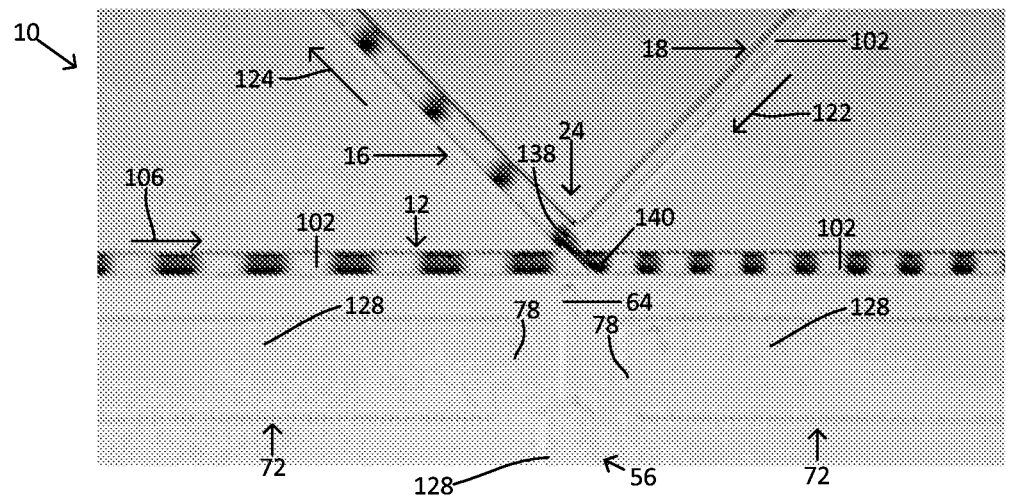
Figure 11D:
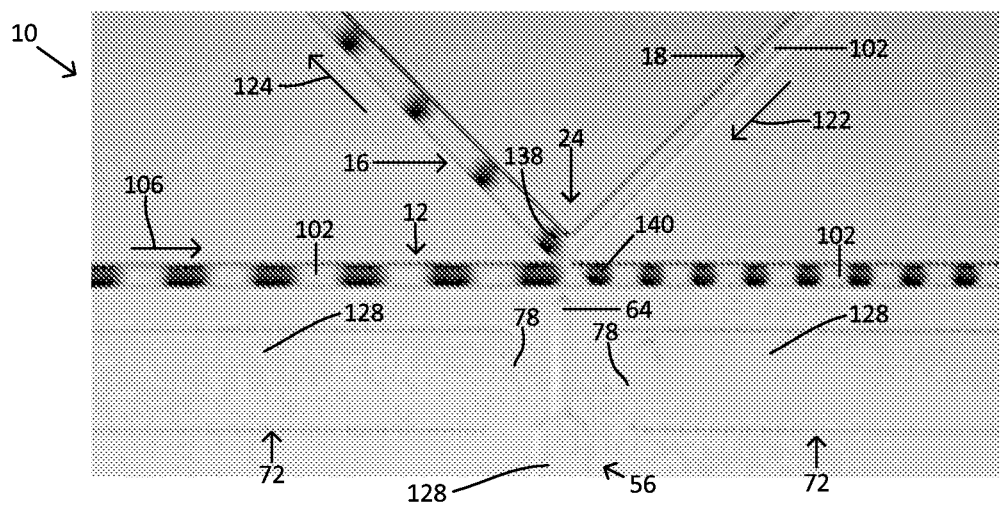

When configured in this manner, the droplets 104 can be formed using the T-junction 22, as described above. As the droplets 104 pass the K-junction 24, the each droplet 104 can be split or divided and a first portion of the each droplet can flow into the first side channel and a second portion can continue to flow through the main channel, as shown in FIG. 6A-6D. For example, FIG. 11A shows a particular droplet 104e approaching the K-junction 24. FIG. 11B shows the droplet 104e at the K-junction as the droplet 104e begins to split. FIG. 11C shows a first portion 138 of the droplet 104e separating from the second portion 140 of the droplet 104e. FIG. 11D shows the first portion 138 of the droplet 104e flowing through the first side channel 16 and the second portion 140 of the droplet 104e flowing through the main channel 12.

Figure 12C:
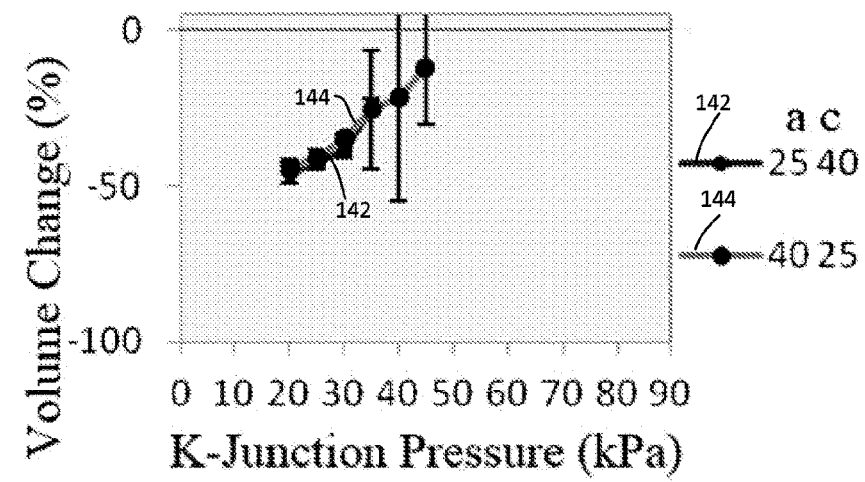

The change in volume from the initially formed droplet (e.g., droplet 104e) relative to the second portion of the droplet (e.g., portion 140 of droplet 104e) can be adjusted by altering the pressure in the main channel 12 and opening 54 at the K-junction 24. The change in volume can also be adjusted by altering the dimensions (e.g., the widths) of the first and second side channels 16, 18. For example, FIG. 12C shows various percent changes in volume of the droplet for a variety of K-junction pressures and a variety of widths of the first and second side channels 16, 18. In FIG. 12C, "a" indicates the width (in µm) of the second side channel 18 and "c" indicates the width (in µm) of the first side channel 16. For example, the plot line 142 represents the embodiment shown in FIGS. 11A-11D (i.e., anti-parallel flow in the side channels 16, 18 relative to the main channel 12). Another plot line 144 shows, for example, another configuration. In the configuration of plot line 144, the flow in the side channels 16, 18 is parallel to the main channel 12 (i.e., opposite of direction of flow in FIGS. 11A-11D), and the widths of the side channels 16, 18 have been switched relative configuration shown in FIG. 11A-11D. As shown in FIG. 12C, the plot lines 142, 144 are substantially similar.

Figure 13A:
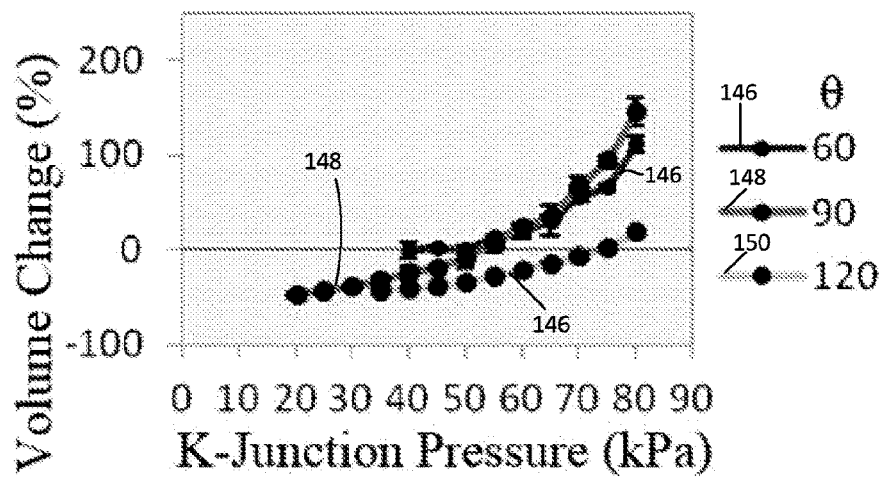
Figure 13B:
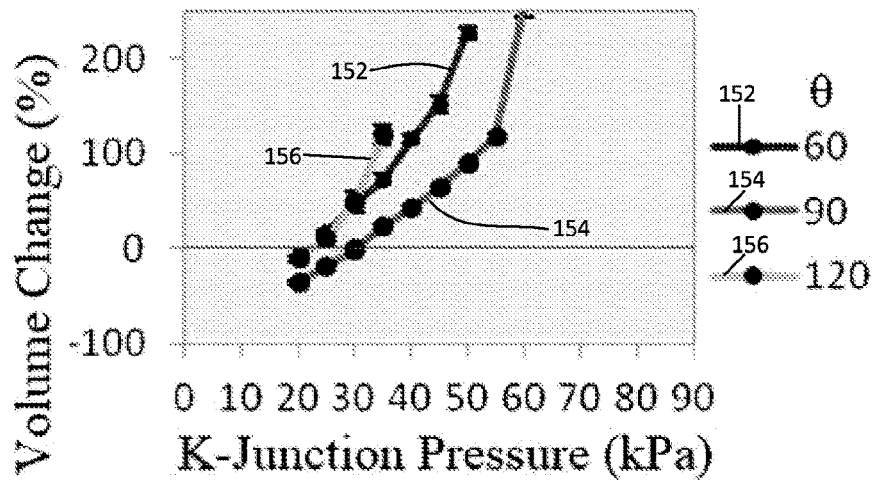
Figure 13C:
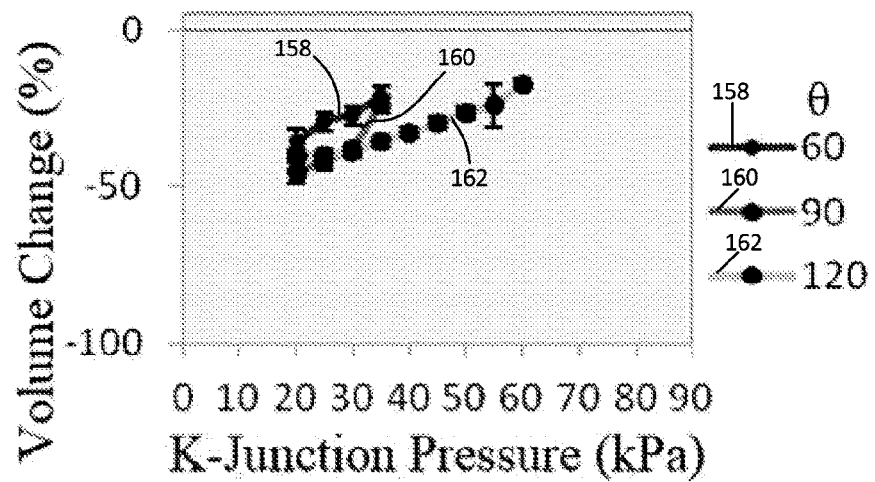

Thus, as shown, the microfluidic device 10 can provide a wide range of functionality in one configuration. This improved functionality and versatility can, for example, allow a single device to perform multiple functions or manipulation on droplets and/or other fluids. For example, first, a droplet can be formed using the device by flowing the fluid in a first direction The angles θ, φ, α can, for example, also be altered to manipulate the functionality of the microfluidic device 10. For example, FIGS. 13A-13C show various volume changes by of the angle θ from 60 degrees to 120 degrees. For FIGS. 13A-13C, the channel dimensions are fixed. Each of the channels has a height of 40 and the main channel 12, the first channel 16, and second channel 18 have widths of 40 µm, 40 µm, and 25 µm. The opening 54 has height of 40 µm and a width of 10 µm. The K-junction 24 is substantially symmetrical such that as the angle θ is altered, the angles φ and α are equally altered. For example, φ and α each=(90°−θ/2).

In FIG. 13A, the flow of the droplets in the main channel 12 was in the direction shown by arrow 106 and the flow of the aqueous fluid 100 of the side channels 16, 18 is in the anti-parallel direction shown by the respective arrows 124, 122, similar to the configuration shown in FIG. 8A-8C. The plot lines 146, 148, 150 show that the general trend for this configuration is a bias toward withdrawing or extracting fluid.

In FIG. 13B, the flow of the droplets in the main channel 12 was in the direction shown by arrow 106 and the flow of the aqueous fluid 100 in the side channels 16, 18 is in the parallel direction shown by the respective arrows 110, 112, similar to the configuration shown in FIG. 7A-7C. The plot lines 152, 154, 156 show that the general trend for this configuration is a bias toward injecting fluid.

In FIG. 13C, the flow of the droplets in the main channel 12 was in the direction shown by arrow 106 and the flow of the oil fluid 102 of the side channels 16, 18 is in the anti-parallel direction shown by the respective arrows 124, 122, similar to the configuration shown in FIG. 11A-11D. The plot lines 158, 160, 162 show that the general trend for this configuration is a bias toward splitting droplets.

Figure 14A:
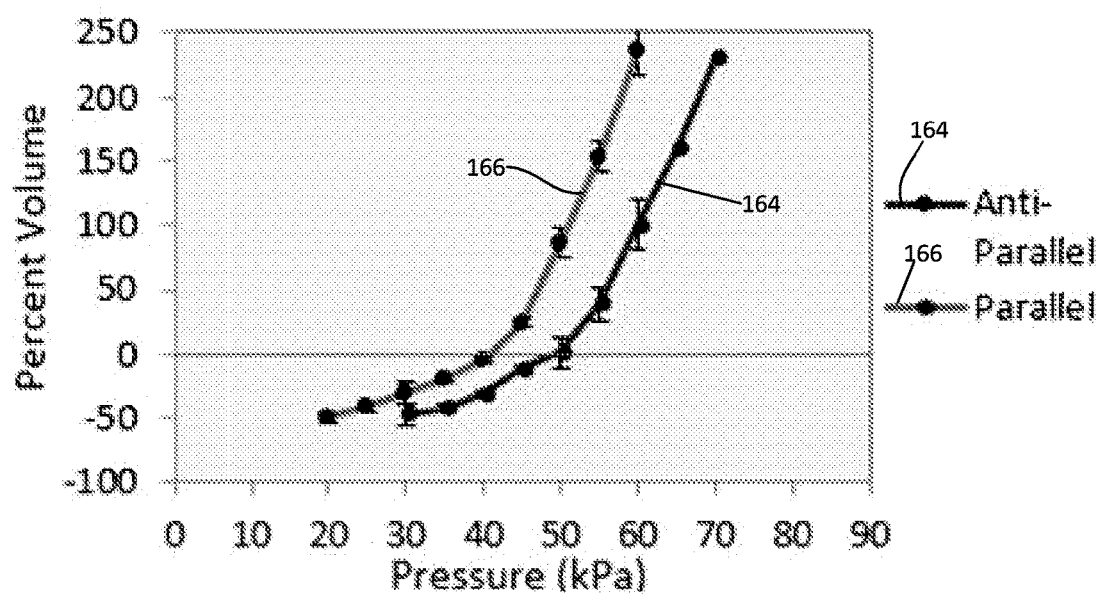

FIG. 14A shows a comparison of parallel (plot line 164) and anti-parallel (plot line 166) aqueous flow behavior for a symmetrical K-junction 24. The configuration shown in FIG. 14A has channel heights of 40 µm; channel widths for the main channel, first side channel, and second side channel being 40 µm, 40 µm, and 40 µm, respectively; opening 54 is 10 µm; θ is 90, φ is 45 degrees, α is 45 degrees; oil flow at 65 kPa; and droplet formation at 60 kPa. As shown, changing the flow direction of the side channels 16, 18 can, for example, shift behavior by around 10 kPa due to increased resistance for anti-parallel flow entering the channel because it opposes main channel 12 flow. Injection into droplets and extraction can occur in the presence of an electric field.

Figure 14B:
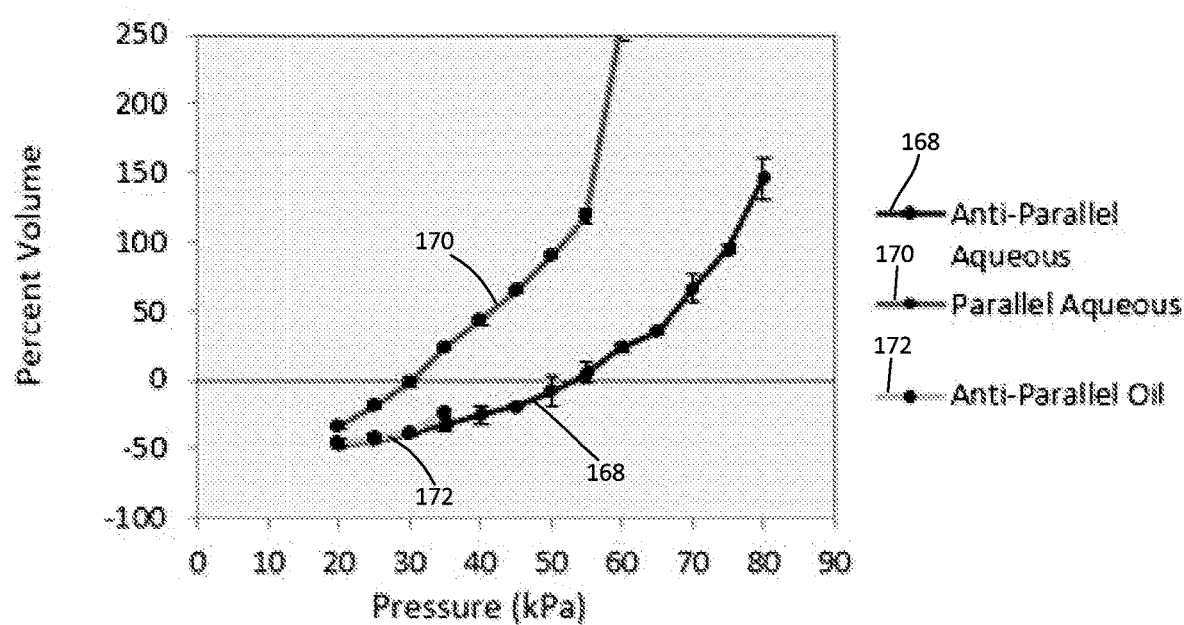

FIG. 14B demonstrates the K-junction's versatility via extraction and injection with parallel (plot line 170) and anti-parallel (plot line 168) aqueous flow behavior and droplet splitting with anti-parallel oil flow (plot line 172). The configuration shown in FIG. 14B is substantially the same as FIGS. 7A-8C (i.e., channel heights of 40 µm; channel widths for the main channel, first side channel, and second side channel being 40 µm, 40 µm, and 25 µm, respectively; opening 54 is 10 µm; θ is 90, φ is 45 degrees, α is 45 degrees; oil flow at 65 kPa; and droplet formation at 60 kPa). As shown, changing aqueous flow direction under experimental conditions provided a significant shift in performance because of increased resistance for anti-parallel flow entering the channel in opposition to main channel flow. Additionally, anti-parallel flow transitioning from a narrower inlet to a wider outlet channel, further biases toward fluid remaining in the K-Junction and biases toward extraction and oil splitting. Injection into droplets and extraction can occur in the presence of an electric field.

Figure 15A:
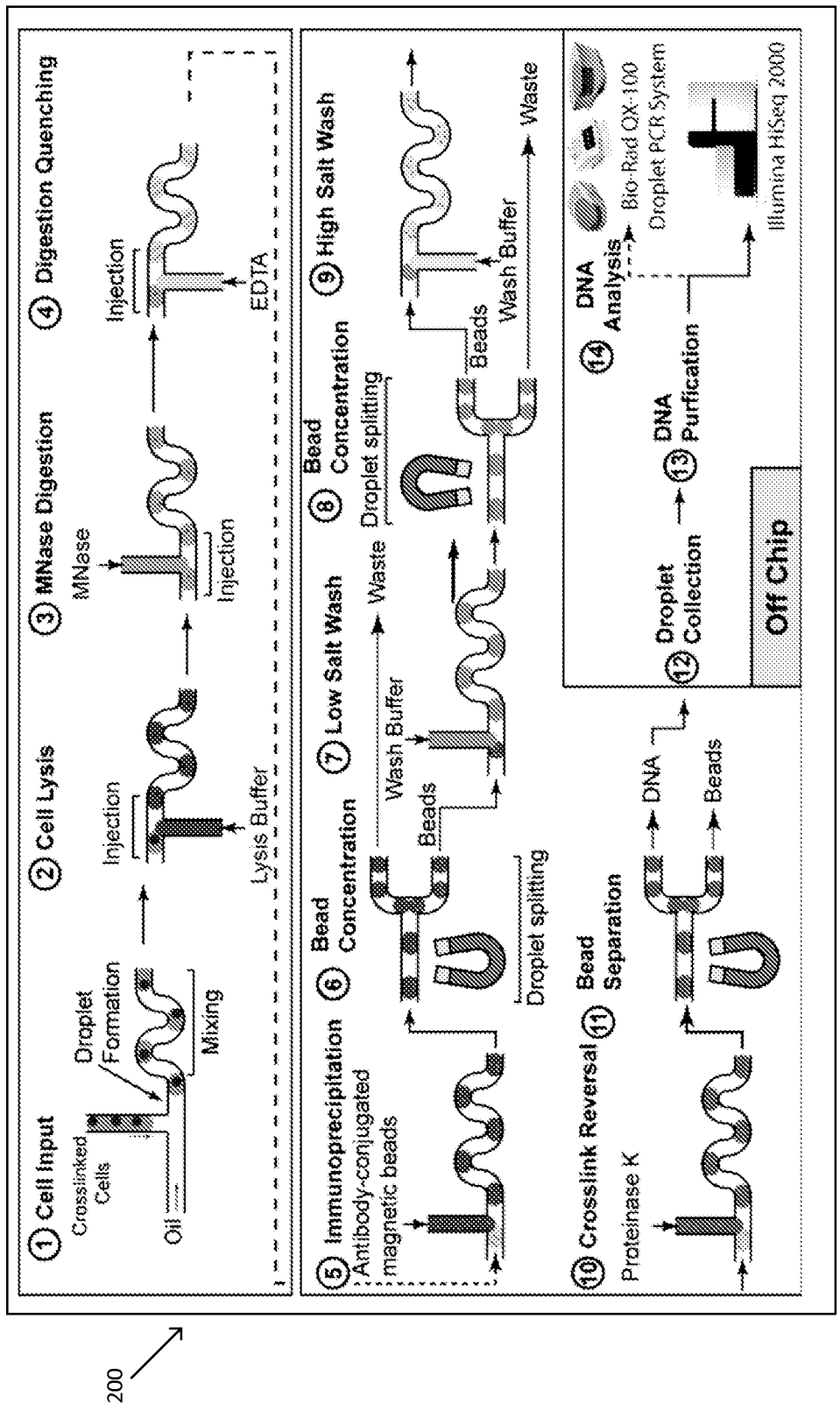
FIGS. 15A-15C show various exemplary systems in which the microfluidic device can be used.
Figure 15B:
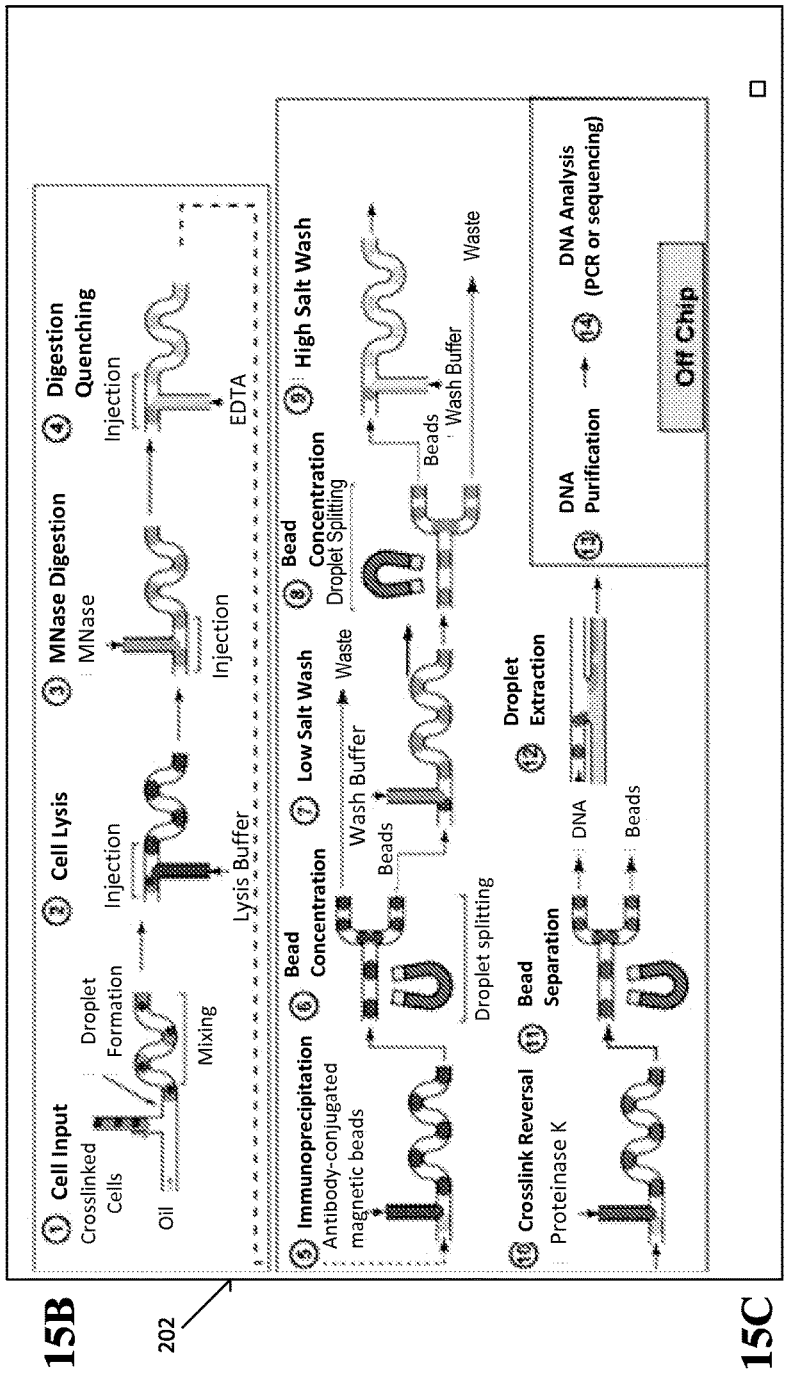
Figure 15C:
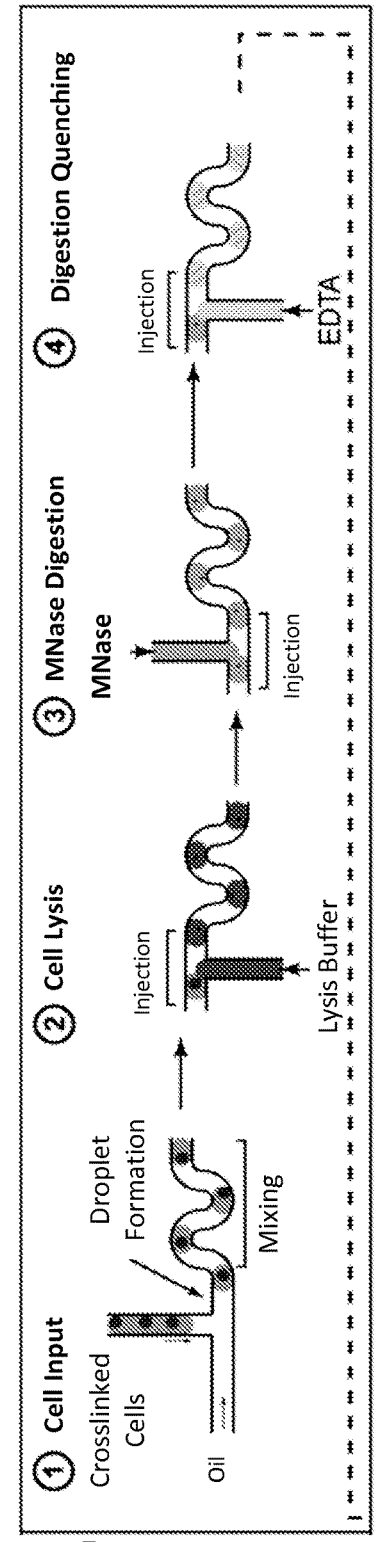

FIGS. 15A-15C shows, for example, a variety of modules or systems 200, 202, 204 that can incorporate the microfluidic device 10. FIG. 15A shows a system 200 for single cell analysis. FIG. 15B shows a system 202 for performing DNA PCR or sequencing. FIG. 15C shows a system 204 for nuclease incubation. In systems 200, 202, 204, the K-junction 24 of the microfluidic device 10 can, for example, be used at the steps (e.g., step 2) where there are T-junctions. A similar modules or system can be based on FIG. 1D.

FIGS. 16A-18C show an example of a microfluidic device 300, according to one embodiment. The device 300 can comprise a main channel portion 302, a droplet formation portion 304, an injector portion 306, a serpentine portion 308, and an extractor portion 310.

The main channel 302 and the droplet formation portion 304 can, for example, be configured to form aqueous droplets 312 (FIGS. 17A-18C), similar to device 10. The injector 306 can, for example, be a K-junction (similar to K-junction 24 of the device 10).

Figure 16A:
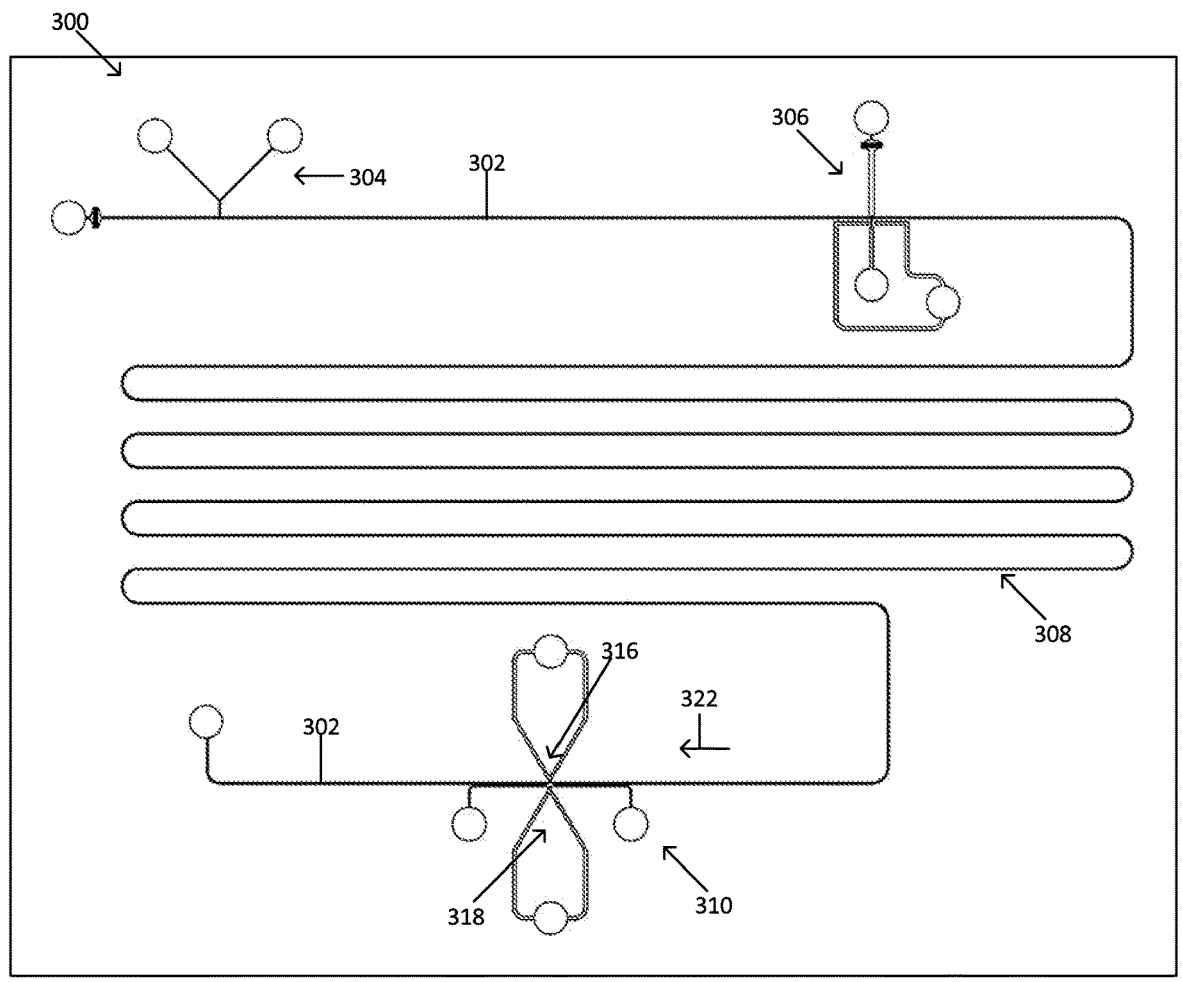
FIG. 16A is a schematic of a microfluidic device, according to another embodiment.
Figure 16B:
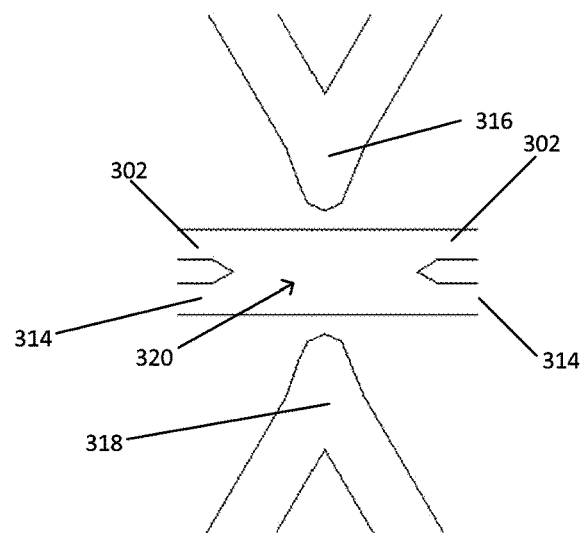
FIG. 16B is a detail view of the microfluidic device of FIG. 16A.

The extractor 310 can, for example, comprise a side channel 314 which is connected to and substantially parallel to the main channel 302 for a portion of the main channel 302 to form a junction 320, as best shown in FIG. 16B. The extractor 310 can also include a source channel 316 and a ground channel 318. The source channel 316 and the ground channel 318 can, for example, be used to create an electric field. The source channel 316 and ground channel 318 can be aligned relative to one another and span across junction 320.

Figure 17A:
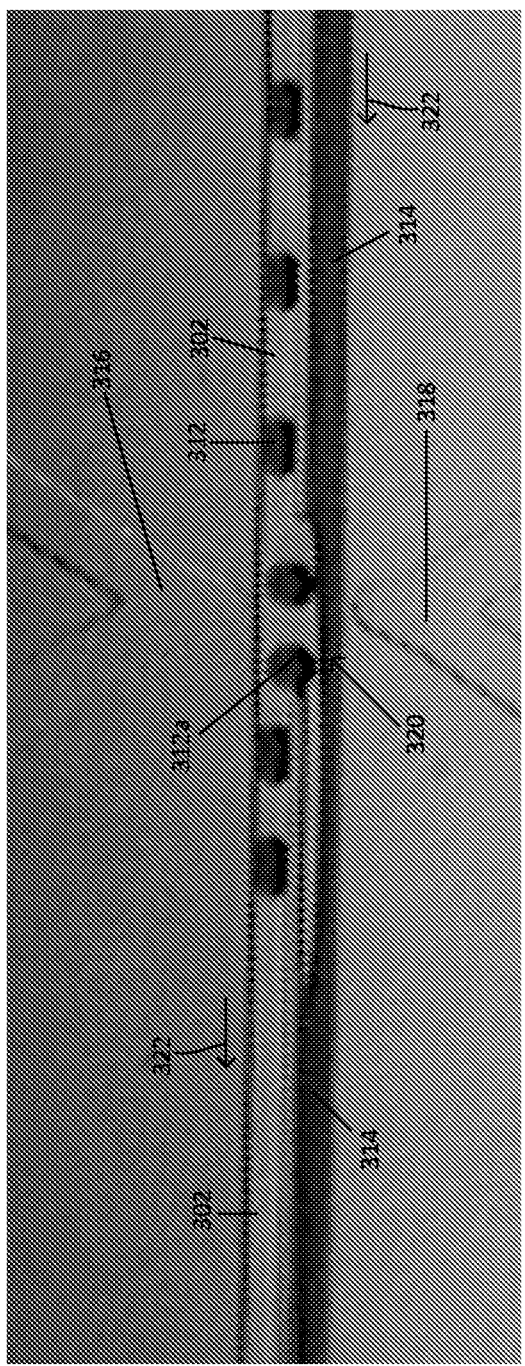
FIGS. 17A-18C show the microfluidic device of FIG. 16A performing various exemplary functions.
Figure 17B:
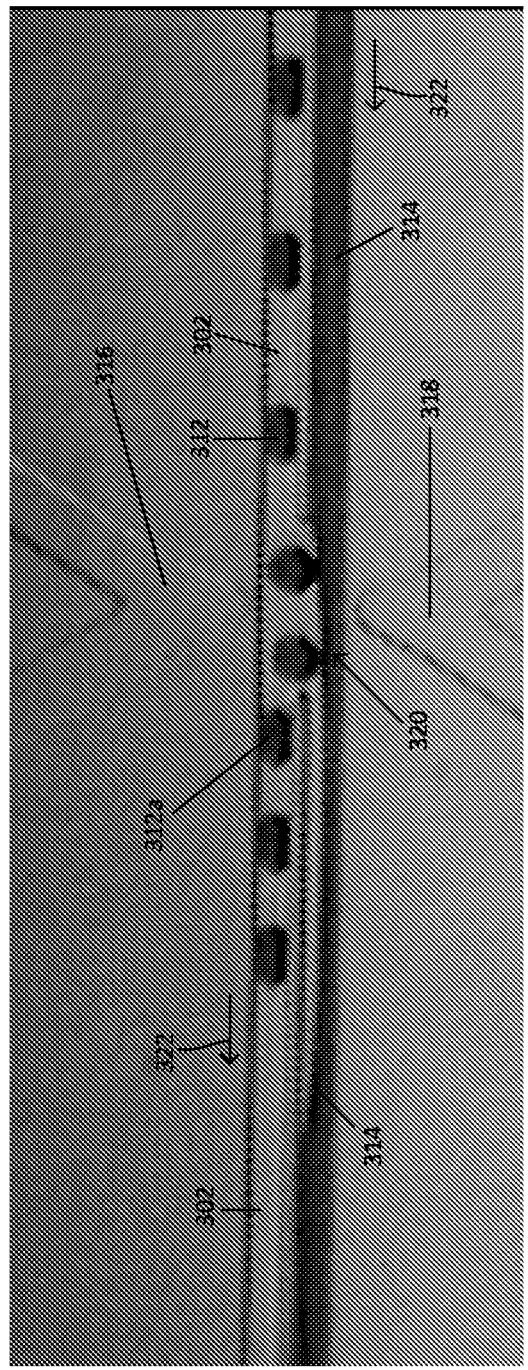
Figure 18A:
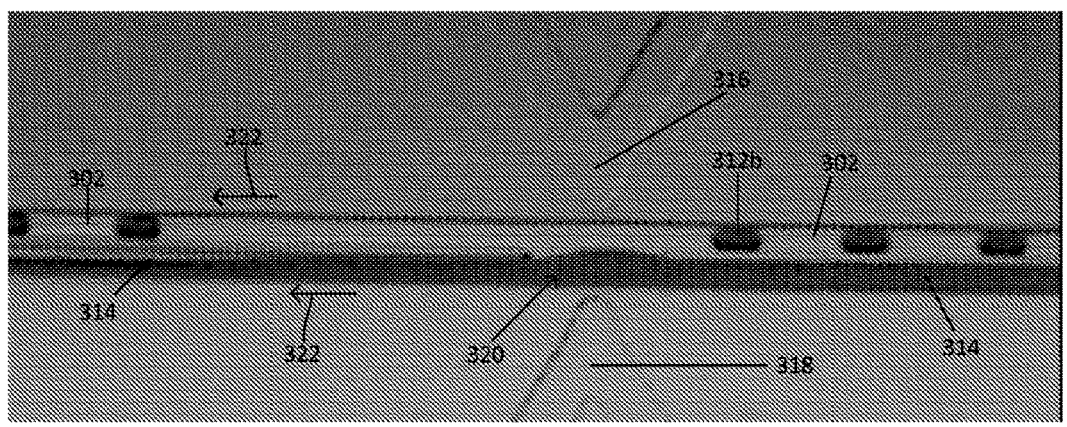
Figure 18B:
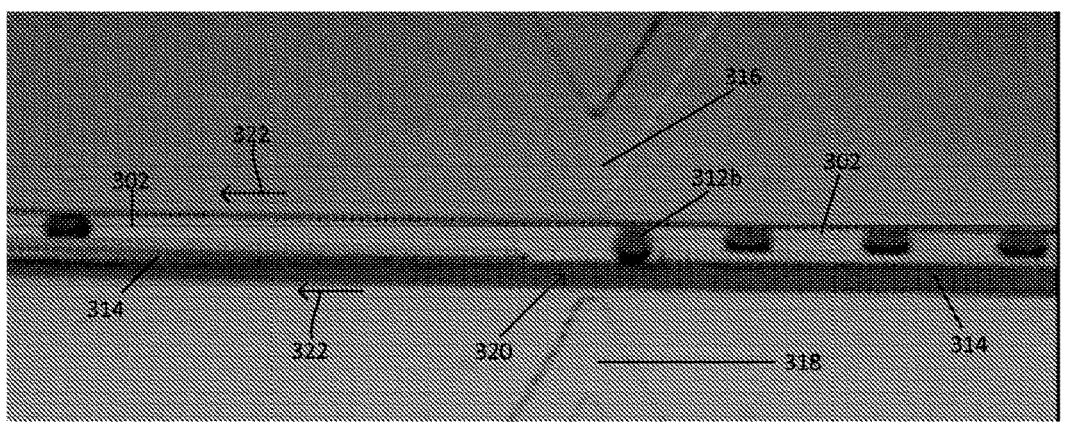
Figure 18C:
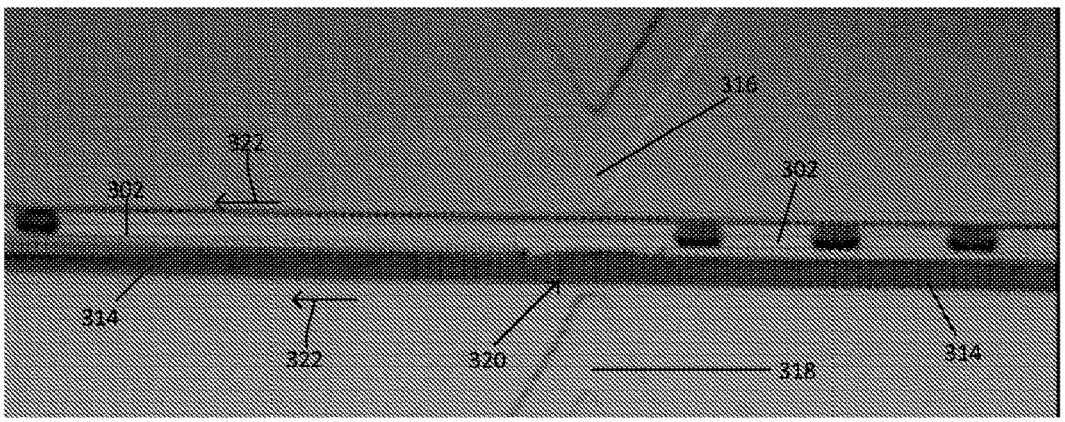

The extractor 310 can, for example, be configured to allow droplets 312 passing through main channel 302 to be remain in the main channel 302 when the source channel 316 is not producing an electrical field or to be pulled or extracted into the side channel 314 of the extractor 310 when the source channel 316 is producing an electrical field. For example, FIGS. 17A-17B show a particular droplet 312a entering the junction 320 flowing in the direction of arrow 322 when the electrical field is not present at the junction 320. As shown in FIG. 17B, the droplet 312a passes over the junction 320 remains in the main channel 302. For example, FIG. 18A-18B shows a particular droplet 312b entering the junction 320 flowing in the direction of arrow 322 when the electrical field is present. As shown in FIG. 18B, the droplet 312a passes over the junction 320 is extracted into the main channel 302.

Example 1

Immunocapture of DNA without Regional Bias

ChIP can assess protein-DNA interactions across the entire genome. However, DNA is not uniformly accessible due to variable packaging by nucleosomes (5, 42). Whereas transcriptionally active and poised genes lie in the euchromatin and have lower chromatin densities, developmentally or permanently silenced genomic regions lie in heterochromatin and are more compacted (11). Correspondingly, these regions have higher or lower sensitivity to digestion with micrococcal endonuclease (MNase), which cannot readily digest protein-bound DNA (41).

To demonstrate the ability of the disclosed device to generate immunocaptured DNA without regional bias, qPCR (used for rapid, initial assessment of efficacy) and deep sequencing was performed on the Illumina HiSeq2000 platform (used for genome-wide verification of performance) in samples representing key steps of one of the droplet microfluidic nChIC protocols provided herein (FIG. 1A).

Samples are obtained following MNase digestion applied to whole HeLa cells (module 1 of FIG. 1A); following immunocapture (nChIC) of the obligatory nucleosome component histone H3 with or without subsequent DNA purification using mono/dinucleosome preparations as input (module 2 of FIG. 1A); and also following the complete nChIC procedure applied to whole cells module 2 of FIG. 1A). The nChIC method can be performed using ChIP-seq-validated antibodies against the activating histone mark H3K4me3 (trimethylated lysine 4 of H3; Abcam ab8580) (43) and H3K27me3 (Cell Signaling Technology #9733S) (44, 45) and H3K9me3 (Abcam ab8898) (46, 47). To meet the input requirements of qPCR and deep sequencing, the output is upscaled by running the droplet generator longer. DNA fragment sizes are quantitatively analyzed with an Advanced Analytical Fragment Analyzer.

Figure 3:
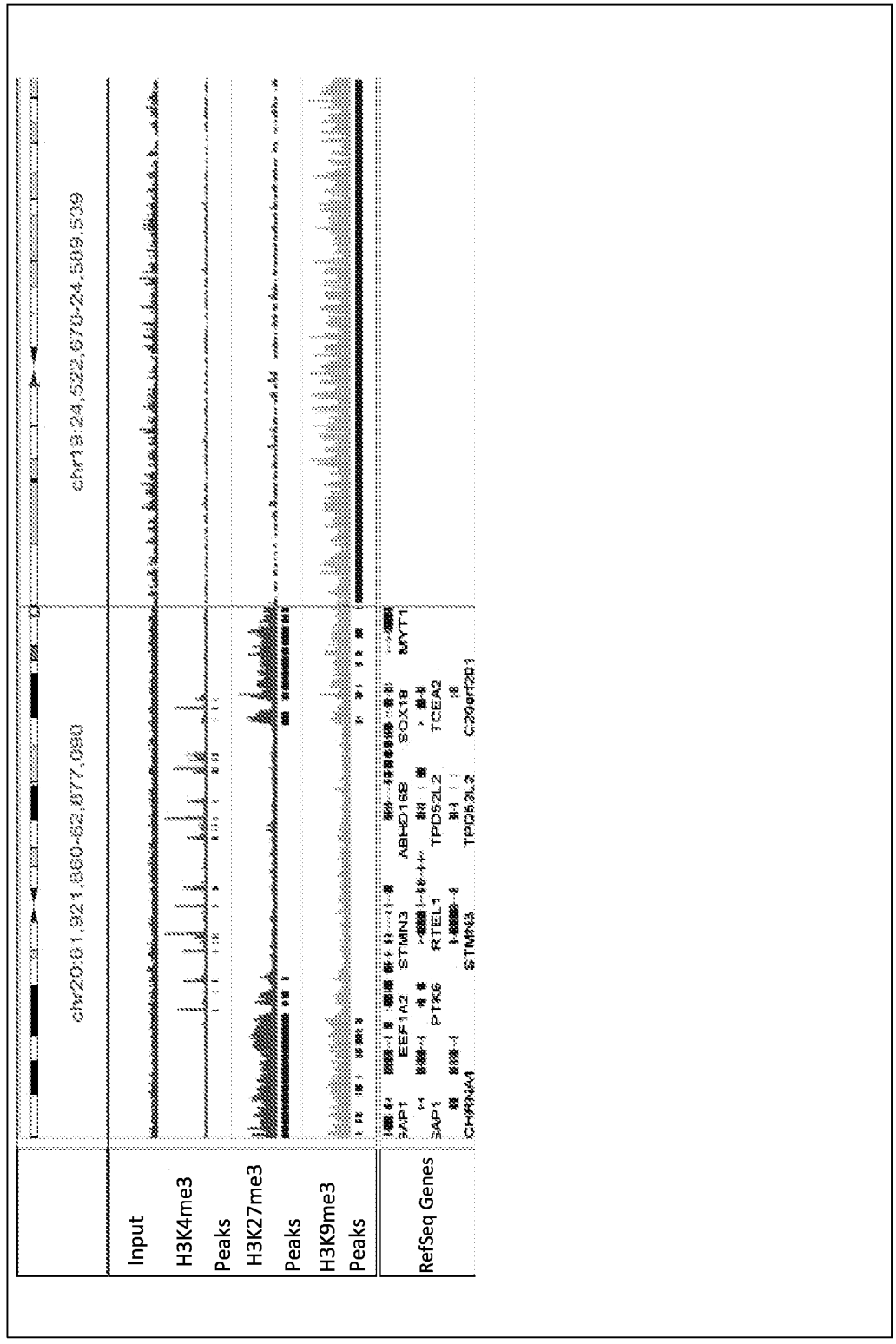
FIG. 3 shows identification of actively transcribed and repressed genes and a constitutively repressed noncoding region by ChIP-seq performed in human cells. In the middle of the left panel is a cluster of genes bearing prominent peaks of the activating histone mark trimethylated lysine 4 of histone H3 (H3K4me3; red track) on their TSS flanked by two other groups of genes displaying significant occupancy by the repressive marks H3K27me3 (blue track) and H3K9me3 (green track). Note contrasting pattern of occupancy by significant peaks of activating and repressive marks identified by MACS2 and SICER algorithms, respectively. The right panel shows a pericentromeric noncoding region (chr19) densely covered by H3K9me3 marks. Grey track, input scaled to the H3K27me3 track.

Testing for regional bias was examined by qPCR targeting an actively transcribed gene (SMARCA4 transcription start site (TSS) expected to bind H3K4me3), a developmentally repressed gene (MYT1 TSS expected to bind H3K27me3 and H3K9me3) and sequences that lie in constitutive heterochromatin (alpha-satellite DNA expected to bind H3K9me3). Enrichment vs. 1% input is calculated and compared to enrichment obtained by conventional methods (off-chip MNase-qPCR and ChIP-qPCR). In the absence of significant bias (power ≥0.8 with $\alpha=0.05$), sequencing is used to verify genome-wide coverage of genes and noncoding regions in euchromatin, facultative and constitutive heterochromatin (FIG. 3). Nucleosome-associated DNA prepared by off-chip MNase (MNase-seq) or binding profiles of H3, H3K4me3, H3K27me3 and H3K9me3 obtained by nChIC-seq to profiles generated by conventional ChIP-seq performed in the same cells were compared. For quantitative analysis, genes with significant peaks within TSS±2 kb are identified by MACS2 (H3K4me3) and SICER (H3K27me3 and H3K9me3) algorithms (48, 49) in conventional ChIP-seq data; then mean binding profiles for these gene sets are calculated from on- and off-chip MNase-seq, as well as nChIC-seq and ChIP-seq data for each individual mark and compared statistically.

FIG. 3 shows results obtained by off-chip (conventional) chromatin fragmentation and ChIP-sequencing. This experiment illustrates a reference for future on-chip chromatin preparation and ChIP. Specifically, FIG. 3 shows identification of actively transcribed and repressed genes and a constitutively repressed noncoding region by ChIP-seq performed in human cells. In the middle of the left panel is a cluster of genes bearing prominent peaks of the activating histone mark H3K4me3 (red track) on their TSS flanked by two other groups of genes displaying significant occupancy by the repressive marks H3K27me3 and H3K9me3 (blue and green tracks, respectively). Note contrasting pattern of occupancy by significant peaks of activating and repressive marks identified by MACS2 and SICER algorithms, respectively. The right panel shows a pericentromeric noncoding region (chr19) densely covered by H3K9me3 marks. Grey track, input scaled to the H3K27me3 track. Similar data will be generated from a plurality of single cells (up to $10^6$ per mark) processed using the nChIC device.

Based on these observations, immunocaptured and purified DNA obtained from single cells/droplet can be analyzed by digital droplet PCR (ddPCR) on a Bio-Rad QX100 platform, which is capable of detecting single copies of DNA. PCR reagents are introduced, within the nChIC device, into the droplets containing purified single cell-derived nChIC-DNA. Droplets are then harvested and subjected to qPCR. Droplets containing amplified nChIC-DNA can be detected and enumerated, for example by using a Bio-Rad QX100 Droplet Reader and QuantaSoft software.

Low representation of mono/dinucleosomes by DNA size analysis (~150-300 bp) or by PCR and sequencing following H3 immunocapture indicate suboptimal fragmentation and/or nChIC. The degree of the problem can be determined based on the relative prevalence of reduced representation of sequences associated with open (H3K4me3-marked) and condensed chromatin (marked by H3K27me3 and/or H3K9me3). If needed, conditions can be changed iteratively until the following quantitative benchmarks are achieved: qPCR: no statistically significant difference between on- vs. off-chip MNase-qPCR or nChIC-qPCR vs. ChIP-qPCR with power ≥0.8 and $\alpha=0.05$; sequencing: mean binding profile within TSS±2 kb obtained by on-chip MNase-seq and nChIC-seq falls within 95% confidence interval for mean binding obtained by off-chip MNase-seq and ChIP-seq, respectively.

Example 2

Generating Nucleosomes Using a Droplet Microfluidic Device

This example describes part of a microfluidic platform that can be used enzymatically process single nuclei into mono/di/trinucleosomes. This portion of the platform is suitable for genome-wide chromatin analysis by quantitative benchmarking against macroscale methods.

To achieve adequate resolution of genomic localization of bound proteins, a key early step in ChIP is chromatin fragmentation into mono/di/trinucleosomes. This is often achieved via sonication; however, enzymatic processing methods can be more amenable to microfluidic devices. Thus, the process of nucleosome preparation, inputting crosslinked cells and outputting mono/di/trinucleosomes, can be integrated and automated. Utilizing known droplet microfluidics, which include single cell encapsulation (37-40), precise injection of metered amounts of reagents (50, 51), rapid mixing (36), and controllable incubation for defined periods of time (52). An exemplary workflow for is shown in FIGS. 4A-4E. The platform is dynamically-compatible with variable sizes of input—from single cells up to macroscale ChIP input sizes.

Nuclei were generated by lysing cells with a cell lysis buffer (10 mM HEPES, pH 7.9, 1.5 mM $MgCl_2$, 10 mM KCl, 0.5% IGEPAL-CA630, and 0.5 mM Dithiothreitol (DTT)) on ice for 15 minutes. Nuclei were isolated using digestion buffer (20 mM Trizma hydrochloride, pH 7.5, 15 mM NaCl, 60 mM KCl, 5 mM $CaCl_2$, 0.15 mM spermine, 0.5 mM spermidine, 1% pluronic, 0.1% BSA) containing 80,000 Gel U per ml of MNase for 5 minutes at 4° C. Nuclei were incubated on chip for about 10 minutes, DNA samples were analyzed by running a 2% agarose gel with SYBR Gold as the dye.

The ability to robustly fragment chromatin using droplet-based MNase digestion was examined. A droplet microfluidic device capable of efficiently processing nuclei to mono/di/trinucleosomes was developed (FIG. 4A). Off-chip crosslinked HeLa nuclei from ~$10^6$ cells were exposed to MNase (0.6 U/μL) in a microfluidic channel immediately before droplet formation in a flow-focusing device geometry (53). The oil phase consisted of 3M Novec 7500 plus added fluorosurfactant. The geometries and flow rates were controlled to generate ~100 nL droplets at ~500 Hz. The contents were thoroughly mixed by passing through a serpentine channel (FIG. 4B) before moving into a delay channel (FIG. 4C). The repeatedly-constricted delay channel geometry, in which the periodic constrictions are roughly the size of a droplet, helped ensure equal transit/reaction times (52). The overall length of the delay channel was designed to give 10 minute enzymatic digestion. To quench the reaction, a solution of EDTA (100 mM Tris-HCl, pH 8, 20 mM EDTA, 200 mM NaCl, 2% Triton-X 100, 0.2% Sodium dodecyl sulfate) was injected into the droplet using a strategy similar to the electrode-free picoinjection approach reported by Abate (51) (FIG. 4D). About 100-150 pL was injected, and the reaction was allowed to proceed for 5 minutes. Quenched droplets were collected off chip, coalesced by adding fluoro-octanol, and DNA was analyzed by gel electrophoresis following release from the nucleosomes by proteinase K treatment.

As shown in FIG. 4E, both on-chip and off-chip MNase digestion performed on the same amount of input resulted in clear bands representing mono-, di-, and trinucleosomes, indicating successful chromatin fragmentation. The on-chip digestion had the same yield of mononucleosomes compared off-chip and, in fact, showed clearly less undigested chromatin. The time and MNase concentration were similar to previous reports of microfluidic ChIP (27, 28) however, in this case facile upscaling allowed direct comparison with macroscale approaches.

Based on these results, cell lysis, digestion, and quenching can be performed in the droplets.

MNase concentration and reaction time can be optimized to achieve (i) a ≥85% mono+dinucleosome yield (determined by quantitative fragment analysis) from nuclei as input; (ii) demonstrate single cell droplet encapsulation with ≥75% efficacy as determined by microscopy; (iii) demonstrate ≥70% mono+dinucleosome yield from droplet-encapsulated single cells by fragment analysis; and (iv) directly benchmark upscaled on- vs. off-chip MNase in terms of broad genomic accessibility using MNase-qPCR and MNase-seq and quantitative criteria.

Example 3

Immunocapture Using Droplet Microfluidic Device

This example describes part of a microfluidic platform that can be used to capture and purify chromatin-associated DNA from the nucleosomes generated in Example 2. This portion of the platform is suitable for genome-wide chromatin analysis by quantitative benchmarking against macroscale methods.

Figure 5A:
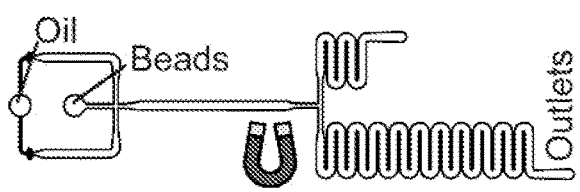
FIGS. 5A-5D. (A) Schematic diagram of a droplet microfluidic device for bead separation, wherein the T-junction splits droplets to concentrate and wash beads. (B) Optical micrograph of the T-junction used to asymmetrically separate droplets for bead enrichment and the use of a magnet to pull beads with antibody and associated chromatin into new, smaller droplet. Black arrows indicate magnetic beads (brown) within droplets. The magnet pulls beads to the bottom of the horizontal microfluidic channel and at the T-junction, the beads follow downward branch while ~⅔ of the "supernatant" follows the upward path to waste. This process can be repeated, with injections of additional wash buffer, to effectively wash the immunocapture beads for nChIC. (C) Comparison of qPCR results for immunoprecipitation for GFP-tagged histone H2B carried out in bulk over 24 hours vs. in droplets over 2.5 hours. MYT1 is a developmentally repressed gene; SAT-alpha is alpha-satellite DNA located in constitutive heterochromatin. The results indicate that within-droplet immunoprecipitation can isolate histone H2B from both facultative and constitutive heterochromatin, i.e., densely packaged genomic regions, with efficiencies comparable to conventional methods while dramatically reducing processing times. (D) Comparison of qPCR results for beads washed normally compared to beads concentrated on chip for subsequent washing.

Chromatin immunocapture is most commonly achieved through the use of antibody-conjugated magnetic beads and involves repeated sample washing, a common source of error and sample loss. The disclosed droplet microfluidic platform provides automated, continuous immunocapture for ultralow, yet variable, inputs (FIG. 5A). This portion of the device allows for bead isolation and washing, and, in contrast to previously described microfluidic ChIP devices, also integrates on-chip DNA isolation, thus eliminating manual bead collection. This multi-faceted module greatly improves the overall yield and performance over standard ChIP protocols.

Figure 5B:
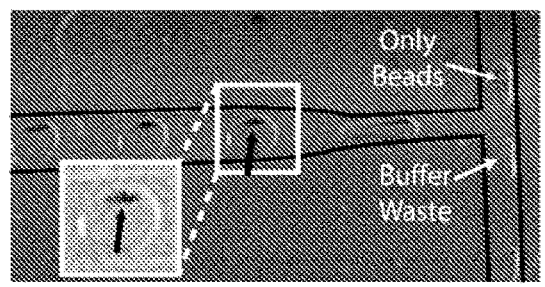

This portion of the device relies upon droplet microfluidic sample manipulation steps: droplet generation, injection, and bead separation. Thus, the immunocapture module illustrated in step 5 of FIG. 1A, as well as the bead concentration and washing steps (steps 6-9 of FIG. 1) can be achieved. The device allows for droplet splitting and magnetic particle separation. In this device (FIG. 5A), magnetic particles or beads are pulled to one side of the microfluidic channel before the droplet is split at a junction. Although a T-junction is shown, other junctions can be used, such as a Y-, or K-junction (e.g., see 24 of FIG. 6A). Channels having differential fluidic resistance allow the incoming droplet to be split at the junction (e.g., asymmetrically split). FIG. 5B shows an example of magnetic separation in which beads are exclusively directed down the lower branch along with ⅓ of the liquid whereas the rest of the "supernatant" travels through the upper branch to waste. The splitting ratio here is illustrative of the approach, but alternative designs remove 90% of the supernatant. Following droplet splitting, wash buffer is injected and the magnetic bead splitting process repeated four times, providing a fully automated, 99.99% purification.

The immunocapture module using off-chip MNase-prepared mono/di/trinucleosomes as input was examined. Droplets containing nucleosomes were generated as described in Example 2. Protein A beads pre-functionalized with anti-H3 antibody can be injected via electrodeless injection, mixed in a serpentine channel and allowed to incubate in an appropriate delay channel. Four cycles of magnetic bead separation and wash buffer injection can be performed before proteinase K injection, which release the DNA. The remaining protein A beads can optionally be removed by magnetic capture before injecting silica-coated magnetic core particles for DNA isolation (1 μm Dynabeads MyOne SILANE beads). The beads gather the released DNA and are washed using the magnetic separation design described above. Finally, DNA is eluted and beads removed via magnetic extraction giving purified nChIC-DNA.

Figure 5C:
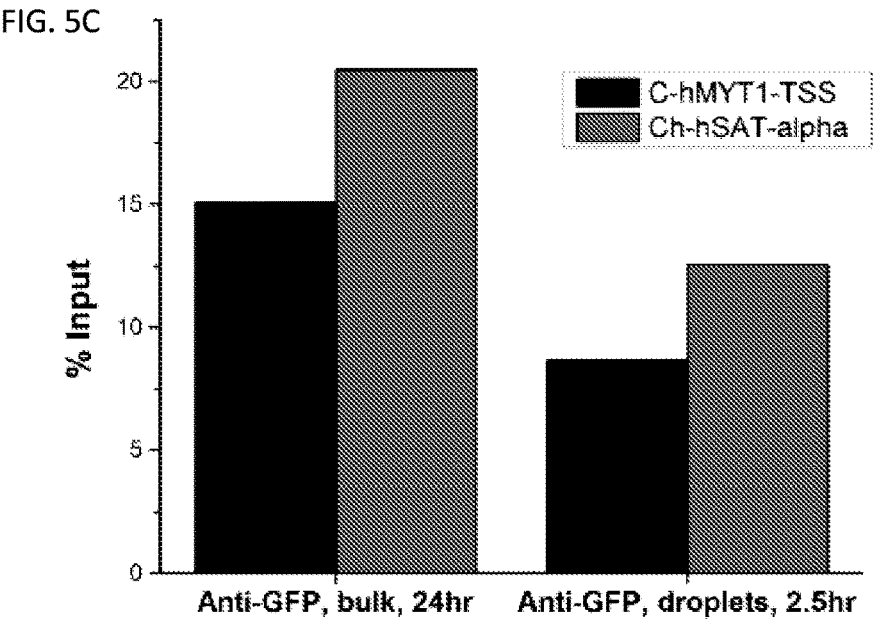
Figure 5D:
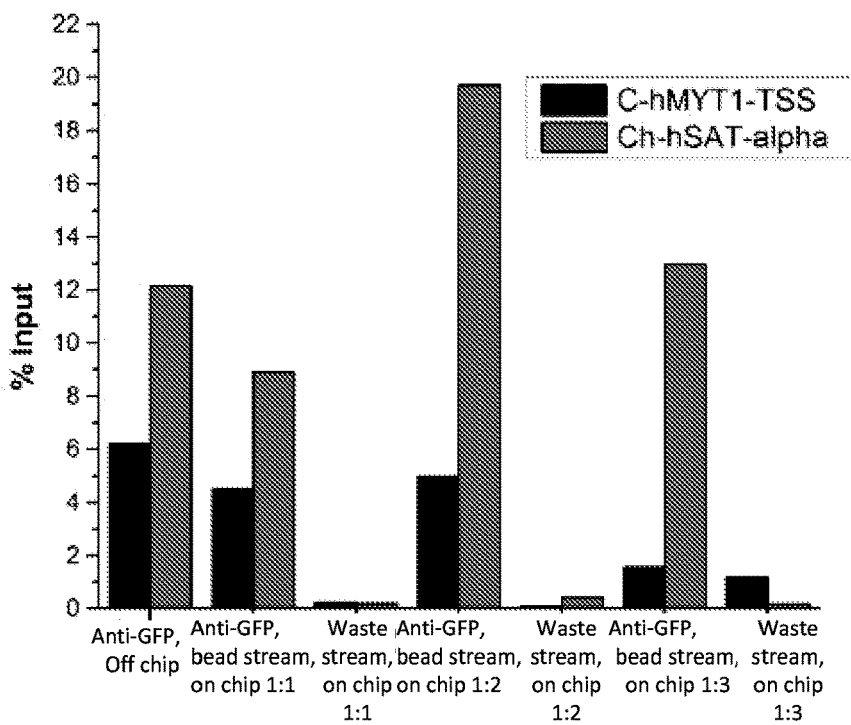

The nChIC immunocapture module was validated by upscaling input for direct comparison with macroscale ChIP-qPCR. Droplet microfluidic immunocapture of histone H2B-GFP fusion protein (using an anti-GFP antibody), and qPCR analysis was performed for the developmentally repressed MYT1 promoter and the consitutively repressed alpha-satellite (SAT) DNA. FIG. 5C shows comparison of qPCR results for immunoprecipitation for GFP-tagged histone H2B carried out in bulk over 24 hours vs. in droplets over 2.5 hours. The results indicate that within-droplet immunoprecitipation can isolate histone H2B from both facultative and constitutive heterochromatin, i.e., densely packaged genomic regions, with efficiencies comparable to conventional methods while dramatically reducing processing times. While the enrichment was lower, the recovery was acceptable, since to date, no specific enrichment of repressed targets have been shown by using microfluidic ChIP devices. Thus, high specificity and similar ratio of genomic accessibility between nChIC and macro-ChIP was observed. FIG. 5D shows qPCR results for beads washed normally compared to beads concentrated on chip for subsequent washing. The ratios represent the splitting ratio at the T-junction. For example, a 1:1 ratio is a 50-50 split to the waste and collection streams respectively. 1:2 ratio, is 1 part collection stream to 2 parts waste. Enrichment of SAT-alpha and MYT1 promoter following on-chip processing remained high and comparable to off-chip immunoprecipitation over two washing steps. qPCR can be used to examine probe enrichment as a function of cell input, extending down to 100 cells.

Thus, immunoprecipitation with antibody-functionalized magnetic beads can be carried out more quickly in droplets than in bulk, and beads can be concentrated and washed on chip using a magnet and T-junction droplet splitting device.

The nChIC module after both immunocapture and immunocapture+DNA isolation can be examined. In some examples, (i) there is no statistically significant difference between nChIC-qPCR vs. ChIP-qPCR results with power ≥0.8 and $\alpha=0.05$; and/or (ii) when comparing binding profiles of the 4 chromatin targets within TSS±2 kb of genes occupied by significant H3K4me3, H3K27me3 and H3K9me3 peaks (H3 occupancy calculated for all 3 gene sets), mean binding profiles obtained by nChIC-seq fall within the 95% confidence interval for the corresponding mean binding profiles obtained by ChIP-seq.

Example 4

Nucleosome Generation and Immunocapture Using Droplet Microfluidic Device

This example describes a combined microfluidic platform that can be used to generate nucleosomes (e.g., Example 2) and subsequently capture and purify chromatin-associated DNA from the nucleosomes generated (e.g., Example 3). This platform is suitable for genome-wide chromatin analysis by quantitative benchmarking against macroscale methods and allows streamlined single-cell qPCR analysis. This fully integrated droplet microfluidic platform provides dynamically-tunable-input nChIC-qPCR and nChIC-seq. Also leveraged is a compatibility with ddPCR to create a powerful single-cell analysis methodology that allows for interrogation of epigenomic population heterogeneity.

The MNase digestion and immunocapture modules described in Examples 2 and 3 are compatible with one another (e.g., see FIG. 1A). In some examples, the device only contains a single layer, thereby avoiding the need for complex alignment of control valve layers. Furthermore, the dynamic input characteristics make the nChIC platform amenable to the variable inputs encountered in diverse ChIP applications.

The combined device can be compared in a side-by-side comparison with macro-ChIP using 1 million HeLa cells as input. The resulting droplets of isolated DNA can be coalesced and analyzed for genomic coverage using qPCR and deep sequencing. In one example, equivalent enrichment and genomic coverage as compared to conventional macroscale ChIP is obtained.

The disclosed methods and device are compatible with digital droplet (dd)PCR, which also utilizes droplet emulsions for single-copy DNA analysis. Using the methods and devices described above, reagents for ddPCR (e.g., PCR Master Mix, primers, and TaqMan Probe Mix) can be directly introduced into droplets containing purified nChIC-DNA from single cells. These droplets can then be directly incorporated into the workflow of a ddPCR system, such as the Bio-Rad QX100 ddPCR system. In one example, to determine the epigenomic heterogeneities at the single cell level, the proportion of cells with detectable H3-, H3K4me3-, H3K27me3- and H3K9me3-bound genomic targets (SMARCA4, MYT1 and SAT) in relation to the proportion of cells in different phases of the cell cycle determined, for example by flow cytometry on propidium iodide.

In one example, the quantitative benchmarks for the qPCR and sequencing are the same as those proposed in the examples above. It is expected that H3-bound SMARCA4, MYT1 and SAT DNA will be detected in ≥75% of cells in Go/Gi.

REFERENCES CITED

1. Chan I S, Ginsburg G S. Personalized medicine: progress and promise. Annu Rev Genomics Hum Genet. 2011; 12:217-44.
2. Griewank K G, Scolyer R A, Thompson J F, Flaherty K T, Schadendorf D, Murali R. Genetic alterations and personalized medicine in melanoma: progress and future prospects. Journal of the National Cancer Institute. 2014; 106(2):djt435.
3. Roychowdhury S, Iyer M K, Robinson D R, Lonigro R J, Wu Y M, Cao X, et al. Personalized oncology through integrative high-throughput sequencing: a pilot study. Sci Transl Med. 2011; 3(111):111ra21.
4. Issa J P. Aging and epigenetic drift: a vicious cycle. J Clin Invest. 2014; 124(1):24-9.
5. Ordog T, Syed S A, Hayashi Y, Asuzu D T. Epigenetics and chromatin dynamics: a review and a paradigm for functional disorders. Neurogastroenterol Motil. 2012; 24(12):1054-68. PMID: 23095056.
6. Dulac C. Brain function and chromatin plasticity. Nature. 2010; 465(7299):728-35.
7. Reik W, Dean W, Walter J. Epigenetic reprogramming in mammalian development. Science. 2001; 293(5532): 1089-93.
8. Feinberg A P, Irizarry R A, Fradin D, Aryee M J, Murakami P, Aspelund T, et al. Personalized epigenomic signatures that are stable over time and covary with body mass index. Sci Transl Med. 2010; 2(49):49ra67.
9. Baylin S B, Jones P A. A decade of exploring the cancer epigenome—biological and translational implications. Nat Rev Cancer. 2011; 11(10):726-34.
10. Bonasio R, Tu S, Reinberg D. Molecular signals of epigenetic states. Science. 2010; 330(6004):612-6.
11. Allis C D, Jenuwein T, Reinberg D. Overview and concepts. In: Allis C D, Jenuwein T, Reinberg D, editors. Epigenetics. Cold Spring Harbor, N.Y.: Cold Spring Harbor Laboratory Press; 2007. p. 23-61.
12. Luger K, Mader A W, Richmond R K, Sargent D F, Richmond T J. Crystal structure of the nucleosome core particle at 2.8 A resolution. Nature. 1997; 389(6648):251-60.
13. Hnisz D, Abraham B J, Lee T I, Lau A, Saint-Andre V, Sigova A A, et al. Super-enhancers in the control of cell identity and disease. Cell. 2013; 155(4):934-47.
14. Whyte W A, Orlando D A, Hnisz D, Abraham B J, Lin C Y, Kagey M H, et al. Master transcription factors and mediator establish super-enhancers at key cell identity genes. Cell. 2013; 153(2):307-19.
15. Marjanovic N D, Weinberg R A, Chaffer C L. Cell plasticity and heterogeneity in cancer. Clin Chem. 2013; 59(1):168-79. Epub 2012/12/12. doi: 10.1373/clinchem.2012.184655. PubMed PMID: 23220226.
16. Carey M F, Peterson C L, Smale S T. Chromatin Immunoprecipitation (ChIP). Cold Spring Harbor Protocols. 2009; 2009 (9):pdb.prot5279.
17. Dahl J, Collas P. µChIP: Chromatin Immunoprecipitation for Small Cell Numbers. In: Collas P, editor. Chromatin Immunoprecipitation Assays: Humana Press; 2009. p. 59-74.
18. Dahl J A, Collas P. µChIP—a rapid micro chromatin immunoprecipitation assay for small cell samples and biopsies. Nucleic Acids Res. 2008; 36(3):e15.
19. Dahl J A, Collas P. A rapid micro chromatin immunoprecipitation assay (mChIP). Nat Protoc. 2008; 3(6):1032-45.
20. Acevedo L G, Iniguez A L, Holster H L, Zhang X, Green R, Farnham P J. Genome-scale ChIP-chip analysis using 10,000 human cells. BioTechniques. 2007; 43:791-7.
21. O'Neill L P, VerMilyea M D, Turner B M. Epigenetic characterization of the early embryo with a chromatin immunoprecipitation protocol applicable to small cell populations. Nat Genet. 2006; 38(7):835-41.
22. Nelson J D, Denisenko O, Soya P, Bomsztyk K. Fast chromatin immunoprecipitation assay. Nucleic Acids Res. 2006; 34(1):e2.
23. Dahl J A, Collas P. Q2ChIP, a Quick and Quantitative Chromatin Immunoprecipitation Assay, Unravels Epigenetic Dynamics of Developmentally Regulated Genes in Human Carcinoma Cells. Stem Cells. 2007; 25(4):1037-46.
24. Flanagin S, Nelson J D, Castner D G, Denisenko O, Bomsztyk K. Microplate-based chromatin immunoprecipitation method, Matrix ChIP: a platform to study signaling of complex genomic events. Nucleic Acids Res. 2008; 36(3):e17.
25. Matsuoka T, Choul Kim B, Moraes C, Han M, Takayama S. Micro- and nanofluidic technologies for epigenetic profiling. Biomicrofluidics. 2013; 7(4).
26. Oh H J, Park J Y, Park S E, Lee B Y, Park J S, Kim S-K, et al. DNA-Enrichment Microfluidic Chip for Chromatin Immunoprecipitation. Anal Chem. 2009; 81(8):2832-9.
27. Geng T, Bao N, Litt M D, Glaros T G, Li L, Lu C. Histone modification analysis by chromatin immunoprecipitation from a low number of cells on a microfluidic platform. Lab Chip. 2011; 11(17):2842-8.
28. Wu A R, Hiatt J B, Lu R, Attema J L, Lobo N A, Weissman I L, et al. Automated microfluidic chromatin immunoprecipitation from 2,000 cells. Lab Chip. 2009; 9(10):1365-70.
29. Wu A R, Kawahara T L A, Rapicavoli N A, Riggelen Jv, Shroff E H, Xu L, et al. High throughput automated chromatin immunoprecipitation as a platform for drug screening and antibody validation. Lab Chip. 2012; 12(12):2190-8.
30. Geng T, Bao N, Litt M D, Glaros T G, Li L, Lu C. Histone modification analysis by chromatin immunoprecipitation from a low number of cells on a microfluidic platform. Lab Chip. 2011; 11(17):2842-8.
31. Tran T M, Lan F, Thompson C S, Abate A R. From tubes to drops: droplet-based microfluidics for ultrahigh-throughput biology. J Phys D: Appl Phys. 2013; 46(11):114004.
32. Joensson H N, Andersson Svahn H. Droplet Microfluidics-A Tool for Single-Cell Analysis. Angew Chem, Int Ed. 2012; 51(49):12176-92.
33. Zagnoni M, Cooper J M. Chapter 2—Droplet Microfluidics for High-throughput Analysis of Cells and Particles. In: Zbigniew Darzynkiewicz EHAOWT, Donald W, editors. Methods Cell Biol: Academic Press; 2011. p. 23-48.
34. Song H, Chen D L, Ismagilov R F. Reactions in Droplets in Microfluidic Channels. Angew Chem, Int Ed. 2006; 45(44):7336-56.
35. Roach L S, Song H, Ismagilov R F. Controlling Nonspecific Protein Adsorption in a Plug-Based Microfluidic System by Controlling Interfacial Chemistry Using Fluorous-Phase Surfactants. Anal Chem. 2004; 77(3):785-96.
36. Tice J D, Song H, Lyon A D, Ismagilov R F. Formation of Droplets and Mixing in Multiphase Microfluidics at Low Values of the Reynolds and the Capillary Numbers. Langmuir. 2003; 19(22):9127-33.
37. Brouzes E. Droplet Microfluidics for Single-Cell Analysis. In: Lindström S, Andersson-Svahn H, editors. Single-Cell Analysis: Humana Press; 2012. p. 105-39.
38. Edd J F, Di Carlo D, Humphry K J, Koster S, Irimia D, Weitz D A, et al. Controlled encapsulation of single-cells into monodisperse picolitre drops. Lab Chip. 2008; 8(8):1262-4.
39. He M, Edgar J S, Jeffries G D M, Lorenz R M, Shelby J P, Chiu D T. Selective Encapsulation of Single Cells and Subcellular Organelles into Picoliter- and Femtoliter-Volume Droplets. Anal Chem. 2005; 77(6):1539-44.
40. Kemna E W M, Schoeman R M, Wolbers F, Vermes I, Weitz D A, van den Berg A. High-yield cell ordering and deterministic cell-in-droplet encapsulation using Dean flow in a curved microchannel. Lab Chip. 2012; 12(16):2881-7.
41. Platt J L, Kent N A, Harwood A J, Kimmel A R. Analysis of chromatin organization by deep sequencing technologies. Methods Mol Biol. 2013; 983:173-83.
42. Bannister A J, Kouzarides T. Regulation of chromatin by histone modifications. Cell research. 2011; 21(3):381-95.
43. Shilatifard A. The COMPASS family of histone H3K4 methylases: mechanisms of regulation in development and disease pathogenesis. Annu Rev Biochem. 2012; 81:65-95.
44. Simon J A, Kingston R E. Occupying chromatin: Polycomb mechanisms for getting to genomic targets, stopping transcriptional traffic, and staying put. Molecular cell. 2013; 49(5):808-24.
45. Grzenda A, Ordog T, Urrutia R. Polycomb and the emerging epigenetics of pancreatic cancer. J Gastrointest Cancer. 2011; 42(2):100-11. PMID: 21336826.
46. Lomberk G, Wallrath L, Urrutia R. The Heterochromatin Protein 1 family. Genome biology. 2006; 7(7):228.
47. Urrutia R. KRAB-containing zinc-finger repressor proteins. Genome biology. 2003; 4(10):231.
48. Feng J, Liu T, Zhang Y. Using MACS to identify peaks from ChIP-Seq data. Curr Protoc Bioinformatics. 2011; Chapter 2:Unit 2 14.
49. Garmire L X, Garmire D G, Huang W, Yao J, Glass C K, Subramaniam S. A global clustering algorithm to identify long intergenic non-coding RNA—with applications in mouse macrophages. PLoS One. 2011; 6(9):e24051.
50. Abate A R, Hung T, Mary P, Agresti J J, Weitz D A. High-throughput injection with microfluidics using picoinjectors. Proceedings of the National Academy of Sciences. 2010; 107(45):19163-6.

51. O'Donovan B, Eastburn D J, Abate A R. Electrode-free picoinjection of microfluidic drops. Lab Chip. 2012; 12(20):4029-32.
52. Frenz L, Blank K, Brouzes E, Griffiths A D. Reliable microfluidic on-chip incubation of droplets in delay-lines. Lab Chip. 2009; 9(10):1344-8.
53. Anna S L, Bontoux N, Stone H A. Formation of dispersions using "flow focusing" in microchannels. Appl Phys Lett. 2003; 82(3):364-6.
54. Lee H, Xu L, Ahn B, Lee K, Oh K. Continuous-flow in-droplet magnetic particle separation in a droplet-based microfluidic platform. Microfluid Nanofluid. 2012; 13(4): 613-23.

In view of the many possible embodiments to which the principles of the disclosure may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

We claim:

1. A method of analyzing non-nucleosomal DNA, comprising:
    encapsulating an aqueous solution comprising a single cell and a lysing solution within a single droplet, wherein the single cell comprises nucleosomes, and wherein the single droplet comprises oil and a surfactant, thereby lysing the cell within the single droplet;
    adding to the single droplet a nuclease solution, thereby cleaving DNA in the single droplet;
    adding to the single droplet a quenching solution, thereby quenching the nuclease;
    adding to the single droplet a solution containing a first solid support comprising one or more binding reagents that specifically bind to all nucleosomes;
    allowing the first solid support to bind to its target within the single droplet;
    separating the solid support from non-nucleosomal DNA in the single droplet;
    adding to the single droplet a second solid support coupled to a reagent that binds the non-nucleosomal DNA;
    separating the single droplet into a portion containing the second solid support and a portion containing the non-nucleosomal DNA;
    collecting the portion of the single droplet containing the non-nucleosomal DNA; and
    analyzing the non-nucleosomal DNA.

2. The method of claim 1, wherein collecting the portion of the single droplet containing the non-nucleosomal DNA comprises combining the non-nucleosomal DNA from a plurality of single droplets.

3. A method of analyzing DNA associated with nucleosomes, comprising:
    encapsulating an aqueous solution comprising a single cell and a lysing solution within a single droplet, wherein the single cell comprises nucleosomes, and wherein the single droplet comprises oil and a surfactant, thereby lysing the cell within the single droplet;
    adding to the single droplet a non-nucleosome-cleaving nuclease solution, thereby cleaving DNA in the single droplet without substantially affecting portions of the DNA that interact with histones within the nucleosomes;
    adding to the single droplet a quenching solution, thereby quenching the non-nucleosome-cleaving nuclease;
    adding to the single droplet a solution containing a first solid support comprising one or more binding reagents that specifically bind to a histone, histone variant, histone mark, histone regulator, transcription factor or modified bases within DNA;
    allowing the first solid support to bind to its target within the single droplet;
    concentrating the first solid support bound to its target and the DNA;
    adding to the single droplet an enzyme solution that releases DNA from the solid support;
    adding to the single droplet a second solid support coupled to a reagent that binds the released DNA;
    separating the single droplet into a portion containing the second solid support and a portion containing the DNA;
    collecting the portion of the single droplet containing the DNA; and
    analyzing the DNA.

4. The method of claim 1, wherein analyzing the non-nucleosomal DNA comprises amplification of the non-nucleosomal DNA and/or sequencing the non-nucleosomal DNA.

5. The method of claim 4, wherein amplification of the non-nucleosomal DNA comprises digital droplet polymerase chain reaction (ddPCR).

6. The method of claim 1, wherein the adding steps comprise adding reagents to the single droplet by destabilizing the single droplet with a high voltage (HV) field.

7. The method of claim 1, wherein the single cell within a single droplet is present in a curved microchannel.

8. The method of claim 1, wherein a plurality of single cells within a plurality of single droplets are analyzed contemporaneously.

9. The method of claim 1, wherein the first solid support comprises magnetic beads.

10. The method of claim 1, wherein one or more of the steps are automated.

11. The method of claim 1, wherein DNA and protein complexes within the cell are crosslinked prior to encapsulating the cell within the single droplet.

12. The method of claim 1, wherein the single cell is a eukaryotic cell.

13. The method of claim 12, wherein the eukaryotic cell is a human cell, invertebrate cell, amphibian cell, or bird cell.

* * * * *